United States Patent
Tsukida et al.

[11] Patent Number: 5,919,769
[45] Date of Patent: Jul. 6, 1999

[54] FUCOSE DERIVATIVES, DRUGS CONTAINING THE SAME AS ACTIVE INGREDIENT, AND INTERMEDIATES FOR PRODUCING THE SAME

[75] Inventors: Takahiro Tsukida, Osaka; Takao Kiyoi, Mino; Toshio Achiha, Minamikawachi-gun; Hideki Moriyama, Osaka; Kiriko Kurokawa, Osaka; Hiroshi Ohmoto, Osaka; Kenji Nakamura, Osaka; Hirosato Kondo, Suita; Yukihisa Wada, Osaka; Tadayuki Saito, Osaka, all of Japan

[73] Assignee: Kanebo, Ltd, Tokyo, Japan

[21] Appl. No.: 09/051,846

[22] PCT Filed: Oct. 23, 1996

[86] PCT No.: PCT/JP96/03081

§ 371 Date: Apr. 22, 1998

§ 102(e) Date: Apr. 22, 1998

[87] PCT Pub. No.: WO97/15585

PCT Pub. Date: May 1, 1997

[30] Foreign Application Priority Data

Oct. 26, 1995 [JP] Japan ............ 7/303476
Jun. 13, 1996 [JP] Japan ............ 8/175487
Aug. 12, 1996 [JP] Japan ............ 8/231482

[51] Int. Cl.⁶ ............ A61K 31/70; C07H 15/20
[52] U.S. Cl. ............ 514/25; 536/17.2
[58] Field of Search ............ 514/25; 536/17.2

[56] References Cited

U.S. PATENT DOCUMENTS 5,444,050  8/1995  Kogan et al. .

FOREIGN PATENT DOCUMENTS

95/04751  2/1995  WIPO .
95/10296  4/1995  WIPO .

OTHER PUBLICATIONS

Buerke, M. et al., "Sialyl Lewis$^x$–Containing Oligosaccharide Attenuates Myocardial Reperfusion Injury in Cats", *J. Clin. Invest.*, 93:1140–1148 (Mar. 1994).

Okada, Y. et al., "P–Selectin and Intercellular Adhesion Molecule–1 Expression After Focal Brain Ischemia and Reperfusion", Stoke, 25(1):202–211 (Jan. 1994).

*Primary Examiner*—Deborah C. Lambkin
*Attorney, Agent, or Firm*—Merchant, Gould, Smith, Edell, Welter & Schmidt

[57] ABSTRACT

A compound of the formula (I):

wherein $X^1$ is a group of one of the following formulae (1), (2) and (3):

$R^1$ is a branched long chain alkyl group, $R^2$ is $—CONHR^3$, a carboxyl group or a hydrogen atom, n is an integer of 0, 1 or 2, and $R^3$ is a lower alkyl group or a phenyl group, or a pharmaceutically acceptable salt thereof, which is useful as a selectin inhibitor, and can be used in the prophylaxis or treatment of various inflammatory diseases such as inflammatory dermatitis (e.g., atopic dermatitis, contact hypersensitivity, photodermatosis, etc.), autoimmune chronic diseases (e.g. rheumatoid arthritis, chronic thyroiditis, etc.), and ischemia-reperfusion injury.

7 Claims, No Drawings

FUCOSE DERIVATIVES, DRUGS CONTAINING THE SAME AS ACTIVE INGREDIENT, AND INTERMEDIATES FOR PRODUCING THE SAME

This application is a 371 of PCT/JP96/03081 filed Oct. 23, 1996.

TECHNICAL FIELD

The present invention relates to a novel fucose derivative, a drug containing the same as an active ingredient, and an intermediate for producing the same. More particularly, the present invention relates to a novel compound of the formula (I):

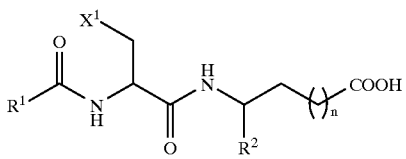

wherein $X^1$ is a group of one of the following formulae (1), (2) and (3):

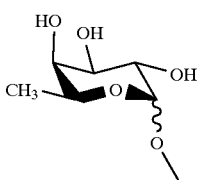

(1)

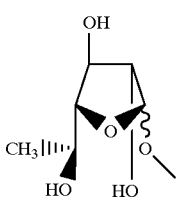

(2)

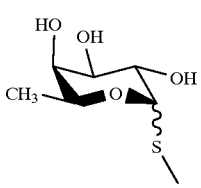

(3)

$R^1$ is a branched long chain alkyl group, $R^2$ is —CONHR$^3$, a carboxyl group or a hydrogen atom, n is an integer of 0, 1 or 2, and $R^3$ is a lower alkyl group or a phenyl group, or a pharmaceutically acceptable salt thereof, which is useful as a compound inhibiting the binding of selectin, a cell adhesion molecule, to sialyl Lewis X (hereinbelow, referred to as sialyl Le$^x$) sugar chain.

The present invention also relates to an intermediate for producing these novel fucose derivatives or a pharmaceutically acceptable salt thereof.

BACKGROUND ART

Recently, much attention has been paid to the role of selectin which is a cell adhesion molecule in various inflammatory diseases. For example, there have been known some kinds of selectin, e.g., E-selectin (occasionally referred to as ELAM-1), P-selectin (occasionally referred to as GMP-140), L-selectin (occasionally referred to as LECAM-1), etc., and these selectins are present on various cells in the progress of inflammatory response.

For example, E-selectin is an adhesion molecule which is mainly induced on the surface of vascular endothelial cells by stimuli with TNFα (tumor necrosis factor α), IL-1 (interleukin 1); P-selectin is an adhesion molecule which is mainly induced at platelet α-granules or Wiebel-Pallade corpuscle of vascular endothelial cells by the stimuli with thrombin, histamine, etc.; and L-selectin is an adhesion molecule which is present on the surface of leucocyte cells.

Generally, cell infiltration is one of the most important symptoms of inflammation, and it is known that white blood cells in the blood bind to the vascular endothelial cells, and then infiltrate into the affected tissue. Prior to the attachment of white blood cells to vascular endothelial cells, the white blood cells roll along the endothelium, which is called "rolling". The "rolling" is the important event as the first stage of cell infiltration, and it is mediated by the binding of the above-mentioned various selectins to sialyl Le$^x$ sugar chain (ligand of selectin) which is present on the surface of white blood cells.

Therefore, there have been tried treatments of various inflammatory diseases by blocking the binding of selectin to sialyl Le$^x$ oligosaccharide, and inhibiting adhesion of white blood cells. As a selectin ligand (counter ligand) inhibiting the adhesion of white blood cells, there are known peptide counter ligands (e.g., WO 95/04751, WO 95/10296, etc.) in addition to some sialyl Le$^x$ derivatives, and these ligands are compounds having only fucose as a sugar moiety.

Drugs containing a counter ligand of selectin as an active ingredient (selectin inhibitors) can suppress and control various inflammatory diseases such as inflammatory dermatitis (e.g., atopic dermatitis, contact hypersensitivity, photodermatosis, etc.), autoimmune chronic diseases (e.g. rheumatoid arthritis, chronic thyroiditis, etc.), and the like, by inhibiting the adhesion of white blood cells.

Besides, in case of ischemia-reperfusion injury, it has been reported that various selectins participate in the endothelial cell injures caused by neutrophil infiltration (cf., stroke, 25, 202–210 (1994)). In fact, it has been reported that ischemia-reperfusion injury in reflow animal models is suppressed by a sialyl Le$^x$ derivative which is a counter ligand of selectin (cf., J. Clin. Invest., 93, 1140–1148 (1994)]. Therefore, a selectin inhibitor can show inhibitory effects on ischemia-reperfusion injury as well (cf., U.S. Pat. No. 5,444,050).

DISCLOSURE OF INVENTION

An object of the present invention is to provide a novel fucose derivative or a pharmaceutically acceptable salt thereof, which inhibits the binding of selectin to sialyl Le$^x$, a drug containing the same as an active ingredient, and an intermediate for producing the same.

The present inventors have intensively studied, and found that a glycopeptide having a long chain alkyl group represented by the above formula (I) shows a potent inhibitory effect on the binding of selectin to sialyl Le$^x$, and finally have accomplished the present invention.

BEST MODE FOR CARRYING OUT THE INVENTION

The compounds of the present invention are compounds of the following formula (I):

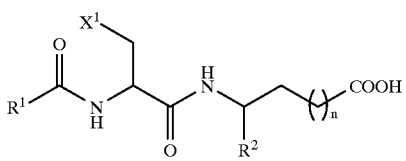

wherein X¹ is a group of one of the following formulae (1), (2) and (3):

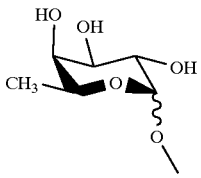

(1)

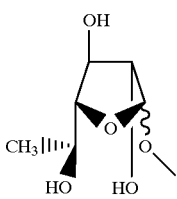

(2)

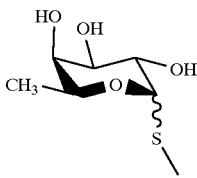

(3)

R¹ is a branched long chain alkyl group, R² is —CONHR³, a carboxyl group or a hydrogen atom, n is an integer of 0, 1 or 2, and R³ is a lower alkyl group or a phenyl group, or a pharmaceutically acceptable salt thereof.

The branched long chain alkyl group means an alkyl group having 23 to 40 carbon atoms and said carbon chain branches at the α-position or the β-position, for example, 1-(decyl)tridecyl group, 1-(dodecyl)tridecyl group, 1-(dodecyl)pentadecyl group, 1-(dodecyl)heptadecyl group, 1-(dodecyl)nonadecyl group, 1-(tetradecyl)pentadecyl group, 1-(tetradecyl)heptadecyl group, 1-(tetradecyl) nonadecyl group, 1-(hexadecyl)heptadecyl group, 1-(hexadecyl)-nonadecyl group, 1-(octadecyl)nonadecyl group, 2-(hexyl)tridecyl group, 2-(octyl)tridecyl group, 2-(decyl)tridecyl group, 2-(dodecyl)tridecyl group, 2-(dodecyl)pentadecyl group, 2-(dodecyl)heptadecyl group, 2-(dodecyl)nonadecyl group, 2-(tridecyl)pentadecyl group, 2-(tetradecyl)pentadecyl group, 2-(tetradecyl)heptadecyl group, 2-(tetradecyl)nonadecyl group, 2-(hexadecyl) heptadecyl group, 2-(hexadecyl)nonadecyl group, 2-(octadecyl)nonadecyl group, etc.

The lower alkyl group means a straight chain or branched chain alkyl group having 1 to 4 carbon atoms, for example, methyl, ethyl, n-propyl, iso-propyl, n-butyl, sec-butyl, tert-butyl, etc.

The pharmaceutically acceptable salt of the present compounds includes salts with an inorganic base (e.g., sodium salt, potassium salt, calcium salt, etc.) and salts with an organic base (e.g., arginine salt, lysine salt, etc.).

Among the compounds of the formula (I), preferable compounds are compounds of the formula (I) wherein R¹ is a branched long chain alkyl group having 23 to 31 carbon atoms, R² is carboxyl group, N-methylcarbamoyl group, N-phenylcarbamoyl group, or a hydrogen atom, and n is an integer of 0 to 2. The preferably pharmaceutically acceptable salts are sodium salt as an inorganic basic salt, and arginine salt as an organic basic salt.

The compounds of the formula I have the stereoisomer based on the peptide moiety thereof, in addition to the stereoisomer based on an anomeric asymmetric carbon atom of fucose. In the above formula (I):

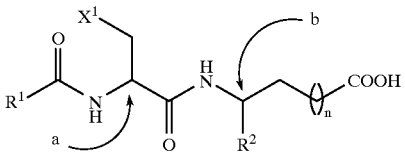

wherein R¹, R², X¹ and n are the same as defined above, the stereoisomer based on the peptide moiety means the stereoisomer based on the asymmetric carbon atoms a and b of the above formula (I) when R² is —CONHR³ or a carboxyl group, or stereoisomer based on the asymmetric carbon atom a when R² is a hydrogen atom. The present invention also includes these stereoisomer as well as a mixture thereof.

Representative compounds of the present invention are exemplified below.

[N-(2-tetradecylhexadecanoyl)-O-(α-L-fucopyranosyl)-L-seryl]-L-glutamic acid 1-methylamide

[N-(2-tetradecylhexadecanoyl)-O-(α-L-fucopyranosyl)-L-seryl]-D-glutamic acid 1-methylamide

[N-(2-tetradecylhexadecanoyl)-O-(α-L-fucopyranosyl)-D-seryl]-L-glutamic acid 1-methylamide

[N-(2-tetradecylhexadecanoyl)-O-(α-L-fucopyranosyl)-D-seryl]-D-glutamic acid 1-methylamide

[N-(2-tetradecylhexadecanoyl)-O-(β-L-fucopyranosyl)-L-seryl]-L-glutamic acid 1-methylamide

[N-(2-tetradecylhexadecanoyl)-O-(β-L-fucopyranosyl)-L-seryl]-D-glutamic acid 1-methylamide

[N-(2-tetradecylhexadecanoyl)-O-(β-L-fucopyranosyl)-D-seryl]-L-glutamic acid 1-methylamide

[N-(2-tetradecylhexadecanoyl)-O-(β-L-fucopyranosyl)-D-seryl]-D-glutamic acid 1-methylamide

[N-(2-tetradecylhexadecanoyl)-S-(α-L-fucopyranosyl)-L-cysteinyl]-L-glutamic acid 1-methylamide

[N-(2-tetradecylhexadecanoyl)-S-(α-L-fucopyranosyl)-L-cysteinyl]-D-glutamic acid 1-methylamide

[N-(2-tetradecylhexadecanoyl)-S-(α-L-fucopyranosyl)-D-cysteinyl]-L-glutamic acid 1-methylamide

[N-(2-tetradecylhexadecanoyl)-S-(α-L-fucopyranosyl)-D-cysteinyl]-D-glutamic acid 1-methylamide

[N-(2-tetradecylhexadecanoyl)-S-(β-L-fucopyranosyl)-L-cysteinyl]-D-glutamic acid 1-methylamide

[N-(2-tetradecylhexadecanoyl)-O-(α-L-fucofuranosyl)-L-seryl]-L-glutamic acid 1-methylamide

[N-(2-tetradecylhexadecanoyl)-O-(α-L-fucofuranosyl)-L-seryl]-D-glutamic acid 1-methylamide

[N-(2-tetradecylhexadecanoyl)-O-(α-L-fucofuranosyl)-D-seryl]-L-glutamic acid 1-methylamide

[N-(2-tetradecylhexadecanoyl)-O-(α-L-fucofuranosyl)-D-seryl]-D-glutamic acid 1-metlhylamide

[N-(2-tetradecylhexadecanoyl)-O-(α-L-fucofuranosyl)-L-seryl]-D-glutamic acid

[N-(2-tetradecylhexadecanoyl)-O-(L-fucofuranosyl)-L-seryl]-L-aspartic acid 1-methylamide 4-N-[N-(2-tetradecylhexadecanoyl)-O-(α-L-fucofuranosyl)-L-seryl]aminobutyric acid 5-N-[N-(2-tetradecylhexadecanoyl)-O-(α-L-fucofuranosyl)-L-seryl]aminovaleric acid

[N-(2-tetradecylhexadecanoyl)-O-(α-L-fucofuranosyl)-L-seryl]-D-glutamic acid 1-anilide

[N-(2-tetradecylhexadecanoyl)-O-(α-L-fucofuranosyl)-L-seryl]-D-glutamic acid 1-methylamide sodium salt

[N-(2-tridecylpentadecanoyl)-O-(α-L-fucofuranosyl)-D-seryl]-L-glutamic acid 1-methylamide

[N-(2-dodecyltetradecanoyl)-O-(α-L-fucofuranosyl)-D-seryl]-L-glutamic acid 1-methylamide

[N-(2-undecyltridecanoyl)-O-(α-L-fucofuranosyl)-D-seryl]-L-glutamic acid 1-methylamide

[N-(2-tetradecylhexadecanoyl)-O-(α-L-fucofuranosyl)-L-seryl]-D-glutamic acid 1-methylamide L-arginine salt

[N-(2-tetradecylhexadecanoyl)-O-(α-L-fucopyranosyl)-L-seryl]-D-glutamic acid 1-methylamide L-arginine salt The present invention also provides intermediates for producing the compounds (I), represented by the following formulae (II), (III) and (IV).

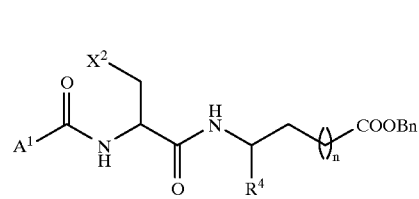
(II)

wherein $X^2$ is a group of one of the following formulae (4) and (5):

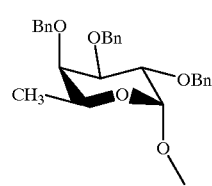
(4)

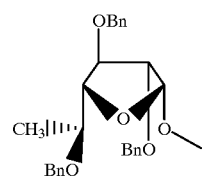
(5)

$A^1$ is a tert-butoxy group or a branched long chain alkyl group, Bn is a benzyl group, $R^4$ is —CONHR$^3$, a benzyloxycarbonyl group, or a hydrogen atom, n is an integer of 0, 1 or 2, and $R^3$ is a lower alkyl group or a phenyl group; or

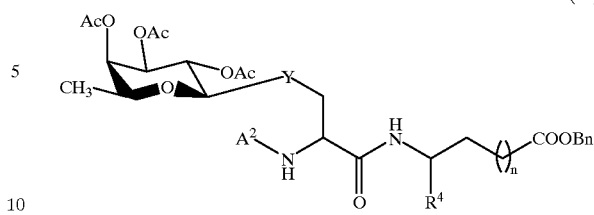
(III)

wherein Y is an oxygen atom or a sulfur atom, $A^2$ is a hydrogen atom or a branched long chain alkylcarbonyl group, Ac is an acetyl group, Bn is a benzyl group, $R^4$ is —CONHR$^3$, a benzyloxycarbonyl group, or a hydrogen atom, n is an integer of 0, 1 or 2, and $R^3$ is a lower alkyl group or a phenyl group; or

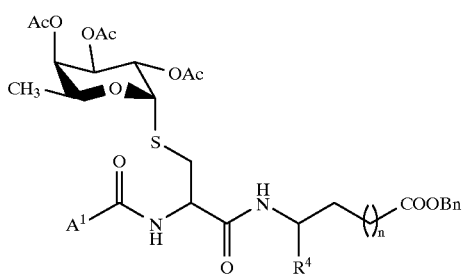
(IV)

wherein $A^1$ is a tert-butoxy group or a branched long chain alkyl group, Bn is a benzyl group, Ac is an acetyl group, $R^4$ is —CONHR$^3$, a benzyloxycarbonyl group, or a hydrogen atom, n is an integer of 0, 1 or 2, and $R^3$ is a lower alkyl group or a phenyl group.

Each abbreviation and symbol used in this description means as follows.
Bn: benzyl group
Boc: tert-butoxycarbonyl group
Boc$_2$O: di-tert-butyl dicarbonate
DMF: N,N-dimethylformamide
WSC: 1-ethyl-3-(dimethylaminopropyl)carbodiimide hydrochloride
HOBt: 1-hydroxy-1H-benzotriazole monohydrate
TFA: trifluoroacetic acid
THF: tetrahydrofuran
AgOTf: silver trifluoromethanesulfonate
SnCl$_2$: anhydrous tin chloride
TMU: 1,1,3,3-tetramethylurea
Ph: phenyl group
TEA: triethylamine
Pd(OH)$_2$/C: palladium hydroxide-carbon
Boc-Ser: N-tert-butoxycarbonyl-L-serine
Boc-D-Ser: N-tert-butoxycarbonyl-D-serine
Boc-serine: N-tert-butoxycarbonyl-L-serine or N-tert-butoxycarbonyl-D-serine, or a mixture thereof
Boc-Ser(OBn): N-tert-butoxycarbonyl-O-benzyl-L-serine
Boc-D-Ser(OBn): N-tert-butoxycarbonyl-O-benzyl-D-serine
Boc-serine(OBn): N-tert-butoxycarbonyl-O-benzyl-L-serine or N-tert-butoxycarbonyl-O-benzyl-D-serine, or a mixture thereof
DCC: dicyclohexylcarbodiimide
HPLC: high performance liquid chromatography
Ac: acetyl group
NaOMe: sodium methylate DAST: diethylaminosulfur trifluoride
DMSO: dimethylsulfoxide
NaH: sodium hydride
PhCH$_2$Br: benzyl bromide
n-Bu$_3$P: n-tributylphosphine The present compounds are prepared as follows.

(1) Preparation of the compound (Ia) [the compound of the formula (I) wherein X$^1$ is a group of the formula (1)]:

(1-1) Preparation of α-anomer [(Ia(α)] of the compound (Ia):

The α-anomer [(Ia(α)] is prepared by the following Scheme 1a.

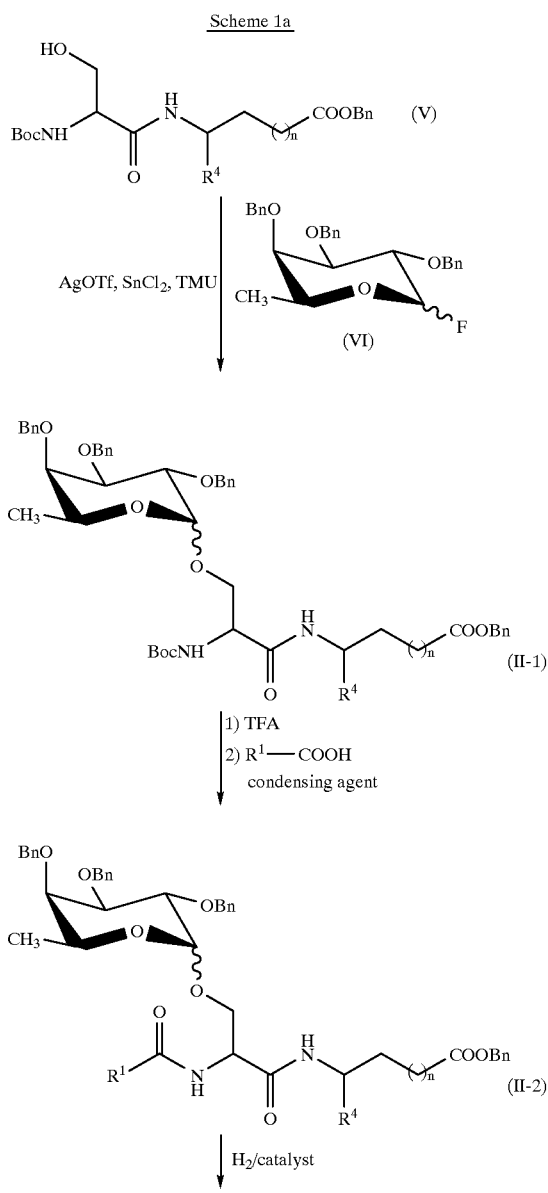

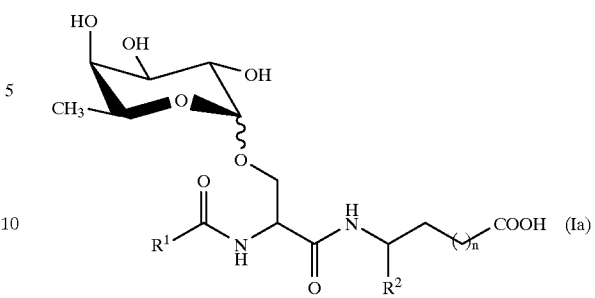

wherein R$^1$ is a branched long chain alkyl group, R$^2$ is —CONHR$^3$, a carboxyl group or a hydrogen atom, R$^4$ is —CONHR$^3$, a benzyloxycarbonyl group, or a hydrogen atom, n is an integer of 0, 1 or 2, and R$^3$ is a lower alkyl group or a phenyl group.

First, the compound (V) is glycosylated by using a glycosyl donor (VI) (cf., Journal of the American Chemical Society, 112, 3693–3695 (1990)). The compound (V) and the glycosyl donor (VI) are reacted, for example, in a solvent such as methylene chloride, in the presence of AgOTf, SnCl$_2$, and TMU, preferably at a low temperature of –40° C. to –50° C., for several hours to 24 hours to give the compound (II-1). The compound (II-1) is usually obtained in the form of a mixture of α- and β-anomers, and if necessary, the α-anomer is isolated from the mixture by recrystallization or various chromatography procedures such as HPLC, and used in the subsequent reaction. Alternatively, the compound (II-1) is used in the form of a mixture of α- and β-anomers in the subsequent reaction without further purification, and then the desired α-anomer [Ia(α)] is separated from the compound (II-2) or the final compound (Ia).

The Boc-group of the compound (II-1) is removed. The reaction is carried out in a solvent such as methylene chloride or without a solvent by stirring with adding 10 equivalent to solvent amount of TFA, at a temperature of 0° C. to room temperature, for 0.5 to 3 hours. After the reaction is completely over, TFA (and solvent) is removed by distillation under reduced pressure, and the resultant is neutralized with a base such as sodium hydrogen carbonate, TEA, and then immediately used in the subsequent reaction.

The product thus obtained is condensed with a carboxylic acid (R$^1$—COOH) using a condensing agent in an inert solvent (e.g., DMF, etc.) to give the compound (II-2). The condensing agent includes, for example, DCC, WSC, etc., and if necessary, the condensation reaction is carried out by stirring in the presence of a condensation promoter such as HOBt, etc., at a temperature of 0° C. to room temperature, for 2 to 24 hours. The carboxylic acid (R$^1$—COOH), the condensing agent and the condensation promoter are used in an amount of 0.8–1.2 mole, 1.0–1.5 mole, and 1.0–1.5 mole, respectively, to 1 mole of the compound (II-1).

Finally, the compound (II-2) is subjected to hydrogenolysis to give the compound (Ia). The hydrogenolysis is carried out in ethanol or 1,4-dioxane, if necessary, by adding water, hydrochloric acid, acetic acid, etc., in the presence of a catalyst such as 10% palladium-carbon, 20% palladium hydroxide-carbon, platinum, etc., under hydrogen atmosphere or under hydrogen pressure, at a temperature of room temperature to 60° C.

(1-2) Preparation of β-anomer [Ia(β)] of the compound (Ia):

In the glycosylation reaction in the above Scheme 1a, a mixture of α-anomer and β-anomer of the compound (Ia) is obtained. In the same manner as in the preparation of α-anomer, β-anomer [Ia(β)] can be also prepared.

Alternatively, β-anomer [Ia(β)] is prepared by the following Scheme 2a.

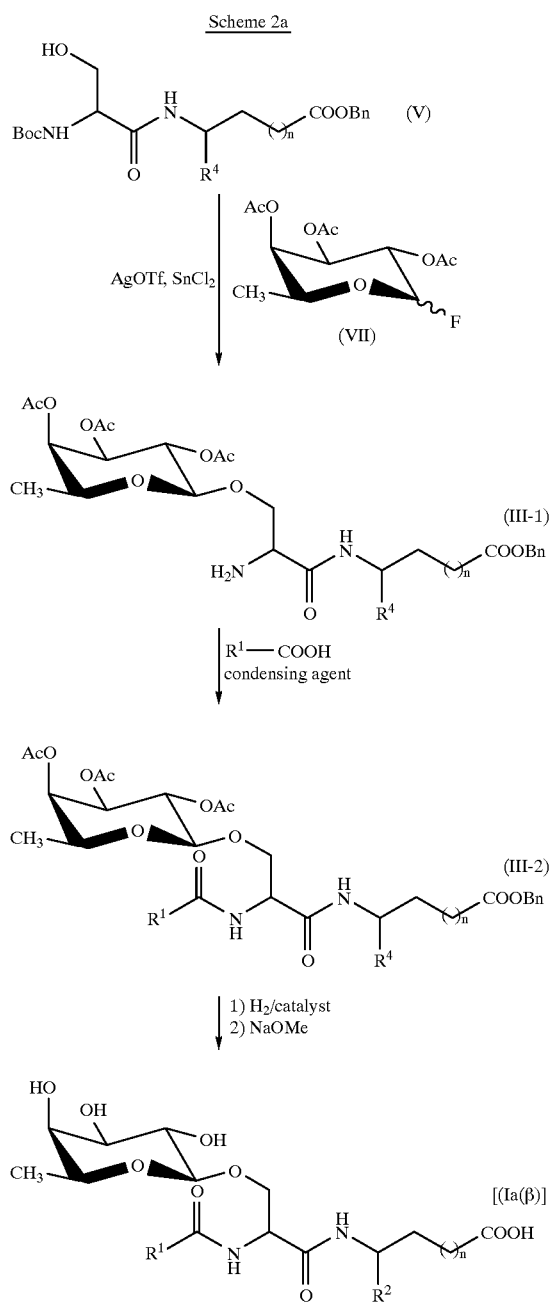

wherein $R^1$, $R^2$, $R^4$ and n are the same as defined above.

First, the compound (V) is glycosylated by using a glycosyl donor (VII) (cf., Carbohydrate Research, 200, 391–402 (1990)). The compound (V) and the glycosyl donor (VII) are reacted, for example, in a solvent such as methylene chloride, in the presence of AgOTf and $SnCl_2$, preferably at a temperature of −25° C. and −15° C., for several hours to 24 hours, to selectively give the compound (III-1).

The product thus obtained is condensed with a carboxylic acid ($R^1$—COOH) with using a condensing agent in an inert solvent (e.g., DMF, etc.) to give the compound (III-2). The condensing agent includes, for example, DCC, WSC, etc., and if necessary, the condensation reaction is carried out by stirring in the presence of a condensation promoter such as HOBt, etc., at a temperature of 0° C. to room temperature, for 2 to 24 hours. The carboxylic acid ($R^1$—COOH), the condensing agent and the condensation promoter are used in an amount of 0.8–1.2 mole, 1.0–1.5 mole, and 1.0–1.5 mole, respectively, to 1 mole of the compound (III-1).

Finally, the compound (III-2) is subjected to hydrogenolysis, and then the acetyl groups thereof are removed to give the β-anomer [Ia(β)]. The hydrogenolysis is carried out in ethanol or 1,4-dioxane, if necessary, by adding water, hydrochloric acid, acetic acid, etc., in the presence of a catalyst such as 10% palladium-carbon, 20% palladium hydroxide-carbon, platinum, etc., under hydrogen atmosphere or under hydrogen pressure, at a temperature of room temperature to 60° C.

The removal of the acetyl groups is usually carried out by stirring the mixture in a lower alcohol (e.g., methanol, ethanol, etc.), with using a 28% NaOMe/methanol solution at room temperature for 0.5 to 1.5 hour.

(2) Preparation of the compound (Ib) [the compound of the formula (I) wherein $X^1$ is a group of the formula (2)]:

The compound (Ib) of the present invention is prepared by the following Scheme 1b, according to the process for preparing the compound (Ia) as shown in the above Scheme 1a.

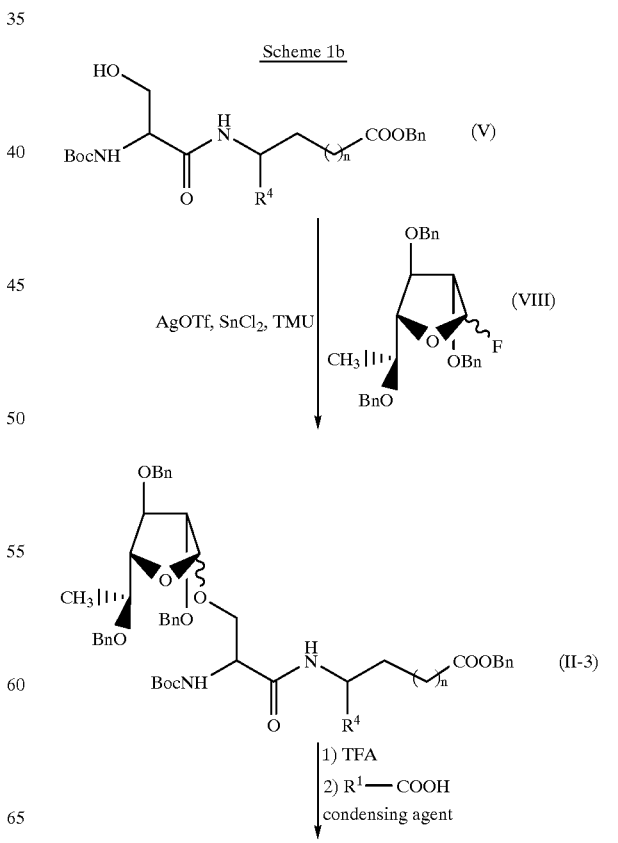

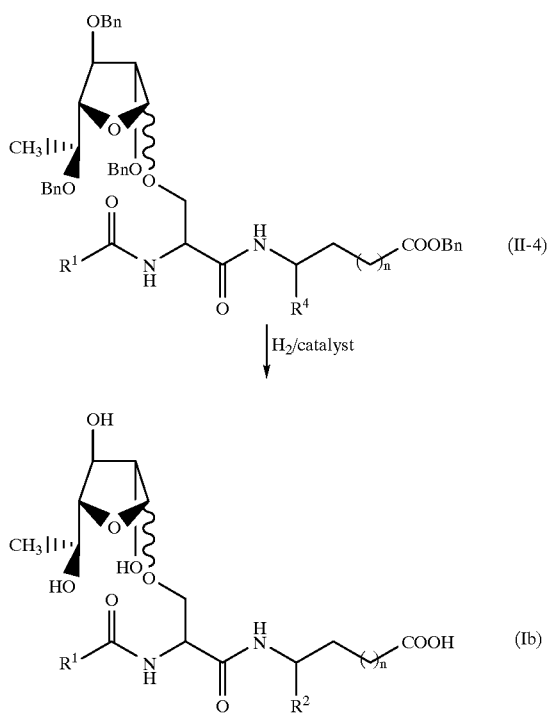

wherein $R^1$, $R^2$, $R^4$ and n are the same as defined above.

First, the compound (Ib) is prepared in the same manner as in the preparation of the compounds [Ia(α)] and [Ia(β)] in the above Scheme 1a except that the glycosyl donor (VIII) is prepared according to the method disclosed in the literature (Biological & Pharmaceutical Bulletin, 18 (11), 1487–1491 (1995)). The compound (V) is glycosylated to give a mixture of α- and β-anomers, and the desired anomer is separated from the other in the intermediate compound (II-3) or (II-4), and converted into the desired final compound (Ib). Alternatively, the mixture of both anomers is converted into the desired compound (Ib), and then the desired anomer [Ib(α)] or [Ib(β)] is separated.

(3) Preparation of the compound (Ic) [the compound of the formula (I) wherein $X^1$ is a group of the formula (3)]:

(3-1) Preparation of α-anomer [Ic(α)] of the compound (Ic):

The α-anomer [Ic(α)] of the compound (Ic) is prepared by the following Scheme 3.

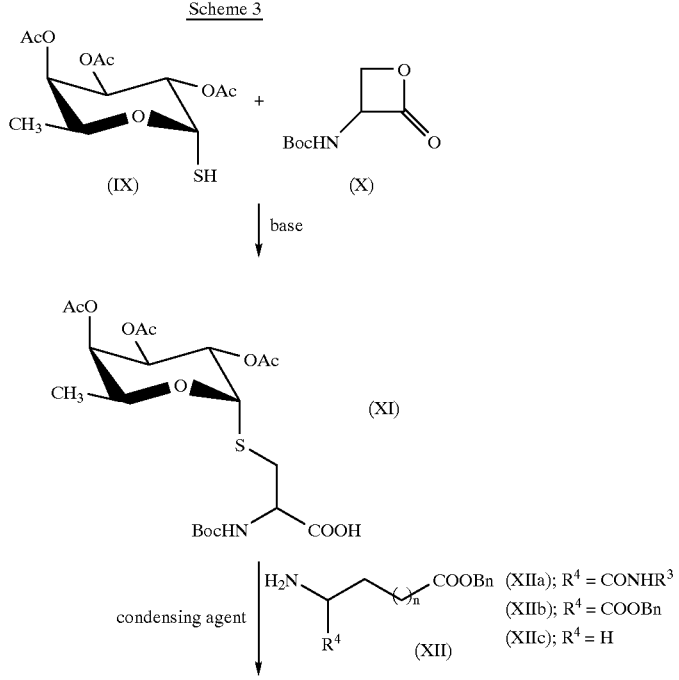

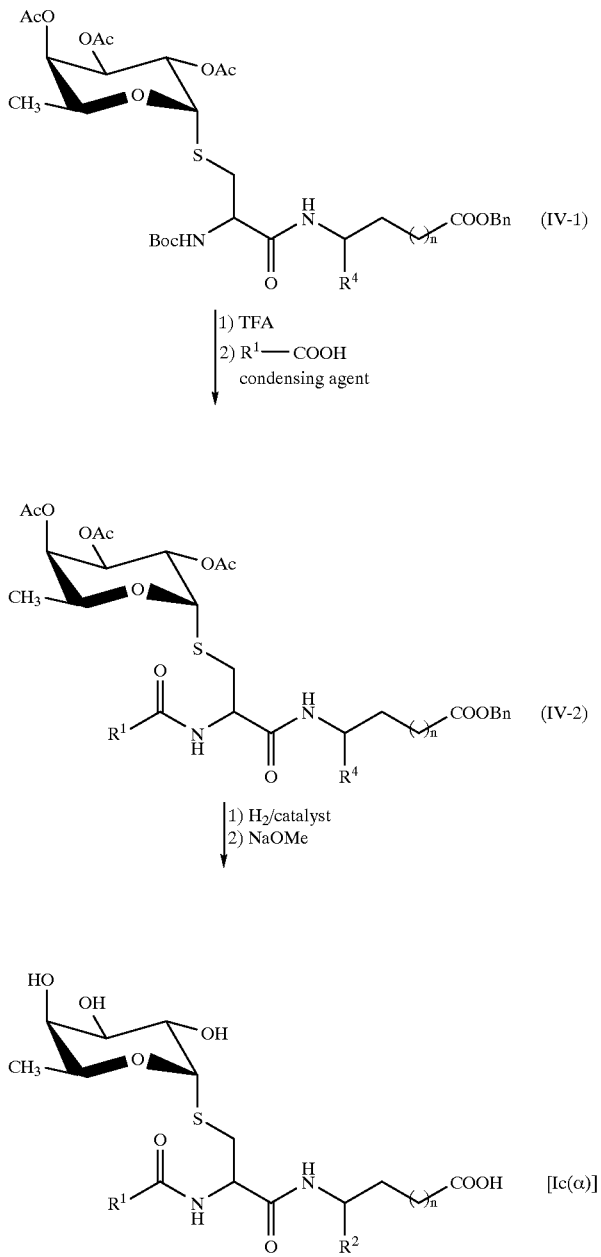

wherein $R^1$, $R^2$, $R^3$, $R^4$ and n are the same as defined above.

First, the intermediate (XI) is obtained from the known compound (IX) (cf., Tetrahedron: Asymmetry Vol. 5, No. 12, 2351–2366 (1994)) and the known compound (X) (cf., Journal of the American Chemical Society, 107, 7105–7109 (1985)). That is, for example, the compound (IX) and the compound (X) are reacted in an inert solvent (e.g., DMF, etc.) in the presence of a base (e.g., NaH, etc.) at a temperature of 0° C. to room temperature, for 0.5 to 3 hours, to give the compound (XI).

The compound (XI) and the compound (XII) are condensed with using a condensing agent to give the compound (IV-1). The condensing agent includes, for example, DCC, WSC, etc., and the condensation reaction is usually carried out, if necessary, in the presence of a condensation promoter (e.g., HOBt, etc.), at a temperature of 0° C. to room temperature for 2 to 24 hours. The compound (XII), the condensing agent and the condensation promoter are used in an amount of 0.8–1.2 mole, 1.0–1.5 mole, and 1.0–1.5 mole, respectively, to 1 mole of the compound (XI).

Alternatively, the condensation reaction is carried out by a mixed acid anhydride method as mentioned below, in addition to the above method with using a condensing agent. That is, the compound (XI) is dissolved in an aprotic solvent (e.g., THF, DMF, etc.), and thereto is added a tertiary amine (e.g., TEA, N-methylmorpholine, etc.) in an equimolar amount, and further thereto are added at a temperature of −20° C. to 5° C. a chlorocarbonate ester (e.g., ethyl chloroformate, etc.), or an acid chloride (e.g., pivaloyl chloride, etc.) to give a mixed acid anhydride. Then, to the mixture is added the above compound (XII), and the mixture is reacted at a temperature of 0° C. to room temperature for 2 to 24 hours to give the compound (IV-1).

The Boc-group of the compound (IV-1) is removed. The reaction is carried out by stirring in a solvent (e.g., methylene chloride, etc.), or without a solvent, in the presence of TFA in an amount of 10 equivalents or more, at a temperature of 0° C. to room temperature, for 0.5 to 3 hours. After the reaction is completely over, the TFA (and solvent) is removed by distillation under reduced pressure. The resultant is neutralized with a base such as sodium hydrogen carbonate or TEA, etc., and used immediately in the subsequent reaction. That is, immediately after the cleavage of the Boc-group, the resultant is condensed with a carboxylic acid ($R^1$—COOH) in an inert solvent (e.g., DMF, etc.) with using a condensing agent to give the compound (IV-2).

Finally, the compound (IV-2) is subjected to hydrogenolysis to remove the benzyl group, and then the acetyl groups are removed to give the desired compound [Ic(αc)]. The hydrogenolysis is carried out in ethanol or 1,4-dioxane with adding thereto water, hydrochloric acid, acetic acid, etc., in the presence of a catalyst such as 10% palladium-carbon, 20% palladium hydroxide-carbon, platinum, etc., under hydrogen atmosphere or hydrogen pressure at a temperature of room temperature to 60° C., for 2 to 10 hours. The removal of the acetyl groups is usually carried out by stirring the mixture in a lower alcohol (e.g., methanol, ethanol, etc.) with using a 28% NaOMe/methanol solution at room temperature for 0.5 to 1.5 hour.

(3-2) Preparation of β-anomer [Ic(β)] of the compound (Ic):

The β-anomer [Ic(β)] is prepared in the same manner as in the process for preparing the compound [Ia(β)] in the above Scheme 2a, as shown in the following Scheme 2b.

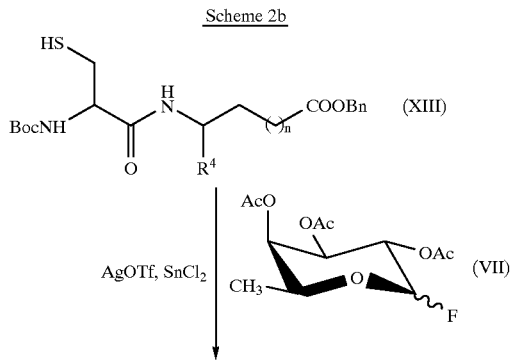

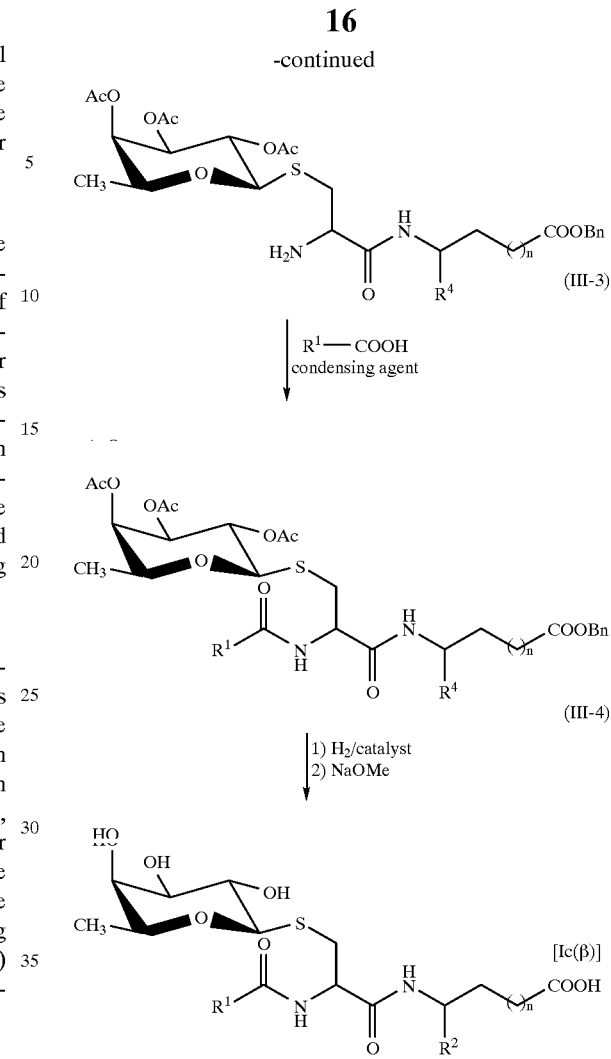

wherein $R^1$, $R^2$, $R^4$ and n are the same as defined above.

First, the compound (XIII) is glycosylated with using the glycosyl donor (VII) [cf., Carbohydrate Research, 200, 391–402 (1990)]. That is, the compound (XIII) and the glycosyl donor (VII) are reacted in a solvent (e.g., methylene chloride, etc.) in the presence of AgOTf and $SnCl_2$, to selectively give the compound (III-3).

The compound (III-3) is condensed with a carboxylic acid ($R^1$—COOH) with using a condensing agent in an inert solvent (e.g., DMF, etc.), to give the compound (III-4). The condensing agent includes, for example, DCC or WSC, and the condensation reaction is preferably carried out by stirring the reaction mixture, if necessary, in the presence of a condensation promoter (e.g., HOBt, etc.) at a temperature of 0° C. to room temperature, for 2 to 24 hours. The carboxylic acid, the condensing agent and the condensation promoter are used in an amount of 0.8 to 1.2 mole, 1.0 to 1.5 mole, and 1.0 to 1.5 mole, respectively, to 1 mole of the compound (III-3).

Finally, the compound (III-4) is subjected to hydrogenolysis to remove the benzyl group, and then, the acetyl groups thereof are removed to give the desired compound [Ic(β)]. The hydrogenolysis is carried out in ethanol or 1,4-dioxane with adding thereto water, hydrochloric acid, acetic acid, etc., in the presence of a catalyst such as 10% palladium-carbon, 20% palladium hydroxide-carbon, platinum, etc., under hydrogen atmosphere or hydrogen pressure at a temperature of room temperature to 60° C. The removal of the acetyl groups is usually carried out by stirring the mixture in a lower alcohol (e.g., methanol, ethanol, etc.) with using a 28% NaOMe/methanol solution at room temperature for 0.5 to 1.5 hour.

The present compounds (Ia), (Ib) and (Ic) thus obtained can be converted into a pharmaceutically acceptable salt thereof by a conventional method.

The starting compounds used in the above processes (1) to (3) are prepared as follows.

(1) Process for preparing the compound (V) (the starting compound in Schemes 1a, 1b, 2a):

(1-1) Compound (Va) (the compound of the formula (V) wherein $R^4$ is —$CONHR^3$):

The compound (Va) is prepared, for example, by the following scheme 4.

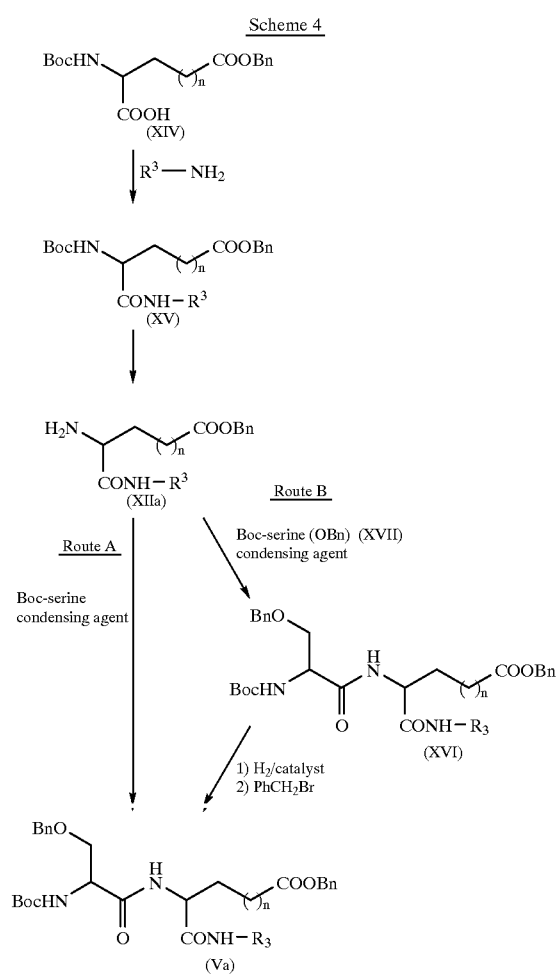

wherein $R^3$ and n are the same as defined above.

First, the compound (XIV) and a lower alkylamine or aniline are condensed to give the compound (XV). The condensation reaction is carried out by using a condensing agent as mentioned above, or by the mixed acid anhydride method as mentioned below.

That is, the compound (XIV) is dissolved in an aprotic solvent (e.g., THF, DMF, etc.), and thereto is added an equivalent of a tertiary amine (e.g., TEA, N-methylmorpholine, etc.), and further thereto are added a chlorocarbonate ester (e.g., ethyl chloroformate, etc.), or an acid chloride (e.g., pivaloyl chloride, etc.) at a temperature of −20 to 5° C., to give a mixed acid anhydride. Then, to the reaction mixture is added a lower alkylamine or aniline, and the mixture is reacted at a temperature of 0° C. to room temperature for 2 to 24 hours, to give the compound (XV).

In the same manner as above, the Boc-group of the compound (XV) is removed with using TFA to give the compound (XIIa), which is condensed with Boc-serine with using the above mentioned condensing agent (e.g., DCC, WSC, etc.) to give the compound (Va) (Route A).

Alternatively, the compound (XIIa) and the serine derivative (XVII) are condensed by the method using a condensing agent, or by the mixed acid anhydride method. The resulting compound (XVI) is subjected to hydrogenolysis, and the resultant is reacted with benzyl bromide in the presence of a base to give the compound (Va) (Route B). The hydrogenolysis is carried out in the same manner as in the preparation of the compound (Ia) from the compound (II-2) in the above mentioned Scheme 1a. The reaction of the product thus obtained and benzyl bromide is carried out by stirring the reaction mixture in an aprotic polar solvent (e.g., DMF, etc.) in the presence of TEA or sodium hydrogen carbonate, at a temperature of 0° C. to room temperature, for 3 to 24 hours.

In Scheme 4, the indication of the stereochemical positions is omitted, however, the stereoisomer of the compound (Va) can be obtained by using the optically active compound (XIV), and the optically active Boc-serine or the optically active compound (XVII).

(1-2) Compound (Vb) (the compound of the formula (V) wherein $R^4$ is a benzyloxycarbonyl group):

The compound (Vb) is prepared, for example, by the following scheme 5.

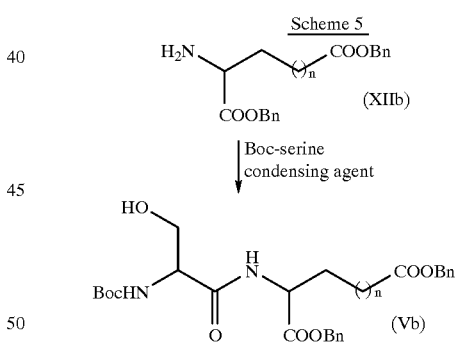

wherein n is the same as defined above.

That is, to the known compound (XIIb) or a salt thereof is added, if necessary, an equimolar amount of a base (e.g., TEA, etc.) to neutralize, and the mixture is subjected to condensation reaction with Boc-serine with using a condensing agent (e.g., DCC, WSC, etc.), to give the compound (Vb).

The stereoisomer of the compound (Vb) is readily obtained by the condensation reaction of the optically active compound (XIIb) with Boc-Ser or Boc-D-Ser.

(1-3) Compound (Vc) (the compound of the formula (V) wherein $R^4$ is a hydrogen atom):

The compound (Vc) is prepared, for example, by the following scheme 6.

Scheme 6

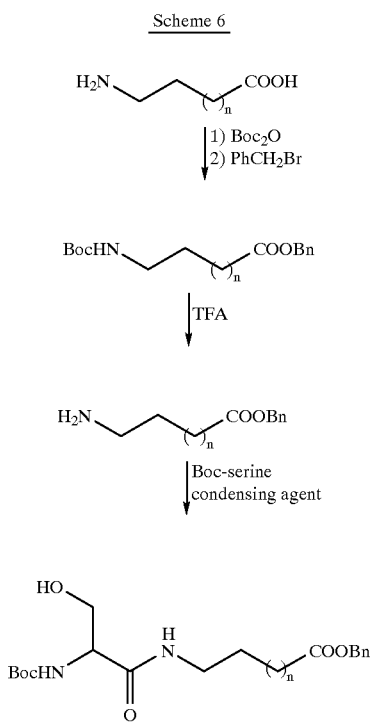

wherein n is the same as defined above.

That is, the amino group of the known compound (XVIII) is converted into Boc-amino group by a conventional method, and the carboxyl group thereof is esterified with a benzyl group to give the compound (XIX). Subsequently, the Boc-group of the compound (XIX) is removed in the same manner as in the preparation of the compound (Va) to give the compound (XX), which is condensed with Boc-serine to give the compound (Vc).

The stereoisomer of the compound (Vc) is readily obtained by using an optically active Boc-serine.

(2) Preparation of the compound (XIII) (the starting compound in Scheme 2b):

The compound (XIII) is prepared, for example, by the following scheme 7.

Scheme 7

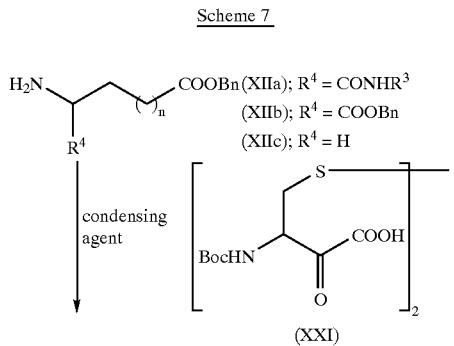

wherein $R^3$, $R^4$ and n are the same as defined above.

First, the Boc-cystine (XXI) and the amino compound (XII) are condensed with using a condensing agent (e.g., DCC, WSC, etc.) as mentioned above, to give the compound (XXII). Then, the disulfide bond of the compound (XXII) is cleaved off by reduction to give the compound (XIII). The reaction is usually carried out by stirring the reaction mixture in a lower alcohol (e.g., methanol, ethanol, etc.), and if necessary, by adding thereto water, in the presence of n-Bu$_3$P at a temperature of 0° C. to room temperature, for 0.5 to 2 hours.

The stereoisomer of the compound (XIII) is obtained by reacting a stereoisomer of the amino compound (XIIa) or (XIIb), and the optically active Boc-cystine (XXI).

The drug containing as an active ingredient the fucose derivative (I) of the present invention or a pharmaceutically acceptable salt thereof can be administered to patients either orally or parenterally. The dosage of the drug may vary depending on the administration routes, ages, weights or conditions of the patients, but it is usually in the range of 0.1–600 mg/day of the fucose derivative (I), which is administered once a day or divided into 2 to 4 dosage units.

The pharmaceutical preparations for oral administration may be tablets, granules, fine particles, capsules. Tablets, granules, and fine particles may be prepared by a conventional method by mixing the fucose derivative (I) of the present invention, or a pharmaceutically acceptable salt thereof, and conventional pharmaceutically acceptable diluents or carriers such as vehicles (e.g., lactose, synthetic aluminum silicate, glucose, mannitol, crystalline cellulose, starch, etc.), disintegrators (e.g., carboxymethylcellulose, sodium alginate, etc.), lubricants (e.g., magnesium stearate, talc, etc.), or binders (e.g., hydroxymethyl-cellulose, hydroxypropyl methylcellulose, polypyrrolidone, etc.), and capsules are formulated by filling the above prepared granules, powders into capsules.

Injection preparations are prepared by dissolving or suspending the fucose derivative (I) of the present invention or a pharmaceutically acceptable salt thereof in sterile distilled water, and adding thereto an isotonic agent such as mannitol, sodium chloride, glucose, sorbitol, glycerol, xylitol, fructose, maltose, mannose, etc., and if necessary, further adding thereto a stabilizer such as sodium sulfite, albumin, etc., or a preservative such as benzyl alcohol, etc., and putting the resultant into ampules or vials aseptically.

The compound (I) of the present invention or a pharmaceutically acceptable salt thereof strongly inhibits the binding of E-selectin, P-selectin and/or L-selectin to sialyl Le$^x$ (Experiments 1, 2), and inhibit ear swelling and cell infiltration in inflammatory animal models (Experiments 3 to 5). Moreover, the compound (I) of the present invention or a salt thereof show low toxicity. For example, the compound c of the present invention [N-(2-tetradecylhexadecanoyl)-O-(α-L-fucofuranosyl)-D-seryl]-L-glutamic acid 1-methylamide (the compound of Example 19) (1000 mg/kg) was orally administered to mice, and the mice were observed for one week thereafter, during which no significant change was observed. Therefore, the compound (I) of the present invention or a salt thereof is useful as a medicament.

Experiment 1

Inhibitory test on the binding of P-selectin to sialyl Le$^x$:
(1) Test Compounds:
The present compound a
  [N-(2-tetradecylhexadecanoyl)-O-(α-L-fucofuranosyl)-L-seryl]-L-glutamic acid 1-methylamide (the compound of Example 17)
The present compound b
  [N-(2-tetradecylhexadecanoyl)-O-(α-L-fucofuranosyl)-L-seryl]-D-glutamic acid 1-methylamide (the compound of Example 18)
The present compound c
  [N-(2-tetradecylhexadecanoyl)-O-(α-L-fucofuranosyl)-D-seryl]-L-glutamic acid 1-methylamide (the compound of Example 19)
The present compound d
  [N-(2-tetradecylhexadecanoyl)-O-(α-L-fucofuranosyl)-D-seryl]-D-glutamic acid 1-methylamide (the compound of Example 20)
The present compound e
  4-N-[N-(2-tetradecylhexadecanoyl)-O-(α-L-fucofuranosyl)-L-seryl]aminobutyric acid (the compound of Example 23)
The present compound f
  5-N-[N-(2-tetradecylhexadecanoyl)-O-(α-L-fucofuranosyl)-L-seryl]aminovaleric acid (the compound of Example 24)
The present compound g
  [N-(2-tetradecylhexadecanoyl)-O-(α-L-fucofuranosyl)-L-seryl]-D-glutamic acid 1-anilide (the compound of Example 27)
The present compound h
  [N-(2-tetradecylhexadecanoyl)-O-(α-L-fucofuranosyl)-L-seryl]-D-glutamic acid 1-methylamide sodium salt (the compound of Example 28)
The present compound i
  [N-(2-tetradecylhexadecanoyl)-O-(α-L-fucopyranosyl)-L-seryl]-L-glutamic acid 1-methylamide (the compound of Example 45)
The present compound j
  [N-(2-tetradecylhexadecanoyl)-O-(α-L-fucopyranosyl)-L-seryl]-D-glutamic acid 1-methylamide (the compound of Example 46)
The present compound k
  [N-(2-tetradecylhexadecanoyl)-O-(α-L-fucopyranosyl)-D-seryl]-L-glutamic acid 1-methylamide (the compound of Example 47)
The present compound l
  [N-(2-tetradecylhexadecanoyl)-O-(α-L-fucopyranosyl)-D-seryl]-D-glutamic acid 1-methylamide (the compound of Example 48)
The present compound m
  [N-(2-tetradecylhexadecanoyl)-O-(β-L-fucopyranosyl)-L-seryl]-L-glutamic acid 1-methylamide (the compound of Example 57)
The present compound n
  [N-(2-tetradecylhexadecanoyl)-O-(β-L-fucopyranosyl)-L-seryl]-D-glutamic acid 1-methylamide (the compound of Example 58)
The present compound o
  [N-(2-tetradecylhexadecanoyl)-O-(β-L-fucopyranosyl)-D-seryl]-L-glutamic acid 1-methylamide (the compound of Example 59)
The present compound p
  [N-(2-tetradecylhexadecanoyl)-O-(β-L-fucopyranosyl)-D-seryl]-D-glutamic acid 1-methylamide (the compound of Example 60)
The present compound q
  [N-(2-tetradecylhexadecanoyl)-S-(α-L-fucopyranosyl)-L-cysteinyl]-L-glutamic acid 1-methylamide (the compound of Example 69)
The present compound r
  [N-(2-tetradecylhexadecanoyl)-S-(α-L-fucopyranosyl)-L-cysteinyl]-D-glutamic acid 1-methylamide (the compound of Example 70)
The present compound s
  [N-(2-tetradecylhexadecanoyl)-S-(α-L-fucopyranosyl)-D-cysteinyl]-L-glutamic acid 1-methylamide (the compound of Example 71)
The present compound t
  [N-(2-tetradecylhexadecanoyl)-S-(α-L-fucopyranosyl)-D-cysteinyl]-D-glutamic acid 1-methylamide (the compound of Example 72)
The present compound u
  [N-(2-tetradecylhexadecanoyl)-S-(β-L-fucopyranosyl)-L-cysteinyl]-D-glutamic acid 1-methylamide (the compound of Example 75)
Known compound X
Sialyl Le$^x$ (Positive control compound)
(2) Test Method:
The experiment was carried out according to the method using selectin-IgG chimera, which was reported by Foxall, C. et al. (J. Cell Biol., 117, 895–902 (1992)).

Sialyl Le$^x$-pentaceramide was dissolved in 50% methanol in distilled water, and the solution was put into a 96-well plate in an amount of 100 pmol/well. The plate was allowed to stand at room temperature overnight, and the solvent therein was evaporated. The plate was washed with distilled water, and subjected to blocking with 50 mM imidazole buffer (pH 7.2) containing 5% BSA (bovine serum albumin) and 1 mM calcium chloride at room temperature for one hour.

Separately, to 500-fold diluted solution of each biotinylated anti-human IgG Fc and streptavidin-alkaline phosphatase conjugate with a 50 mM imidazole buffer (pH 7.2) containing 1% BSA and 1 mM calcium chloride, P-selectin IgG chimera was added to give a final concentration of 40 μg/ml, and the mixture was incubated at room temperature for 30 minutes to give the complex solution.

A test compound was dissolved in DMSO (except that the test compound h was dissolved in distilled water) to give 10 mM aqueous solution thereof, which was serially diluted with 50 mM imidazole buffer (pH 7.2) containing 1% BSA and 1 mM calcium chloride to give the solutions in 8 various concentrations (two-fold serial dilution from 20 μM). The test compound solution in each concentration and the above complex solution were mixed in equal volume, and the mixture was incubated at room temperature for 30 minutes to give the reaction solution.

After the blocking was completed, the blocking solution in the above plate was discarded, and the plate was washed with 50 mM imidazole buffer (pH 7.2), and thereto was added the above reaction solution in an amount of 50 μl/well. The plate was incubated at 37° C. for 45 minutes, and then washed three times with 50 mM imidazole buffer (pH 7.2) and washed three times with distilled water. 1M diethanolamine (pH 9.8) containing 0.01% magnesium chloride and 1 mg/ml p-nitrophenyl phosphate was put into each well in an amount of 50 μl/well, and the plate was allowed to stand for 1 to 2 hours for color development. The absorbance at 405 nm was measured, and the binding rate (%) was calculated by the following equation, based on the absorbance (X) of the wells containing a test compound at various concentrations and the absorbance (A) of the wells containing no test compound.

Binding Rate (%)=$X/A \times 100$ $IC_{50}$ was evaluated by probit method from the binding rate.
(3) Test Results:
The results of this experiment are shown in the following Table 1 together with the results of Experiment 2.

Experiment 2

Inhibitory test on the binding of L-selectin to sialyl $Le^x$:
(1) Test Compounds:
The same compounds were used as those in Experiment 1.
(2) Test Method:
The same procedures of Experiment 1 were repeated except that L-selectin IgG chimera (40 μg/ml) was used instead of P-selectin IgG chimera (40 μg/ml).
(3) Test Results:
The results are shown in Table 1 together with the results of Experiment 1.

TABLE 1

| Test Compound | $IC_{50}$ (μM) | |
|---|---|---|
| | P-selectin | L-selectin |
| The present compound a | 1.3 | 2.2 |
| The present compound b | 1.0 | 1.5 |
| The present compound c | 0.3 | 0.5 |
| The present compound d | 0.2 | 0.5 |
| The present compound e | 0.5 | 1.8 |
| The present compound f | 1.2 | 2.5 |
| The present compound g | 0.1 | 1.7 |
| The present compound h | 1.2 | 0.3 |
| The present compound i | 1.9 | 39 |
| The present compound j | 0.5 | 6.0 |
| The present compound k | 0.7 | 9.4 |
| The present compound l | 2.1 | 18 |
| The present compound m | 0.6 | 0.8 |
| The present compound n | 0.3 | 0.8 |
| The present compound o | 0.3 | 1.6 |
| The present compound p | 0.3 | 0.7 |
| The present compound q | 0.1 | 0.2 |
| The present compound r | 0.2 | 0.7 |
| The present compound s | 0.1 | 0.1 |
| The present compound t | 0.3 | 0.6 |
| The present compound u | 1 | 1 |
| Known compound X | >500 | >500 |

Experiment 3

Inhibitory effects on ear swelling:
(1) Test Compound:
The present compound c:
[N-(2-tetradecylhexanoyl)-O-(α-L-fucofuranosyl)-D-seryl]-L-glutamic acid 1-methylamide (the compound of Example 19)

(2) Test method:
Female BALB/c mice (6-weeks old) were sensitized by intraperitoneal injection of saline (0.5 ml) containing ovalbumin (3 μl) and aluminum hydroxide gel (4 mg). Two weeks after the sensitization, a 1 mg/ml solution of ovalbumin in phosphate buffered saline (10 μl) was subcutaneously injected to the mice at both of the ears to induce the inflammatory response. In the non-inflammation group, phosphate buffered saline was subcutaneously injected to the sensitized mice instead.

The test compound was dissolved in 0.01N-NaOH-saline so as to be a concentration of 1 mg/ml, and the solution was diluted with saline. The test compound solution thus prepared was injected to the mice at the tail vein, at 2, 5 and 8 hours after the induction of inflammatory response, in a dosage volume of 0.1 ml/10 g of body weight (the treated group). In the control group, saline only was injected to the mice.

Twenty-four hours after the induction of inflammatory response, both of the ears were cut to collect a piece of 6 mm diameter, and the weight thereof was measured. The ear weight per area was used as an index for ear swelling. The inhibitory rate on ear swelling was calculated by the following equation.

$$\text{Swelling inhibitory rate } (\%) = \frac{Wcont - Wexp}{Wcont - Wnega} \times 100$$

Wexp: Average ear weight in the treated group
Wnega: Average ear weight in the non-inflammation group
Wcont: Average ear weight in the control group
(3) Test Results:
The results are shown in Table 2.

TABLE 2

| Dosage of the present compound c (mg/kg) | Ear swelling inhibitory rate (%) |
|---|---|
| 0.1 | 45 |
| 1 | 59 |
| 10 | 86 |

Experiment 4

Inhibitory effects on cell infiltration:
(1) Test Compound:
The present compound c:
[N-(2-tetradecylhexanoyl)-O-(α-L-fucofuranosyl)-D-seryl]-L-glutamic acid 1-methylamide (the compound of Example 19)
(2) Test Method:
According to the report by Bradley, P. P. et al, (cf., Journal of Investigative Dermatology, 78, 206–209 (1982)), the activity of myeloperoxidase (hereinafter, referred to as MPO) in the tissue was used as an index for cell infiltration.

The ear tissue, the weight of which was measured in Experiment 3, was homogenized, and centrifuged. The MPO activity in the supernatant was measured by using the absorbance at 450 nm (hereinafter, referred to as OD) of o-dianisidine as an index, according to the method of Bradley, et al. (see the above reference).

The inhibitory rate on cell infiltration was calculated by the following equation.

$$\text{Cell infiltration inhibitory rate (\%)} = \frac{ODcont - ODexp}{ODcont - ODnega} \times 100$$

ODexp: Average OD in the treated group
ODnega: Average OD in the non-inflammatory group
ODcont: Average OD in the control group
(3) Test Results:
The results are shown in Table 3.

TABLE 3

| Dosage of the present compound c (mg/kg) | Cell infiltration inhibitory rate (%) |
|---|---|
| 0.1 | 19 |
| 1 | 34 |
| 10 | 64 |

Experiment 5

Inhibitory effects on the peritoneal inflammation induced by thioglycollate:
(1) Test Compounds:
The present compound c:
[N-(2-tetradecylhexadecanoyl)-O-(α-L-fucofuranosyl)-D-seryl]-L-glutamic acid 1-methylamide (the compound of Example 19)
The present compound k:
[N-(2-tetradecylhexadecanoyl)-O-(α-L-fucopyranosyl)-D-seryl]-L-glutamic acid 1-methylamide (the compound of Example 47)
(2) Test Method:
Male BALB/C mice (11-weeks old) were peritoneally injected with 3% thioglycollate medium (1 ml) to induce the inflammation. In the non-inflammation group, saline was peritoneally injected to the mice. Two hours thereafter, the mice were killed with breeding, and the peritoneal cavity was washed with a phosphate buffered saline containing 0.1% BSA, 0.5 mM EDTA, 10 U/ml heparin to collect the exudate cells. The red blood cells were lysed, and the exudate cells were lysed in 50 mM potassium phosphate buffer containing 0.5% hexadecyltrimethylammonium bromide. The MPO activity in the supernatant was measured according to the Bradley's method (see the above reference).

The test compound was dissolved in 0.0012M arginine-containing saline solution so as to be a concentration of 1 mg/ml. The test compound solution was injected to the mice at the tail vein in a dosage volume of 0.1 ml/10 g of the body weight, at just before and one hour after the induction of inflammation response (the treated group). In the control group, saline solution was injected to the mice.

The cell infiltration inhibitory rate was calculated in the same manner as in Experiment 4, by the equation 3.
(3) Test Results:
The results are shown in Table 4.

TABLE 4

| Test compound | Dosage (mg/kg) | Cell infiltration inhibitory rate (%) |
|---|---|---|
| The present compound c | 10 | 64 |
| The present compound k | 10 | 37 |

As is shown in the above results, the present compounds strongly inhibit the binding of P-selectin and L-selectin to sialyl Le$^x$, and it is also apparent that the present compounds inhibit ear swelling and cell infiltration in the inflammatory animal models. Therefore, the present compounds are useful as selectin inhibitor, and can be used in the prophylaxis or treatment of various inflammations, for example, inflammatory dermatitides such as atopic dermatitis, contact hypersensitivity and photosensitivity, autoimmune chronic diseases such as rheumatoid arthritis and chronic thyroiditis and ischemia-reperfusion injury.

EXAMPLES

The present invention will be illustrated in more detail by the following Reference Examples and Examples.

Reference Example 1

Preparation of N-tert-butoxycarbonyl-L-seryl-L-glutamic acid 1-methyl-amide 5-benzyl ester [stereoisomer of the compound (Va) wherein $R^3$ is methyl group, and n is 1]:
(1) N-tert-butoxycarbonyl-L-glutamic acid 1-methylamide 5-benzyl ester [S-isomer of the compound (XV) wherein $R^3$ is methyl group, and n is 1]:

To a solution of N-tert-butoxycarbonyl-L-glutamic acid 5-benzyl ester (10.0 g) in THF (100 ml) is added TEA (3.9 g), and further thereto is added with stirring ethyl chlorocarbonate (4.2 g) under ice-cooling, and the mixture is stirred for two minutes. To the mixture is added a 40% solution of methylamine in methanol (6.9 g), and the mixture is stirred for two hours while it is gradually warmed to room temperature. Ethyl acetate (200 ml) is added to the reaction mixture, and the mixture is washed successively with 1N hydrochloric acid, a saturated aqueous sodium hydrogen carbonate solution, and a saturated aqueous sodium chloride solution, dried, and concentrated under reduced pressure. The precipitated solid was collected by filtration, and washed with ether to give N-tert-butoxycarbonyl-L-glutamic acid 1-methylamide 5-benzyl ester (9.3 g) as colorless crystals.

M.p. 124–125° C.; $^1$H-NMR (DMSO-d$_6$)δ: 1.37 (s, 9H), 1.66–1.82 (m, 1H), 1.83–2.00 (m, 1H), 2.35 (t, 2H, J=7.6 Hz), 2.57 (d, 3H, J=4.5 Hz), 3.83–3.95 (m, 1H), 5.08 (s, 2H), 6.90 (d, 1H, J=8.2 Hz), 7.25–7.45 (m, 5H), 7.76 (d, 1H, J=4.6 Hz).

(2) N-tert-butoxycarbonyl-L-seryl-L-glutamic acid 1-methylamide 5-benzyl ester:

To a solution of the compound obtained in the above (1) (8.5 g) in methylene chloride (50 ml) is added with stirring TFA (50 ml) under ice-cooling, and the mixture is stirred for one hour. The mixture is concentrated under reduced pressure, and the resulting syrup is dissolved in chloroform (100 ml). The mixture is washed with a saturated aqueous sodium hydrogen carbonate solution, dried, and concentrated under reduced pressure to give a de-protected compound as a syrup. The syrup thus obtained is dissolved in DMF (110 ml), and thereto is added Boc-Ser (5.0 g), and further thereto are added with stirring WSC (6.0 g) and HOBt (4.3 g) under ice-cooling, and the mixture is stirred at room temperature for 18 hours. To the reaction mixture is added chloroform (200 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (chloroform:MeOH=50:1→9:1) to give the title stereoisomer (6.0 g) as colorless crystals.

M.p. 110–113° C.; $^1$H-NMR (DMSO-d$_6$)δ: 1.37 (s, 9H), 1.68–1.86 (m, 1H), 1.90–2.11 (m, 1H), 2.30–2.45 (m, 2H), 2.56 (d, 3H, J=4.6 Hz), 3.55 (t, 2H, J=5.4 Hz), 3.90–4.15 (m, 1H), 4.20–4.35 (m, 1H), 4.98 (t, 1H, J=5.4 Hz), 5.10 (s, 2H), 6.79 (d, 1H, J=7.5 Hz), 7.25–7.45 (m, 5H), 7.78 (d, 1H, J=4.6 Hz), 7.96 (d, 1H, J=8.5 Hz).

Reference Example 2

Preparation of N-tert-butoxycarbonyl-L-seryl-D-glutamic acid 1-methylamide 5-benzyl ester [stereoisomer of the compound (Va) wherein $R^3$ is methyl group, and n is 1]:
(1) N-tert-butoxycarbonyl-D-glutamic acid 1-methylamide 5-benzyl ester [R-isomer of the compound (XV) wherein $R^3$ is methyl group, and n is 1]:

To a solution of N-tert-butoxycarbonyl-D-glutamic acid 5-benzyl ester (5.0 g) in THF (50 ml) is added TEA (1.9 g), and further thereto is added with stirring ethyl chlorocarbonate (2.1 g) under ice-cooling, and the mixture is stirred for two minutes. To the mixture is added a 40% solution of methylamine in methanol (2.9 g), and the mixture is stirred for two hours while it is gradually warmed to room temperature. Ethyl acetate (150 ml) is added to the reaction mixture, and the mixture is washed successively with 1N hydrochloric acid, a saturated aqueous sodium hydrogen carbonate solution, and a saturated aqueous sodium chloride solution, dried, and concentrated under reduced pressure. The precipitated solid was collected by filtration, and washed with ether to give N-tert-butoxycarbonyl-D-glutamic acid 1-methylamide 5-benzyl ester (4.5 g) as colorless crystals.

M.p. 120–123° C.; $^1$H-NMR (DMSO-$d_6$)δ: 1.37 (s, 9H), 1.65–1.82 (m, 1H), 1.83–2.00 (m, 1H), 2.36 (t, 2H, J=7.7 Hz), 2.57 (d, 3H, J=4.5 Hz), 3.82–3.98 (m, 1H), 5.08 (s, 2H), 6.90 (d, 1H, J=8.2 Hz), 7.25–7.45 (m, 5H), 7.76 (d, 1H, J=4.5 Hz).

(2) (N-tert-butoxycarbonyl-L-seryl)-D-glutamic acid 1-methylamide 5-benzyl ester:

To a solution of the compound obtained in the above (1) (4.0 g) in methylene chloride (40 ml) is added with stirring TFA (40 ml) under ice-cooling, and the mixture is stirred for one hour. The mixture is concentrated under reduced pressure, and the resulting syrup is dissolved in chloroform (80 ml). The mixture is washed with a saturated aqueous sodium hydrogen carbonate solution, dried, and concentrated under reduced pressure to give the de-protected compound as a syrup. Boc-Ser (1.4 g) is dissolved in THF (60 ml), and thereto is added TEA (0.9 g), and further thereto is added with stirring ethyl chlorocarbonate (0.95 g) under ice-cooling. The mixture is stirred for two minutes, and thereto is added a solution of the syrup obtained above (1.7 g) in THF (10 ml), and the mixture is stirred for three hours. To the reaction mixture is added ethyl acetate (140 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (chloroform:MeOH=20:1→10:1) to give the title stereoisomer (0.8 g) as colorless crystals.

M.p. 124–127° C.; $^1$H-NMR (DMSO-$d_6$)δ: 1.38 (s, 9H), 1.66–1.88 (m, 1H), 1.92–2.12 (m, 1H), 2.30–2.42 (m, 2H), 2.57 (d, 3H, J=4.6 Hz), 3.54 (t, 2H, J=5.6 Hz), 3.86–4.00 (m, 1H), 4.13–4.30 (m, 1H), 4.88 (t, 1H, J=5.7 Hz), 5.07 (s, 2H), 6.82 (d, 1H, J=6.9 Hz), 7.30–7.45 (m, 5H), 7.77 (d, 1H, J=4.5 Hz), 8.03 (d, 1H, J=8.1 Hz).

Reference Example 3

Preparation of N-tert-butoxycarbonyl-D-seryl-L-glutamic acid 1-methyl-amide 5-benzyl ester [stereoisomer of the compound (Va) wherein $R^3$ is methyl group, and n is 1]:

(1) N-tert-butoxycarbonyl-O-benzyl-D-seryl-L-glutamic acid 1-methylamide 5-benzyl ester [stereoisomer of the compound (XVI) wherein $R^3$ is methyl group, and n is 1]:

To a solution of N-tert-butoxycarbonyl-L-glutamic acid 1-methylamide 5-benzyl ester (3.2 g, Reference Example 1-(1)) in methylene chloride (25 ml) is added with stirring TFA (25 ml) under ice-cooling, and the mixture is stirred for three hours. The mixture is concentrated under reduced pressure, and the resulting syrup is dissolved in chloroform (100 ml), and washed with a saturated aqueous sodium hydrogen carbonate solution. The mixture is dried, and concentrated under reduced pressure to give the de-protected compound as a syrup. The syrup thus obtained is dissolved in DMF (50 ml), and thereto is added Boc-D-Ser(OBn) (2.5 g), and further thereto are added with stirring WSC (2.1 g) and HOBt (1.7 g) under ice-cooling. The mixture is stirred at room temperature for 20 hours. To the reaction mixture is added ethyl acetate (150 ml), and the mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration, and washed with ether to give the stereoisomer (3.6 g) as colorless crystals.

M.p. 106–108° C.; $^1$H-NMR (DMSO-$d_6$)δ: 1.38 (s, 9H), 1.68–1.86 (m, 1H), 1.91–2.12 (m, 1H), 2.23–2.40 (m, 2H), 2.54 (d, 3H, J=4.6 Hz), 3.58 (d, 2H, J=5.9 Hz), 4.05–4.32 (m, 2H), 4.45 (s, 2H), 5.06 (s, 2H), 7.00 (d, 1H, J=6.8 Hz), 7.15–7.43 (m, 10H), 7.71 (d, 1H, J=4.5 Hz), 8.19 (d, 1H, J=8.2 Hz).

(2) N-tert-butoxycarbonyl-D-seryl-L-glutamic acid 1-methylamide 5-benzyl ester:

To a solution of the compound obtained in the above (1) (2.0 g) in ethanol (70 ml) is added 20% Pd(OH)$_2$/C (1.0 g), and the mixture is stirred at 30° C. under hydrogen pressure (3–4 atms) for 25 hours. The catalyst is removed by filtration, and the filtrate is concentrated under reduced pressure to give the de-protected compound (1.4 g) as a syrup. The syrup thus obtained is dissolved in DMF (25 ml), and thereto are added successively TEA (1.2 g), and benzyl bromide (2.1 g), and the mixture is stirred at room temperature for 19 hours. To the reaction mixture is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (chloroform:MeOH= 20:1→9:1) to give the title stereoisomer (0.9 g) as colorless crystals.

M.p. 127–128° C.; $^1$H-NMR (DMSO-$d_6$)δ: 1.38 (s, 9H), 1.65–1.85 (m, 1H), 1.90–2.15 (m, 1H), 2.30–2.40 (m, 2H), 2.58 (d, 3H, J=4.6 Hz), 3.54 (t, 2H, J=5.6 Hz), 3.85–4.00 (m, 1H), 4.13–4.29 (m, 1H), 4.88 (t, 1H, J=5.6 Hz), 5.07 (s, 2H), 6.82 (d, 1H, J=6.9 Hz), 7.30–7.45 (m, 5H), 7.77 (d, 1H, J=4.6 Hz), 8.03 (d, 1H, J=8.3 Hz).

Reference Example 4

Preparation of N-tert-butoxycarbonyl-D-seryl-D-glutamic acid 1-methyl-amide 5-benzyl ester [stereoisomer of the compound (Va) wherein $R^3$ is methyl group, and n is 1]:

(1) (N-tert-butoxycarbonyl-O-benzyl-D-seryl)-D-glutamic acid 1-methyl-amide 5-benzyl ester [stereoisomer of the compound (XVI) wherein $R^3$ is methyl group, and n is 1]:

To a solution of N-tert-butoxycarbonyl-D-glutamic acid 1-methylamide 5-benzyl ester (4.0 g, Reference Example 2-(1)) in methylene chloride (30 ml) is added with stirring TFA (30 ml) under ice-cooling, and the mixture is stirred for 2 hours. The mixture is concentrated under reduced pressure, and the resulting syrup is dissolved in chloroform (100 ml), and washed with a saturated aqueous sodium hydrogen carbonate solution. The mixture is dried, and concentrated under reduced pressure to give the de-protected compound as a syrup. The syrup thus obtained is dissolved in DMF (50 ml), and thereto is added Boc-D-Ser(OBn) (3.3 g), and further thereto are added with stirring WSC (2.7 g) and HOBt (2.2 g) under ice-cooling. The mixture is stirred at room temperature for 17 hours. To the reaction mixture is added ethyl acetate (160 ml), and the mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration, and washed with ether to give the stereoisomer (5.1 g) as colorless crystals.

M.p. 104–118° C.; $^1$H-NMR (DMSO-$d_6$)$\delta$: 1.37 (s, 9H), 1.70–1.88 (m, 1H), 1.88–2.08 (m, 1H), 2.28–2.42 (m, 2H), 3.59 (d, 2H, J=5.5 Hz), 4.10–4.32 (m, 2H), 4.47 (s, 2H), 5.06 (s, 2H), 7.06 (d, 1H, J=7.7 Hz), 7.20–7.45 (m, 10H), 7.69 (d, 1H, J=4.4 Hz), 8.00 (d, 1H, J=8.2 Hz).

(2) N-tert-butoxycarbonyl-D-seryl-D-glutamic acid 1-methylamide 5-benzyl ester:

To a solution of the compound obtained in the above (1) (2.0 g) in ethanol (40 ml) is added 20% Pd(OH)$_2$/C (0.5 g), and the mixture is stirred at 30° C. under hydrogen pressure (3–4 atms) for 6 hours. The catalyst is removed by filtration, and the filtrate is concentrated under reduced pressure to give the de-protected compound (1.3 g) as a syrup. The syrup thus obtained is dissolved in DMF (30 ml), and thereto are added successively TEA (1.0 g), and benzyl bromide (1.5 g), and the mixture is stirred at room temperature for 30 hours. To the reaction mixture is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (chloroform:MeOH=20:1→9:1) to give the title stereoisomer (0.8 g) as colorless crystals.

M.p. 110–112° C.; $^1$H-NMR (DMSO-$d_6$)$\delta$: 1.37 (s, 9H), 1.70–1.85 (m, 1H), 1.90–2.10 (m, 1H), 2.30–2.45 (m, 2H), 2.56 (d, 3H, J=4.5 Hz), 3.55 (t, 2H, J=5.6 Hz), 3.90–4.05 (m, 1H), 4.15–4.30 (m, 1H), 4.99 (t, 1H, J=5.5 Hz), 5.07 (s, 2H), 6.80 (d, 1H, J=7.5 Hz), 7.25–7.45 (m, 5H), 7.78 (d, 1H, J=4.6 Hz), 7.97 (d, 1H, J=8.1 Hz).

Reference Example 5

Preparation of N-tert-butoxycarbonyl-L-seryl-L-aspartic acid 1-methyl-amide 4-benzyl ester [stereoisomer of the compound (Va) wherein $R^3$ is methyl group, and n is 0]:
(1) N-tert-butoxycarbonyl-L-aspartic acid 1-methylamide 4-benzyl ester [S-isomer of the compound (XV) wherein $R^3$ is methyl group, and n is 0]:

To a solution of N-tert-butoxycarbonyl-L-aspartic acid 4-benzyl ester (2.0 g) in THF (20 ml) is added TEA (0.8 g), and thereto is added with stirring ethyl chlorocarbonate (0.9 g) under ice-cooling, and the mixture is stirred for 5 minutes. To the mixture is added a 40% solution of methylamine in methanol (1.2 g), and the mixture is stirred for three hours while it is gradually warmed to room temperature. Ethyl acetate (100 ml) is added to the reaction mixture, and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure chromatography (n-hexane: ethyl acetate=1:1→1:2) to give N-tert-butoxycarbonyl-L-aspartic acid 1-methylamide 4-benzyl ester (1.9 g) as colorless crystals.

$^1$H-NMR (CDCl$_3$)$\delta$: 1.50 (s, 9H), 2.87 (d, 3H, J=5.0 Hz), 2.90–3.10 (m, 2H), 5.22 (s, 2H), 7.45–7.60 (m, 5H).

(2) N-tert-butoxycarbonyl-L-seryl-L-aspartic acid 1-methylamide 4-benzyl ester:

To a solution of the compound obtained in the above (1) (1.8 g) in methylene chloride (20 ml) is added with stirring TFA (20 ml) under ice-cooling, and the mixture is stirred for one hour. The mixture is concentrated under reduced pressure, and the resulting syrup is dissolved in chloroform (100 ml). The mixture is washed with a saturated aqueous sodium hydrogen carbonate solution, dried, and concentrated under reduced pressure to give a de-protected compound as a syrup. The syrup thus obtained is dissolved in DMF (35 ml), and thereto is added Boc-Ser (0.9 g), and further thereto are added with stirring WSC (0.8 g) and HOBt (0.6 g) under ice-cooling, and the mixture is stirred at room temperature for 14 hours. To the reaction mixture is added ethyl acetate (50 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (chloroform alone) to give N-tert-butoxycarbonyl-L-seryl-L-aspartic acid 1-methylamide 4-benzyl ester (0.2 g) as a colorless syrup.

$^1$H-NMR (CDCl$_3$)$\delta$: 1.47 (s, 9H), 2.80–3.10 (m, 2H), 2.94 (d, 3H, J=5.0 Hz), 3.70–4.00 (m, 2H), 4.05–4.60 (m, 2H), 5.15 (s, 2H), 7.30–7.55 (m, 5H).

Reference Example 6

Preparation of 4-N-(N-tert-butoxycarbonyl-L-seryl) aminobutyric acid benzyl ester [S-isomer of the compound (Vc) wherein n is 1]:
(1) 4-N-tert-butoxycarbonylaminobutyric acid benzyl ester [the compound (XIX) wherein n is 1]:

To a solution of 4-aminobutyric acid (2.6 g) in 1,4-dioxane (60 ml) is added water (30 ml), and thereto is added with stirring a solution of 1N sodium hydroxide (100 ml) and Boc$_2$O (6.0 g) in 1,4-dioxane-water (60 ml–30 ml) under ice-cooling. The mixture is stirred at room temperature for 18 hours, and concentrated under reduced pressure. The pH value of the residue is adjusted to pH 3 with citric acid, and the mixture is extracted with ethyl acetate. The extract is washed with water, dried, and concentrated under reduced pressure. The resulting syrup is dissolved in DMF (40 ml), and thereto are added benzyl bromide (12.1 g) and potassium carbonate (6.5 g). The mixture is stirred at room temperature for 15 hours, and thereto is added ethyl acetate (100 ml). The mixture is washed successively with water and a saturated aqueous sodium chloride solution, dried, and concentrated under reduced pressure. The resulting residue is purified by silica gel medium-pressure liquid chromatography (n-hexane alone→n-hexane:ethyl acetate=3:1) to give 4-N-tert-butoxycarbonyl-aminobutyric acid benzyl ester (5.7 g) as colorless crystals.

$^1$H-NMR (CDCl$_3$)$\delta$: 1.43 (s, 9H), 1.70–2.15 (m, 2H), 2.42 (t, 2H, J=6.8 Hz), 3.17 (q, 2H, J=6.8 Hz), 5.15 (s, 2H), 7.40–7.60 (m, 5H).

(2) 4-N-(N-tert-butoxycarbonyl-L-seryl)aminobutyric acid benzyl ester:

To a solution of the compound obtained in the above (0.9 g) in methylene chloride (10 ml) is added with stirring TFA (4 ml) under ice-cooling, and the mixture is stirred for one hour. The mixture is concentrated under reduced pressure, and the resulting syrup is dissolved in chloroform (20 ml). The mixture is washed with a saturated aqueous sodium hydrogen carbonate solution, dried, and concentrated under reduced pressure to give the de-protected compound as a syrup. The syrup thus obtained is dissolved in DMF (10 ml), and thereto is added Boc-Ser (0.6 g), and further thereto is added with stirring WSC (0.5 g) and HOBt (0.4 g) under ice-cooling. The mixture is stirred at room temperature for 17 hours, and thereto is added ethyl acetate (50 ml). The mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give 4-N-(N-tert-butoxycarbonyl-L-seryl)aminobutyric acid benzyl ester (0.3 g) as a colorless syrup.

$^1$H-NMR (CDCl$_3$)δ: 1.43 (s, 9H), 1.70–2.00 (m, 2H), 2.39 (t, 2H, J=7.0 Hz), 3.28 (q, 2H, J=7.0 Hz), 3.70–4.30 (m, 3H), 5.17 (s, 2H), 7.20–7.45 (m, 5H).

Reference Example 7

Preparation of 5-N-(N-tert-butoxycarbonyl-L-seryl)aminovaleric acid benzyl ester [S-isomer of the compound (Vc) wherein n is 2]:

(1) 5-N-tert-butoxycarbonylaminovaleric acid benzyl ester [the compound (XIX) wherein n is 2]:

To a solution of 5-aminovaleric acid (3.6 g) and sodium hydroxide (2.5 g) in water (100 ml) is added with stirring a solution of Boc$_2$O (10.1 g) in 1,4-dioxane (30 ml) under ice-cooling, and the mixture is stirred at room temperature for 3.5 hours. The pH value of the reaction mixture is adjusted to pH 2–3 with conc. hydrochloric acid, and the mixture is extracted twice with chloroform, and then extracted with ethyl acetate. The extract is dried, and concentrated under reduced pressure. The resulting syrup is dissolved in DMF (100 ml), and thereto are added benzyl bromide (15.7 g) and sodium hydrogen carbonate (5.2 g), and the mixture is stirred at room temperature for 20 hours. To the reaction mixture is added chloroform (100 ml), and the mixture is washed successively with water and a saturated aqueous sodium chloride solution, dried, and concentrated under reduced pressure. The resulting residue is purified by silica gel medium-pressure liquid chromatography (n-hexane:ethyl acetate=1:7→1:4) to give 5-N-tert-butoxycarbonylaminovaleric acid benzyl ester (5.3 g) as a colorless syrup.

$^1$H-NMR (CDCl$_3$)δ: 1.58 (s, 9H), 1.50–2.10 (m, 4H), 2.50 (t, 2H, J=6.0 Hz), 3.25 (q, 2H, J=7.2 Hz), 5.21 (s, 2H), 7.30–7.50 (m, 5H).

(2) 5-N-(N-tert-butoxycarbonyl-L-seryl)aminovaleric acid benzyl ester:

To a solution of the compound obtained in the above (1) (1.0 g) in methylene chloride (10 ml) is added with stirring TFA (4 ml) under ice-cooling, and the mixture is stirred for one hour. The mixture is concentrated under reduced pressure, and the resulting syrup is dissolved in DMF (10 ml), and further thereto are added with stirring TEA (1.5 g) and Boc-Ser (0.8 g) under ice-cooling. To the mixture are added with stirring WSC (0.7 g) and HOBt (0.5 g) under ice-cooling, and the mixture is stirred at room temperature for 15 hours. To the reaction mixture is added ethyl acetate (50 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by silica gel medium-pressure liquid chromatography (n-hexane:ethyl acetate= 1:1→ethyl acetate alone) to give 5-N-(N-tert-butoxycarbonyl-L-seryl)aminovaleric acid benzyl ester (1.0 g) as a colorless syrup.

$^1$H-NMR (CDCl$_3$)δ: 1.48 (s, 9H), 1.50–1.90 (m, 4H), 2.30–2.55 (m, 2H), 3.10–3.55 (m, 2H), 3.85–4.35 (m, 3H), 5.15 (s, 2H), 7.40–7.55 (m, 5H).

Reference Example 8

Preparation of N-tert-butoxycarbonyl-L-seryl-L-glutamic acid 1,5-dibenzyl ester [stereoisomer of the compound (Vb) wherein n is 1]:

To a solution of L-glutamic acid 1,5-dibenzyl ester p-toluenesulfonate (10.0 g), Boc-Ser (4.1 g) and TEA (2.0 g) in DMF (200 ml) are added with stirring WSC (5.0 g) and HOBt (4.0 g) under ice-cooling. The mixture is stirred at room temperature for 20 hours, and thereto is added ethyl acetate (200 ml). The mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration, and washed with ether to give N-tert-butoxycarbonyl-L-seryl-L-glutamic acid 1,5-dibenzyl ester (9.7 g) as colorless crystals.

M.p. 93–95° C.; $^1$H-NMR (DMSO-d$_6$)δ: 1.36 (s, 9H), 1.80–1.98 (m, 1H), 1.99–2.12 (m, 1H), 2.43 (t, 2H, J=7.6 Hz), 3.40–3.62 (m, 2H), 4.00 (dd, 1H, J=6.8, 12.2 Hz), 4.32–4.46 (m, 1H), 4.78 (t, 1H, J=5.8 Hz), 5.07 (s, 2H), 5.11 (s, 1H), 6.70 (d, 1H, J=8.0 Hz) 7.29–7.45 (m, 10H), 8.23 (d, 1H, J=7.8 Hz).

Reference Example 9

Preparation of N-tert-butoxycarbonyl-L-seryl-D-glutamic acid 1-anilide 5-benzyl ester [stereoisomer of the compound (Va) wherein R$^3$ is phenyl group, and n is 1]:

(1) N-tert-butoxycarbonyl-D-glutamic acid 1-anilide 5-benzyl ester [R-isomer of the compound (XV) wherein R$^3$ is phenyl group and n is 1]:

To a solution of N-tert-butoxycarbonyl-D-glutamic acid 5-benzyl ester (2.0 g) in THF (30 ml) is added TEA (0.78 g), and thereto is added with stirring ethyl chlorocarbonate (0.84 g) under ice-cooling. The mixture is stirred for two minutes, and thereto is added aniline (1.4 g). The mixture is stirred for 23 hours while it is gradually warmed to room temperature. To the mixture is added ethyl acetate (100 ml), and the mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration, and washed with ether to give N-tert-butoxycarbonyl-D-glutamic acid 1-anilide 5-benzyl ester (1.4 g) as colorless crystals.

M.p. 114–116° C.; $^1$H-NMR (DMSO-d$_6$)δ: 1.38 (s, 9H), 1.78–2.08 (m, 2H), 2.44 (t, 2H, J=7.6 Hz), 4.10 (dd, 1H, J=8.1, 13.6 Hz), 5.07 (s, 2H), 7.05 (t, 1H, J=7.4 Hz), 7.12 (d, 1H, J=7.8 Hz), 7.20–7.42 (m, 7H), 7.59 (dd, 2H, J=1.1, 8.6 Hz), 9.98 (s, 1H (2) N-tert-butoxycarbonyl-L-seryl-D-glutamic acid 1-anilide 5-benzyl ester:

To a solution of the compound obtained in the above (1) (1.3 g) in methylene chloride (10 ml) is added with stirring TFA (10 ml) under ice-cooling, and the mixture is stirred for two hours. The mixture is concentrated under reduced pressure, and the resulting syrup is dissolved in chloroform (50 ml). The mixture is washed with a saturated aqueous sodium hydrogen carbonate solution, dried, and concentrated under reduced pressure to give the de-protected compound as a syrup. Separately, Boc-Ser (0.65 g) is dissolved in THF (50 ml), and thereto is added TEA (0.34 g), and further thereto is added with stirring ethyl chlorocarbonate (0.36 g) under ice-cooling. The mixture is stirred for three minutes, and then thereto is added a solution of the syrup obtained above in THF (5 ml), and the mixture is stirred for four hours. To the reaction mixture is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (n-hexane:ethyl acetate=2:3) to give (N-tert-butoxycarbonyl-L-seryl)-D-glutamic acid 1-anilide 5-benzyl ester (0.81 g) as colorless crystals.

M.p. 93–98° C.; $^1$H-NMR (DMSO-$d_6$)δ: 1.36 (s, 9H), 1.80–2.00 (m, 1H), 2.02–2.22 (m, 1H), 2.30–2.50 (m, 2H), 3.58 (t, 2H, J=5.6 Hz), 3.92–4.06 (m, 1H), 4.48–4.54 (m, 1H), 4.95 (t, 1H, J=5.7 Hz), 5.04 (d, 1H, J=12.6 Hz), 5.09 (d, 1H, J=13.0 Hz), 6.82 (d, 1H, J=7.0 Hz), 7.06 (t, 1H, J=7.4 Hz), 7.22–7.44 (m, 7H), 7.61 (d, 2H, J=7.8 Hz), 8.20 (d, 1H, J=8.0 Hz), 9.75 (s, 1H).

Reference Example 10

Preparation of (2,3,4-tri-O-acetyl)-L-fucopyranosyl fluoride [the compound (VII)]:

(2,3,4-Tri-O-acetyl)-L-fucopyranose (13.1 g) is dissolved in methylene chloride (100 ml), and thereto is added with stirring DAST (10.9 g) under ice-cooling, and the mixture is stirred for 4 hours under ice-cooling. The reaction mixture is poured into ice-water (200 g), and the mixture is separated. The organic layer is dried, and concentrated under reduced pressure. The resulting residue is purified by silica gel column chromatography (n-hexane:ethyl acetate=1:4→1:2) to give (2,3,4-tri-O-acetyl)-L-fucopyranosyl fluoride (10.6 g) in the form of a mixture of α-anomer and β-anomer.

α-anomer:
$^1$H-NMR (CDCl$_3$)δ: 1.20 (d, 3H, J=6.5 Hz), 2.01 (s, 3H), 2.12 (s, 3H), 2.18 (s, 3H), 4.29–4.48 (m, 1H), 5.06–5.30 (m, 1H), 5.30–5.48 (m, 2H), 5.70 (dd, 1H, J=2.6, 53.7 Hz).

β-anomer:
$^1$H-NMR (CDCl$_3$)δ: 1.28 (d, 3H, J=6.4 Hz), 2.00 (s, 3H), 2.10 (s, 3H), 2.20 (s, 3H), 3.90–4.06 (m, 1H), 4.94–5.13 (m, 1H), 5.23 (dd, 1H, J=7.5, 46.9 Hz), 5.30–5.48 (m, 1H).

Reference Example 11

Preparation of (N-t-butoxycarbonyl-L-cysteinyl)-D-glutamic acid 1-methylamide 5-benzyl ester [stereoisomer of the compound (XIII) wherein $R^4$ is methylcarbamoyl group, and n is 1]:
(1) Cystine derivative [stereoisomer of the compound (XXII) wherein $R^4$ is methylcarbamoyl group, and n is 1]:

To a solution of N-tert-butoxycarbonyl-D-glutamic acid 1-methylamide 5-benzyl ester (2.5 g, Reference Example 2-(1)) in methylene chloride (25 ml) is added with stirring TFA (25 ml) under ice-cooling, and the mixture is stirred for two hours. The mixture is concentrated under reduced pressure, and the resulting syrup is dissolved in chloroform (100 ml). The mixture is washed with a saturated aqueous sodium hydrogen carbonate solution, dried, and concentrated under reduced pressure to give the de-protected compound as a syrup. The syrup thus obtained is dissolved in DMF (100 ml), and thereto is added Boc-L-cystine (1.6 g), and further thereto are added with stirring WSC (2.0 g) and HOBt (1.6 g) under ice-cooling. The mixture is stirred at room temperature for 19 hours, and concentrated under reduced pressure. To the resulting residue is added ethyl acetate (120 ml), and the mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration to give the desired compound (2.4 g) as colorless crystals.

M.p. 180–182° C.; $^1$H-NMR (DMSO-$d_6$)δ: 1.37 (s, 18H), 1.65–1.9 (m, 2H), 1.9–2.18 (m, 2H), 2.2–2.45 (m, 4H), 2.57 (d, 6H, J=4.2 Hz), 2.75–2.95 (m, 2H), 2.95–3.18 (m, 2H), 4.05–4.35 (m, 2H), 5.06 (s, 4H), 7.24 (d, 2H, J=7.2 Hz), 7.34 (s, 10H), 7.78 (d, 2H, J=4.1 Hz), 8.19 (d, 2H, J=7.7 Hz).

(2) (N-t-butoxycarbonyl-L-cysteinyl)-D-glutamic acid 1-methylamide 5-benzyl ester:

The compound obtained in the above (1) (2.3 g) is dissolved in a mixture of methanol-water (80–0.8 ml), and thereto is added n-Bu$_3$P, and the mixture is stirred at room temperature for one hour. The mixture is concentrated under reduced pressure, and the resultant is crystallized from ether to give (N-t-butoxy-carbonyl-L-cysteinyl)-D-glutamic acid 1-methylamide 5-benzyl ester (1.7 g) as colorless crystals.

M.p. 112–114° C.; $^1$H-NMR (DMSO-$d_6$)δ: 1.38 (s, 9H), 1.67–1.88 (m, 1H), 1.9–2.1 (m, 1H), 2.25–2.45 (m, 2H), 2.58 (d, 3H, J=4.5 Hz), 2.6–2.8 (m, 2H), 3.9–4.08 (m, 1H), 4.12–4.32 (m, 1H), 5.07 (s, 2H), 7.14 (d, 1H, J=7.0 Hz), 7.25–7.4 (m, 5H), 7.79 (d, 1H, J=4.5 Hz), 8.21 (d, 1H, J=8.2 Hz).

Reference Example 12

Preparation of N-tert-butoxycarbonyl-D-seryl-L-glutamic acid 1-methyl-amide 5-benzyl ester [stereoisomer of the compound (Va) wherein $R^3$ is methyl group and n is 1]:

To a solution of N-tert-butoxycarbonyl-L-glutamic acid 1-methylamide 5-benzyl ester [5.0 g, Reference Example 1-(1)] in methylene chloride (50 ml) is added with stirring TFA (50 ml) under ice-cooling, and the mixture is stirred for three hours. The mixture is concentrated under reduced pressure, and the resulting syrup is dissolved in chloroform (120 ml), and washed with a saturated aqueous sodium hydrogen carbonate solution, dried, and concentrated under reduced pressure to give the de-protected compound as a syrup. The syrup thus obtained is dissolved in DMF (80 ml), and thereto is added Boc-D-Ser (2.9 g), and further thereto are added with stirring WSC (3.6 g) and HOBt (2.8 g) under ice-cooling. The mixture is stirred at room temperature for 20 hours, and thereto is added ethyl acetate (150 ml). The mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration, and washed with ether to give the title stereoisomer (4.4 g) as colorless crystals.

M.p. 126–128° C.; $^1$H-NMR (CDCl$_3$)δ: 1.44 (s, 9H), 1.90–2.11 (m, 1H), 2.12–2.30 (m, 1H), 2.35–2.64 (m, 2H), 2.76 (d, 3H, J=4.5 Hz), 3.60–3.80 (m, 1H), 3.97 (dd, 1H, J=3.4 11.2 Hz), 4.04–4.20 (m, 1H), 4.35–4.55 (m, 1H), 5.08 (d, 1H, J=12.3 Hz), 5.14 (d, 1H, J=12.3 Hz), 5.66 (d, 1H, J=5.7 Hz), 6.77 (d, 1H, J=4.5 Hz), 7.28–7.50 (m, 5H).

Example 1

Preparation of [N-tert-butoxycarbonyl-O-(2,3,4-tri-O-benzyl-α-L-fucofuranosyl)-L-seryl]-L-glutamic acid 1-methylamide 5-benzyl ester [α-anomer of the compound (II-3) wherein $R^4$ is methylcarbamoyl group, and n is 1]:

To Molecular Sieves 4 Å (1.0 g) are added methylene chloride (10 ml), AgOTf (1.17 g) and $SnCl_2$ (0.88 g), and the mixture is cooled to −40∼−50° C. under argon atmosphere. To the mixture is added TMU (1.3 g), and further thereto are added a solution of (2,3,4-tri-O-benzyl)-L-fucofuranosyl fluoride (1.5 g, the compound (VIII)) in methylene chloride (2 ml), and a solution of N-tert-butoxycarbonyl-L-seryl-L-glutamic acid 1-methylamide 5-benzyl ester (1.0 g, the stereoisomer of Reference Example 1) in methylene chloride (5 ml), and the mixture is stirred at the same temperature for one hour. The mixture is stirred for 23 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (n-hexane:ethyl acetate=1:1), and crystallized from ether to give the title stereoisomer (0.54 g) as colorless crystals.

$[\alpha]_D$−34.2° (c=0.1, MeOH); M.p. 132–133° C.; $^1$H-NMR (DMSO-$d_6$)δ: 1.07 (d, 3H, J=6.2 Hz), 1.30 (s, 9H), 1.68–1.85 (m, 1H), 1.85–2.10 (m, 1H), 2.30–2.45 (m, 2H), 2.54 (d, 3H, J=4.5 Hz), 3.50 (t, 1H, J=6.6 Hz), 3.60–3.80 (m, 3H), 3.95–4.10 (m, 2H), 4.15–4.40 (m, 2H), 4.40–4.70 (m, 6H), 5.05 (s, 2H), 5.12 (d, 1H, 3.7 Hz), 7.15–7.40 (m, 20H), 7.80 (d, 1H, J=4.5 Hz), 7.96 (d, 1H, J=8.3 Hz).

Elementary Analysis for $C_{48}H_{59}N_3O_{11}$; Calculated: C, 67.51; H, 6.96; N, 4.92; Found: C, 67.48; H, 6.94; N, 4.91

Example 2

Preparation of [N-tert-butoxycarbonyl-O-(2,3,4-tri-O-benzyl-α-L-fucofuranosyl)-L-seryl]-D-glutamic acid 1-methylamide 5-benzyl ester [α-anomer of the compound (II-3) wherein $R^4$ is methylcarbamoyl group, and n is 1]:

To Molecular Sieves 4 Å (1.0 g) are added methylene chloride (10 ml), AgOTf (0.89 g) and $SnCl_2$ (0.66 g), and the mixture is cooled to −40∼−50° C. under argon atmosphere. To the mixture is added TMU (1.0 g), and then further are added a solution of (2,3,4-tri-O-benzyl)-L-fucofuranosyl fluoride (1.1 g, the compound (VIII)) in methylene chloride (2 ml), and a solution of N-tert-butoxycarbonyl-L-seryl-D-glutamic acid 1-methylamide 5-benzyl ester (0.75 g, the stereoisomer of Reference Example 2) in methylene chloride (5 ml), and the mixture is stirred at the same temperature for one hour. The mixture is stirred for 19 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (n-hexane:ethyl acetate=2:3), and crystallized from ether to give the title stereoisomer (0.45 g) as colorless crystals.

$[\alpha]_D$−19° (c=0.1, MeOH); M.p. 122–126° C.; $^1$H-NMR (DMSO-$d_6$)δ: 1.07 (d, 3H, J=6.2 Hz), 1.33 (s, 9H), 1.68–1.85 (m, 1H), 1.90–2.08 (m, 1H), 2.21–2.42 (m, 2H), 2.57 (d, 3H, J=4.5 Hz), 3.45–3.60 (m, 1H), 3.58–3.70 (m, 2H), 3.70–3.82 (m, 1H), 4.00 (d, 2H, J=4.5 Hz), 4.10–4.30 (m, 2H), 4.35–4.65 (m, 6H), 5.03 (s, 2H), 5.05 (broad s, 1H), 6.93 (d, 1H, J=6.7 Hz), 7.15–7.40 (m, 20H), 7.79 (d, 1H, J=4.4 Hz), 8.19 (d, 1H, J=7.6 Hz).

Elementary Analysis for $C_{48}H_{59}N_3O_{11}$; Calculated: C, 67.51; H, 6.96; N, 4.92; Found: C, 67.34; H, 6.93; N, 4.94

Example 3

Preparation of [N-tert-butoxycarbonyl-O-(2,3,4-tri-O-benzyl-α-L-fucofuranosyl)-D-seryl]-L-glutamic acid 1-methylamide 5-benzyl ester [α-anomer of the compound (II-3) wherein $R^4$ is methylcarbamoyl group, and n is 1]:

To Molecular Sieves 4 Å (1.0 g) are added methylene chloride (10 ml), AgOTf (0.89 g) and $SnCl_2$ (0.66 g), and the mixture is cooled to −40∼−50° C. under argon atmosphere. To the mixture is added TMU (1.0 g), and then further are added a solution of (2,3,4-tri-O-benzyl)-L-fucofuranosyl fluoride (1.1 g, the compound (VIII)) in methylene chloride (2 ml), and a solution of N-tert-butoxy-carbonyl-D-seryl-L-glutamic acid 1-methylamide 5-benzyl ester (0.75 g, the stereoisomer of Reference Example 3) in methylene chloride (5 ml), and the mixture is stirred at the same temperature for one hour. The mixture is stirred for 22 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (n-hexane:ethyl acetate=2:3), and crystallized from ether to give the title stereoisomer (0.41 g) as colorless crystals.

$[\alpha]_D$−21° (c=0.1, MeOH); M.p. 110–116° C.;

$^1$H-NMR (DMSO-$d_6$)δ: 1.07 (d, 3H, J=6.2 Hz), 1.36 (s, 9H), 1.65–1.85 (m, 1H), 1.90–2.12 (m, 1H), 2.32 (t, 2H, J=7.2 Hz), 2.57 (d, 3H, J=4.5 Hz), 3.45–3.70 (m, 3H), 3.78–3.91 (m, 1H), 3.95–4.05 (m, 1H), 4.10–4.30 (m, 2H), 4.35–4.72 (m, 6H), 5.02 (s, 2H), 5.09 (s, 1H), 7.16 (d, 1H, J=7.0 Hz), 7.20–7.45 (m, 20H), 7.79 (d, 1H, J=4.0 Hz), 8.17 (d, 1H, J=7.9 Hz).

Elementary Analysis for $C_{48}H_{59}N_3O_{11}$; Calculated: C, 67.51; H, 6.96; N, 4.92; Found: C, 67.47; H, 6.97; N, 4.87

Example 4

Preparation of [N-tert-butoxycarbonyl-O-( 2,3,4-tri-O-benzyl-α-L-fucofuranosyl)-D-seryl]-D-glutamic acid 1-methylamide 5-benzyl ester [α-anomer of the compound (II-3) wherein $R^4$ is methylcarbamoyl group, and n is 1]:

To Molecular Sieves 4 Å (1.0 g) are added methylene chloride (10 ml), AgOTf (0.89 g) and $SnCl_2$ (0.66 g), and the mixture is cooled to −40∼−50° C. under argon atmosphere. To the mixture is added TMU (1.0 g), and then further are added a solution of (2,3,4-tri-O-benzyl)-L-fucofuranosyl fluoride (1.1 g, the compound (VIII)) in methylene chloride (2 ml), and a solution of N-tert-butoxy-carbonyl-D-seryl-D-glutamic acid 1-methylamide 5-benzyl ester (0.75 g, the stereoisomer of Reference Example 4) in methylene chloride (5 ml), and the mixture is stirred at the same temperature for one hour. The mixture is stirred for 18 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (n-hexane:ethyl acetate=2:3), and crystallized from ether to give the title stereoisomer (0.41 g) as a colorless solid.

$[\alpha]_D$−17° (c=0.1, MeOH); M.p. 99–104° C.;

$^1$H-NMR (DMSO-$d_6$)δ: 1.08 (d, 3H, J=6.3 Hz), 1.33 (s, 9H), 1.70–1.89 (m, 1H), 1.90–2.05 (m, 1H), 2.32–2.45 (m, 2H), 3.45–3.75 (m, 3H), 3.80–3.91 (m, 1H), 3.94–4.10 (m, 2H), 4.10–4.25 (m, 1H), 4.25–4.38 (m, 1H), 4.36–4.70 (m, 6H), 5.05 (s, 2H), 7.10 (d, 1H, J=7.9 Hz), 7.15–7.42 (m, 20H), 7.81 (d, 1H, J=4.5 Hz), 7.95 (d, 1H, J=7.9 Hz).

Example 5

Preparation of [N-tert-butoxycarbonyl-O-(2,3,4-tri-O-benzyl-L-fucofuranosyl)-L-seryl]-L-glutamic acid 1,5-dibenzyl ester [a mixture of α-anomer and β-anomer of the compound (II-3) wherein $R^4$ is benzyloxycarbonyl group, and n is 1]:

To Molecular Sieves 4 Å (0.5 g) are added methylene chloride (2 ml), AgOTf (0.51 g) and $SnCl_2$ (0.38 g), and the mixture is cooled to −40∼−50° C. under nitrogen atmosphere. To the mixture is added TMU (0.47 g), and further thereto are added a solution of (2,3,4-tri-O-benzyl)-L-fucofuranosyl fluoride (0.66 g, the compound (VIII)) in methylene chloride (2 ml), and a solution of N-tert-butoxycarbonyl-L-seryl-L-glutamic acid 1,5-dibenzyl ester (0.52 g, the stereoisomer of Reference Example 8) in methylene chloride (4 ml), and the mixture is stirred at the same temperature for one hour. The mixture is stirred for 17 hours while it is gradually warmed to room temperature. The reaction mixture is filtered, and the filtrate is washed with a saturated aqueous sodium hydrogen carbonate solution, dried, and concentrated under reduced pressure. The resulting residue is purified by silica gel medium-pressure liquid chromatography (n-hexane:ethyl acetate=4:1→1:1) to give a mixture of α-anomer and β-anomer of [N-tert-butoxycarbonyl-O-(2,3,4-tri-O-benzyl-L-fucofuranosyl)-L-seryl]-L-glutamic acid 1,5-dibenzyl ester (0.76 g, α-anomer:β-anomer=2:1) as a syrup.

$^1$H-NMR (DMSO-$d_6$)δ: 1.07 (d, J=6.2 Hz), 1.14 (d, J=5.6 Hz), 1.30 (s), 1.80–1.95 (m), 2.00–2.15 (m), 2.40–2.50 (m), 3.50–3.60 (m), 3.60–3.75 (m), 4.00–4.10 (m), 4.20–4.65 (m), 5.06 (s), 5.07 (d, J=5.1 Hz), 5.11 (d, J=3.3 Hz), 7.15–7.45 (m), 8.30–8.45 (m).

Example 6

Preparation of [N-tert-butoxycarbonyl-O-(2,3,4-tri-O-benzyl-α-L-fucofuranosyl)-L-seryl]-L-aspartic acid 1-methylamide 4-benzyl ester [a mixture of α-anomer and β-anomer of the compound (II-3) wherein $R^4$ is methylcarbamoyl group, and n is 0]:

To Molecular Sieves 4 Å (0.5 g) are added methylene chloride (2 ml), AgOTf (0.26 g) and $SnCl_2$ (0.20 g), and the mixture is cooled to −40∼−50° C. under nitrogen atmosphere. To the mixture is added TMU (0.24 g), and then further are added a solution of (2,3,4-tri-O-benzyl)-L-fucofuranosyl fluoride (0.39 g, the compound (VIII)) in methylene chloride (2 ml), and a solution of [N-tert-butoxycarbonyl-L-seryl]-L-aspartic acid 1-methylamide 4-benzyl ester (0.22 g, the stereoisomer of Reference Example 5) in methylene chloride (4 ml), and the mixture is stirred at the same temperature for one hour. The mixture is stirred for 15 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (chloroform:MeOH=10:1) to give a mixture of α-anomer and β-anomer of [N-tert-butoxycarbonyl-O-(2,3,4-tri-O-benzyl-α-L-fucofuranosyl)-L-seryl]-L-aspartic acid 1-methylamide 4-benzyl ester (0.23 g, α-anomer:β-anomer=2:1) as a syrup.

$^1$H-NMR (DMSO-$d_6$)δ: 1.08 (d, J=6.2 Hz), 1.15 (d, J=6.1 Hz), 1.34 (s), 1.36 (s), 2.69 (s), 2.75–2.90 (m), 3.50–3.60 (m), 3.60–3.80 (m), 3.85–3.95 (m), 4.10–4.15 (m), 4.40–4.70 (m), 5.05 (s), 5.06 (s), 5.11 (d, J=4.1 Hz), 7.15–7.45 (m), 7.60–7.80 (m). 8.24 (d, J=8.2 Hz).

Example 7

Preparation of 4-N-[N-tert-butoxycarbonyl-O-(2,3,4-tri-O-benzyl-L-fucofuranosyl)-L-seryl]aminobutyric acid benzyl ester [a mixture of α-anomer and β-anomer of the compound (II-3) wherein $R^4$ is hydrogen atom, and n is 1]:

To Molecular Sieves 4 Å (0.5 g) are added methylene chloride (2 ml), AgOTf (0.53 g) and $SnCl_2$ (0.40 g), and the mixture is cooled to −40∼−50° C. under nitrogen atmosphere. To the mixture is added TMU (0.49 g), and then further are added a solution of (2,3,4-tri-O-benzyl)-L-fucofuranosyl fluoride (0.69 g, the compound (VIII)) in methylene chloride (2 ml), and a solution of 4-N-(N-tert-butoxycarbonyl-L-seryl)aminobutyric acid benzyl ester (0.40 g, the stereoisomer of Reference Example 6) in methylene chloride (8 ml), and the mixture is stirred at the same temperature for one hour. The mixture is stirred for 13 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (cyclohexane:ethyl acetate=2:1) to give a mixture of α-anomer and β-anomer of 4-N-[N-tert-butoxycarbonyl-O-(2,3,4-tri-O-benzyl-L-fucofuranosyl)-L-seryl]-aminobutyric acid benzyl ester (0.56 g, α-anomer:β-anomer=2:1) as a syrup.

$[α]_D$ −7° (c=0.1, $CHCl_3$); M.p. 94–97° C.; $^1$H-NMR ($CDCl_3$)δ: 1.16 (d, J=6.6 Hz), 1.40 (s), 1.60–1.80 (m), 2.10–2.45 (m), 2.90–3.30 (m), 3.40–3.85 (m), 3.85–4.25 (m), 4.40–4.70 (m), 5.08 (s), 7.10–7.50 (m)

Example 8

Preparation of 5-N-[N-tert-butoxycarbonyl-O-(2,3,4-tri-O-benzyl-L-fucofuranosyl)-L-seryl]aminovaleric acid benzyl ester [a mixture of α-anomer and β-anomer of the compound (II-3) wherein $R^4$ is hydrogen atom, and n is 2]:

To Molecular Sieves 4 Å (0.5 g) are added methylene chloride (4 ml), AgOTf (0.75 g) and $SnCl_2$ (0.57 g), and the mixture is cooled to −40∼−50° C. under nitrogen atmosphere. To the mixture is added TMU (0.70 g), and then further are added a solution of (2,3,4-tri-O-benzyl)-L-fucofuranosyl fluoride (0.98 g, the compound (VIII)) in methylene chloride (4 ml), and a solution of 5-N-(N-tert-butoxycarbonyl-L-seryl)aminovaleric acid benzyl ester (0.59 g, the stereoisomer of Reference Example 7) in methylene chloride (8 ml), and the mixture is stirred at the same temperature for one hour. The mixture is stirred for 18 hours while it is gradually warmed to room temperature. The reaction mixture is filtered, and the filtrate is washed with a saturated aqueous sodium hydrogen carbonate solution, dried, and concentrated under reduced pressure. The resulting residue is purified by silica gel medium-pressure liquid chromatography (n-hexane:ethyl acetate=10:1→1:1) to give a mixture of α-anomer and β-anomer of 5-N-[N-tert-butoxycarbonyl-O-(2,3,4-tri-O-benzyl-L-fucofuranosyl)-L-seryl]aminovaleric acid benzyl ester (0.90 g, α-anomer:β-anomer=2:1) as a syrup.

$[α]_D$ −9° (c=0.1, $CHCl_3$); $^1$H-NMR (DMSO-$d_6$)δ: 1.07 (d, J=6.2 Hz), 1.14 (d, J=6.2 Hz), 1.32 (s), 1.35 (s), 1.35–1.55 (m), 2.30 (t, J=7.1 Hz), 2.90–3.10 (m), 3.45–3.75 (m), 3.85–3.95 (m), 3.97–4.10 (m), 4.10–4.20 (m), 4.40–4.70 (m), 5.06 (s), 5.07 (s), 5.08 (d, J=4.1 Hz), 6.68 (d, J=7.5 Hz), 7.20–7.40 (m), 7.85–7.95 (m).

Example 9

Preparation of [N-(2-tetradecylhexadecanoyl)-O-(2,3,4-tri-O-benzyl-α-L-fucofuranosyl)-L-seryl]-L-glutamic acid 1-methylamide 5-benzyl ester [α-anomer of the compound (II-4) wherein $R^1$ is 1-tetradecylpentadecyl group, $R^4$ is methylcarbamoyl group, and n is 1]:

The compound obtained in Example 1 (0.4 g) is dissolved in methylene chloride (2 ml), and thereto is added with stirring TFA (2 ml) under ice-cooling, and the mixture is stirred for two hours. The reaction mixture is concentrated, and thereto is added chloroform (50 ml). The mixture is washed with a saturated aqueous sodium hydrogen carbonate solution, dried, and concentrated under reduced pressure. The resulting de-protected syrup product is dissolved in DMF (30 ml), and thereto is added 2-tetradecylhexadecanoic acid (0.21 g), and further thereto are added with stirring WSC (0.14 g) and HOBt (0.11 g) under ice-cooling. The mixture is stirred for 18 hours while it is gradually warmed to room temperature. To the reaction solution is added chloroform (80 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.22 g) as colorless crystals.

$[\alpha]_D$ –14° (c=0.1, CHCl$_3$); M.p. 139–142° C.; $^1$H-NMR (DMSO-d$_6$)δ: 0.75–0.95 (m, 6H), 1.00–1.55 (m, 55H), 1.72–1.85 (m, 1H), 1.90–2.05 (m, 1H), 2.10–2.25 (m, 1H), 2.25–2.45 (m, 2H), 3.49–3.60 (m, 1H), 3.60–3.70 (m, 1H), 3.72 (d, 2H, J=6.1 Hz), 3.95–4.05 (m, 2H), 4.25–4.40 (m, 1H), 4.38–4.73 (m, 7H), 5.05 (s, 2H), 5.13 (d, 1H, J=3.4 Hz), 7.20–7.45 (m, 20H), 7.75 (d, 1H, J=4.7 Hz), 7.94 (d, 1H, J=8.2 Hz), 8.02 (d, 1H, J=7.8 Hz).

Elementary Analysis for $C_{73}H_{109}N_3O_{10}$; Calculated: C, 73.76; H, 9.24; N, 3.54; Found: C, 73.83; H, 9.26; N, 3.57

Example 10

Preparation of [N-(2-tetradecylhexadecanoyl)-O-(2,3,4-tri-O-benzyl-α-L-fucofuranosyl)-L-seryl]-D-glutamic acid 1-methylamide 5-benzyl ester [α-anomer of the compound (II-4) wherein $R^1$ is 1-tetradecylpentadecyl group, $R^4$ is methylcarbamoyl group, and n is 1]:

The compound obtained in Example 2 (0.4 g) is dissolved in methylene chloride (3 ml), and thereto is added with stirring TFA (3 ml) under ice-cooling, and the mixture is stirred for two hours. The reaction mixture is concentrated, and thereto is added chloroform (50 ml). The mixture is washed with a saturated aqueous sodium hydrogen carbonate solution, dried, and concentrated under reduced pressure. The resulting de-protected syrup product is dissolved in DMF (30 ml), and thereto is added 2-tetradecylhexadecanoic acid (0.21 g), and further thereto are added with stirring WSC (0.14 g) and HOBt (0.11 g) under ice-cooling. The mixture is stirred for 22 hours while it is gradually warmned to room temperature. To the reaction solution is added chloroform (80 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.27 g) as colorless crystals.

$[\alpha]_D$ –14° (c=0.1, CHCl$_3$); M.p. 127–129° C.; $^1$H-NMR (DMSO-d$_6$)δ: 0.75–0.95 (m, 6H), 1.06 (d, 3H, J=6.1 Hz), 1.10–1.60 (m, 55H), 1.65–1.85 (m, 1H), 1.85–2.10 (m, 1H), 2.10–2.25 (m, 1H), 2.25–2.40 (m, 2H), 2.55 (d, 3H, J=4.5 Hz), 3.49–3.60 (m, 1H), 3.60–3.70 (m, 2H), 3.70–3.85 (m, 1H), 3.95–4.05 (m, 2H), 4.15–4.25 (m, 1H), 4.39–4.72 (m, 7H), 5.01 (s, 2H), 5.04 (d, 1H, J=3.3 Hz), 7.15–7.40 (m, 20H), 7.84 (d, 1H, J=4.6 Hz), 8.11 (d, 1H, J=6.7 Hz), 8.28 (d, 1H, J=8.2 Hz).

Elementary Analysis for $C_{73}H_{109}N_3O_{10}$; Calculated: C, 73.76; H, 9.24; N, 3.54; Found: C, 73.69; H, 9.25; N, 3.33

Example 11

Preparation of [N-(2-tetradecylhexadecanoyl)-O-(2,3,4-tri-O-benzyl-α-L-fucofuranosyl)-D-seryl]-L-glutamic acid 1-methylamide 5-benzyl ester [α-anomer of the compound (II-4) wherein $R^1$ is 1-tetradecylpentadecyl group, $R^4$ is methylcarbamoyl group, and n is 1]:

The compound obtained in Example 3 (0.37 g) is dissolved in methylene chloride (3 ml), and thereto is added with stirring TFA (3 ml) under ice-cooling, and the mixture is stirred for two hours. The reaction mixture is concentrated, and thereto is added chloroform (50 ml). The mixture is washed with a saturated aqueous sodium hydrogen carbonate solution, dried, and concentrated under reduced pressure. The resulting de-protected syrup product is dissolved in DMF (30 ml), and thereto is added 2-tetradecylhexadecanoic acid (0.20 g), and further thereto are added with stirring WSC (0.13 g) and HOBt (0.10 g) under ice-cooling. The mixture is stirred for 20 hours while it is gradually warmed to room temperature. To the reaction solution is added chloroform (50 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.23 g) as colorless crystals.

$[\alpha]_D$ –19° (c=0.1, CHCl$_3$); M.p. 114–117° C.; $^1$H-NMR (DMSO-d$_6$)δ: 0.75–0.95 (m, 6H), 1.06 (d, 3H, J=6.2 Hz), 1.10–1.50 (m, 52H), 1.65–1.85 (m, 1H), 1.88–2.12 (m, 1H), 2.15–2.30 (m, 1H), 2.30–2.42 (m, 2H), 2.55 (d, 3H, J=4.5 Hz), 3.45–3.72 (m, 3H), 3.80–3.95 (m, 1H), 3.95–4.05 (m, 2H), 4.16–4.30 (m, 1H), 4.38–4.72 (m, 7H), 5.00 (s, 2H), 5.10 (d, 1H, J=3.1 Hz), 7.15–7.45 (m, 20H), 7.84 (d, 1H, J=4.7 Hz), 8.16 (d, 1H, J=6.7 Hz), 8.26 (d, 1H, J=8.1 Hz).

Elementary Analysis for $C_{73}H_{109}N_3O_{10}$; Calculated: C, 73.76; H, 9.24; N, 3.54; Found: C, 73.80; H, 9.24; N, 3.57

Example 12

Preparation of [N-(2-tetradecylhexadecanoyl)-O-( 2,3,4-tri-O-benzyl-α-L-fucofuranosyl)-D-seryl]-D-glutamic acid 1-methylamide 5-benzyl ester [α-anomer of the compound (II-4) wherein $R^1$ is 1-tetradecylpentadecyl group, $R^4$ is methylcarbamoyl group, and n is 1]:

The compound obtained in Example 4 (0.35 g) is dissolved in methylene chloride (3 ml), and thereto is added with stirring TFA (3 ml) under ice-cooling, and the mixture is stirred for two hours. The reaction mixture is concentrated, and thereto is added chloroform (50 ml). The mixture is washed with a saturated aqueous sodium hydrogen carbonate solution, dried, and concentrated under reduced pressure. The resulting de-protected syrup product is dissolved in DMF (30 ml), and thereto is added 2-tetradecylhexadecanoic acid (0.19 g), and further thereto are added with stirring WSC (0.12 g) and HOBt (0.09 g) under ice-cooling. The mixture is stirred for 20 hours while it is gradually warmed to room temperature. To the reaction solution is added chloroform (80 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.25 g) as colorless crystals.

$[\alpha]_D$-15° (c=0.1, CHCl$_3$); M.p. 125–126° C.; $^1$H-NMR (DMSO-d$_6$)δ: 0.75–0.95 (m, 6H), 1.07 (d, 3H, J=6.2 Hz), 1.10–1.60 (m, 52H), 1.70–1.85 (m, 1H), 1.88–2.05 (m, 1H), 2.16–2.30 (m, 1H), 2.30–2.41 (m, 2H), 3.53 (t, 1H, J=6.3 Hz), 3.60–3.72 (m, 2H), 3.80–3.92 (m, 1H), 4.00 (d, 2H, J=4.6 Hz), 4.19–4.31 (m, 1H), 4.40–4.72 (m, 7H), 5.06 (s, 2H), 5.12 (s, 1H) 7.20–7.45 (m, 20H), 7.71 (d, 1H, J=4.8 Hz), 8.01 (d, 2H, J=7.7 Hz).

Elementary Analysis for C$_{73}$H$_{109}$N$_3$O$_{10}$; Calculated: C, 73.76; H, 9.24; N, 3.54; Found: C, 73.50; H, 9.14; N, 3.51

Example 13

Preparation of [N-(2-tetradecylhexadecanoyl)-O-(2,3,4-tri-O-benzyl-L-fucofuranosyl)-L-seryl]-L-glutamic acid 1,5-dibenzyl ester [a mixture of α-anomer and β-anomer of the compound (II-4) wherein R$^1$ is 1-tetradecyl-pentadecyl group, R$^4$ is benzyloxycarbonyl group, and n is 1]:

The compound obtained in Example 5 (0.28 g) is dissolved in methylene chloride (1 ml), and thereto is added with stirring TFA (0.3 ml) under ice-cooling, and the mixture is stirred for 5 hours. The reaction mixture is concentrated, and thereto is added chloroform (15 ml). The mixture is washed with a saturated aqueous sodium hydrogen carbonate solution, dried, and concentrated under reduced pressure. The resulting de-protected syrup product is dissolved in DMF (10 ml), and thereto is added 2-tetradecylhexadecanoic acid (0.14 g), and further thereto are added with stirring WSC (0.09 g) and HOBt (0.07 g) under ice-cooling. The mixture is stirred for 15 hours while it is gradually warmed to room temperature. To the reaction solution is added chloroform (50 ml), and the mixture is washed successively with 1N hydrochloric acid, a saturated aqueous sodium hydrogen carbonate solution, water, and a saturated aqueous sodium chloride solution, dried, and concentrated under reduced pressure. The resulting residue is purified by silica gel medium-pressure liquid chromatography (n-hexane:ethyl acetate=10:1→4:1, chloroform:MeOH=20:1) to give a mixture of α-anomer and β-anomer of [N-(2-tetradecylhexadecanoyl)-O-(2,3,4-tri-O-benzyl-L-fucofuranosyl)-L-seryl]-L-glutamic acid 1,5-dibenzyl ester (0.06 g, α-anomer:β-anomer=2:1) as colorless crystals.

$^1$H-NMR (DMSO-d$_6$)δ: 0.75–0.95 (m), 1.07 (d, J=6.3 Hz), 1.00–1.50 (m), 1.80–1.95 (m), 2.00–2.10 (m), 2.10–2.25 (m), 2.42 (t, J=8.6 Hz), 3.50–3.60 (m), 3.65–3.80 (m), 3.85–3.90 (m), 3.95–4.00 (m), 4.35–4.70 (m), 5.06 (s), 5.11 (s), 7.20–7.40 (m), 7.99 (d, J=7.7 Hz), 8.38 (d, J=7.4 Hz).

Example 14

Preparation of [N-(2-tetradecylhexadecanoyl)-O-(2,3,4-tri-O-benzyl-L-fucofuranosyl)-L-seryl]-L-aspartic acid 1-methylamide 4-benzyl ester [a mixture of α-anomer and β-anomer of the compound (II-4) wherein R$^1$ is 1-tetradecylpentadecyl group, R$^4$ is methylcarbamoyl group, and n is 0]:

The compound obtained in Example 6 (0.21 g) is dissolved in methylene chloride (2 ml), and thereto is added with stirring TFA (2 ml) under ice-cooling, and the mixture is stirred for 4 hours. The reaction mixture is concentrated, and thereto is added chloroform (20 ml). The mixture is washed with a saturated aqueous sodium hydrogen carbonate solution, dried, and concentrated under reduced pressure. The resulting de-protected syrup product is dissolved in DMF (5 ml), and thereto is added 2-tetradecylhexadecanoic acid (0.13 g), and further thereto are added with stirring WSC (0.05 g) and HOBt (0.04 g) under ice-cooling. The mixture is stirred for 16 hours while it is gradually warmed to room temperature. To the reaction solution is added chloroform (20 ml), and the mixture is washed successively with 1N hydrochloric acid, a saturated aqueous sodium hydrogen carbonate solution, water, and a saturated aqueous sodium chloride solution, dried, and concentrated under reduced pressure. The resulting residue is purified by preparative thin layer chromatography (chloroform:MeOH=20:1) to give a mixture of α-anomer and β-anomer of N-(2-tetradecylhexadecanoyl)-O-(2,3,4-tri-O-benzyl-L-fucofuranosyl)-L-seryl]-L-aspartic acid 1-methylamide 4-benzyl ester (0.09 g, α-anomer:β-anomer=2:1).

$^1$H-NMR (DMSO-d$_6$)δ: 0.75–0.95 (m), 1.07 (d, J=6.3 Hz), 1.10–1.60 (m), 2.10–2.25 (m), 3.50–3.85 (m), 3.85–3.95 (m), 3.95–4.05 (m), 4.10–4.15 (m), 4.25–4.30 (m), 4.40–4.70 (m), 5.05 (s), 5.12 (s), 7.10–7.45 (m).

Example 15

Preparation of 4-N-[N-(2-tetradecylhexadecanoyl)-O-(2,3,4-tri-O-benzyl-α-L-fucofuranosyl)-L-seryl]aminobutyric acid benzyl ester [β-anomer of the compound (II-4) wherein R$^1$ is 2-tetradecylpentadecyl group, R$^4$ is hydrogen atom, and n is 1]:

The compound obtained in Example 7 (0.21 g) is dissolved in methylene chloride (2 ml), and thereto is added with stirring TFA (2 ml) under ice-cooling, and the mixture is stirred for 2 hours. The reaction mixture is concentrated, and thereto is added chloroform (20 ml). The mixture is washed with a saturated aqueous sodium hydrogen carbonate solution, dried, and concentrated under reduced pressure. The resulting de-protected syrup product is dissolved in DMF (5 ml), and thereto is added 2-tetradecylhexadecanoic acid (0.12 g), and further thereto are added with stirring WSC (0.05 g) and HOBt (0.04 g) under ice-cooling. The mixture is stirred for 16 hours while it is gradually warmed to room temperature. To the reaction solution is added chloroform (20 ml), and the mixture is washed successively with 1N hydrochloric acid, a saturated aqueous sodium hydrogen carbonate solution, water, and a saturated aqueous sodium chloride solution, dried, and concentrated under reduced pressure. The resulting residue is purified by preparative thin layer chromatography (cyclohexane:ethyl acetate=2:1) to give 4-N-[N-(2-tetradecylhexadecanoyl)-O-(2,3,4-tri-O-benzyl-α-L-fucofuranosyl)-L-seryl] aminobutyric acid benzyl ester (0.03 g).

M.p. 74–82° C.; $^1$H-NMR (DMSO-d$_6$)δ: 0.75–0.95 (m, 6H), 1.07 (d, 3H, J=6.2 Hz), 1.00–1.50 (m, 52H), 1.63 (q, 2H, J=7.3 Hz), 2.25–2.35 (m, 2H), 2.90–3.00 (m, 2H) 3.10–3.20 (m, 2H), 3.50–3.75 (m, 4H), 3.95–4.05 (m, 2H), 4.35–4.70 (m, 7H), 5.0 (s, 2H), 7.20–7.40 (m, 20H), 7.90–8.05 (m, 2H).

Example 16

Preparation of 5-N-[N-(2-tetradecylhexadecanoyl)-O-(2,3,4-tri-O-benzyl-α-L-fucofuranosyl)-L-seryl]aminovaleric acid benzyl ester [α-anomer of the compound (II-4) wherein R$^1$ is 1-tetradecylpentadecyl group, R$^4$ is hydrogen atom, and n is 2]:

The compound obtained in Example 8 (0.56 g) is dissolved in methylene chloride (4 ml), and thereto is added with stirring TFA (4 ml) under ice-cooling, and the mixture is stirred for one hour. The reaction mixture is concentrated, and thereto is added chloroform (20 ml). The mixture is washed with a saturated aqueous sodium hydrogen carbonate solution, dried, and concentrated under reduced pressure. The resulting de-protected syrup product is dissolved in DMF (20 ml), and thereto is added 2-tetradecylhexadecanoic acid (0.37 g), and further thereto are added with stirring WSC (0.15 g) and HOBt (0.12 g) under ice-cooling. The mixture is stirred for 19 hours while it is gradually warmed to room temperature. To the reaction solution is added ethyl acetate (20 ml), and the mixture is washed successively with 1N hydrochloric acid, a saturated aqueous sodium hydrogen carbonate solution, water, and a saturated aqueous sodium chloride solution, dried, and concentrated under reduced pressure. The resulting residue is purified by preparative thin layer chromatography (cyclohexane:ethyl acetate=2:1) to give 5-N-[N-(2-tetradecylhexadecanoyl)-O-(2,3,4-tri-O-benzyl-α-L-fucofuranosyl)-L-seryl]aminovaleric acid benzyl ester (0.16 g).

$[\alpha]_D$-28° (c=0.1, CHCl$_3$); M.p. 98–99° C.; $^1$H-NMR (DMSO-d$_6$)δ: 0.75–0.95 (m, 6H), 1.10 (d, 3H, J=6.3 Hz), 1.10–1.55 (m, 56H), 2.28 (t, 2H, J=7.1 Hz), 2.90–3.00 (m, 2H), 3.55–3.80 (m, 4H), 4.00–4.05 (m, 2H), 4.40–4.70 (m, 7H), 5.06 (s, 2H), 7.20–7.40 (m, 20H), 7.50–7.65 (m, 2H).

Example 17

Preparation of [N-(2-tetradecylhexadecanoyl)-O-(α-L-fucofuranosyl)-L-seryl]-L-glutamic acid 1-methylamide [α-anomer of the compound (Ib) wherein R$^1$ is 1-tetradecylpentadecyl group, R$^2$ is methylcarbamoyl group, and n is 1]:

To a solution of the compound obtained in Example 9 (0.15 g) in ethanol (25 ml) is added 20% Pd(OH)$_2$/C (0.25 g), and the mixture is stirred at 30° C. under hydrogen pressure (3–4 atms) for 6 hours. The catalyst is removed by filtration, and the filtrate is concentrated under reduced pressure. Water (5 ml) is added to the resulting residue, and the mixture is lyophilized to give the title stereoisomer (72 mg) as a colorless powder.

$[\alpha]_D$-27° (c=0.05, MeOH); M.p. gradually melted at around 60° C.; $^1$H-NMR (DMSO-d$_6$)δ: 0.83–0.87 (m, 6H), 1.03 (d, 3H, J=6.4 Hz), 1.10–1.60 (m, 52H), 1.65–1.81 (m, 1H), 1.83–2.05 (m, 1H), 2.10–2.35 (m, 3H), 2.58 (d, 3H, J=4.5 Hz), 3.35–3.58 (m, 3H), 3.68–3.85 (m, 2H), 3.87 (dd, 1H, J=5.3, 9.7 Hz), 4.15–4.25 (m, 1H), 4.42–4.56 (m, 1H), 4.71 (d, 1H, 3.8 Hz), 5.14 (s, 1H), 7.72 (d, 1H, J=4.6 Hz), 7.80–7.95 (m, 1H), 8.00 (d, 1H, J=7.9 Hz), 12.05 (bs, 1H).

Example 18

Preparation of [N-(2-tetradecylhexadecanoyl)-O-(α-L-fucofuranosyl)-L-seryl]-D-glutamic acid 1-methylamide [α-anomer of the compound (Ib) wherein R$^1$ is 1-tetradecylpentadecyl group, R$^2$ is methylcarbamoyl group, and n is 1]:

To a solution of the compound obtained in Example 10 (0.20 g) in ethanol (30 ml) is added 20% Pd(OH)$_2$/C (0.20 g), and the mixture is stirred at 30° C. under hydrogen pressure (3–4 atms) for 5 hours. The catalyst is removed by filtration, and the filtrate is concentrated under reduced pressure. Water (5 ml) is added to the resulting residue, and the mixture is lyophilized to give the title stereoisomer (79 mg) as a colorless powder.

$[\alpha]_D$-20° (c=0.1, MeOH); M.p. gradually melted at around 110° C.; $^1$H-NMR (DMSO-d$_6$)δ: 0.83–0.87 (m, 6H), 1.01 (d, 3H, J=6.4 Hz), 1.10–1.60 (m, 52H), 1.60–1.78 (m, 1H), 1.85–2.02 (m, 1H), 2.12–2.30 (m, 3H), 2.58 (d, 3H, J=3.5 Hz), 3.40–3.55 (m, 2H), 3.65–3.78 (m, 2H), 3.88 (dd, 1H, J=6.0, 10.2 Hz), 4.10–4.25 (m, 1H), 4.33–4.50 (m, 1H), 4.70 (d, 1H, 4.0 Hz), 5.12 (s, 1H), 7.87 (d, 1H, J=4.8 Hz), 7.96 (d, 1H, J=7.2 Hz), 8.09 (d, 1H, J=7.1 Hz), 12.05 (bs, 1H).

Example 19

Preparation of [N-(2-tetradecylhexadecanoyl)-O-(α-L-fucofuranosyl)-D-seryl]-L-glutamic acid 1-methylamide [α-anomer of the compound (Ib) wherein R$^1$ is 1-tetradecylpentadecyl group, R$^2$ is methylcarbamoyl group, and n is 1]:

To a solution of the compound obtained in Example 11 (0.50 g) in ethanol (50 ml) is added 20% Pd(OH)$_2$/C (0.40 g), and the mixture is stirred at 30° C. under hydrogen pressure (3–4 atms) for 5 hours. The catalyst is removed by filtration, and the filtrate is concentrated under reduced pressure. The resulting residue is dissolved in methanol (10 ml), and thereto is added water (30 ml). The precipitated solid is collected by filtration to give the title stereoisomer (0.29 g) as a colorless powder.

$[\alpha]_D$-21° (c=0.1, MeOH); M.p. 134–138° C.; $^1$H-NMR (DMSO-d$_6$)δ: 0.70–0.95 (m, 6H), 1.03 (d, 3H, J=6.3 Hz), 1.10–1.55 (m, 52H), 1.56–1.80 (m, 1H), 1.80–2.08 (m, 1H), 2.11–2.30 (m, 3H), 2.57 (d, 3H, J=4.5 Hz), 3.40–3.58 (m, 1H), 3.63 (dd, 1H, J=5.1, 10.2 Hz), 3.70–3.85 (m, 3H), 4.10–4.25 (m, 1H), 4.30–4.45 (m, 1H), 4.46 (d, 1H, 4.9 Hz), 4.50–4.70 (m, 1H), 4.75 (d, 1H, J=3.5 Hz), 5.11 (d, 1H, J=5.6 Hz), 7.76 (d, 1H, J=4.5 Hz), 7.83 (d, 1H, J=8.2 Hz), 8.07 (d, 1H, J=7.1 Hz), 12.02 (s, 1H).

Mass spectrum (m/e): 828 (M+H)$^+$ Elementary Analysis for C$_{45}$H$_{85}$N$_3$O$_{10}$.1H$_2$O; Calculated: C, 63.87; H, 10.36; N, 4.97; Found: C, 64.14; H, 10.18; N, 4.73

Example 20

Preparation of [N-(2-tetradecylhexadecanoyl)-O-(α-L-fucofuranosyl)-D-seryl]-D-glutamic acid 1-methylamide [α-anomer of the compound (Ib) wherein R$^1$ is 1-tetradecylpentadecyl group, R$^2$ is methylcarbamoyl group, and n is 1]:

To a solution of the compound obtained in Example 12 (0.22 g) in ethanol (30 ml) is added 20% Pd(OH)$_2$/C (0.20 g), and the mixture is stirred at 30° C. under hydrogen pressure (3–4 atms) for 4 hours. The catalyst is removed by filtration, and the filtrate is concentrated under reduced pressure. Water (5 ml) is added to the resulting residue, and the mixture is lyophilized to give the title stereoisomer (0.13 g) as a colorless powder.

$[\alpha]_D$-12° (c=0.1, MeOH); M.p. 109–113° C.; $^1$H-NMR (DMSO-d$_6$)δ: 0.83–0.88 (m, 6H), 1.02 (d, 3H, J=6.3 Hz), 1.10–1.50 (m, 52H), 1.60–1.80 (m, 1H), 1.80–2.00 (m, 1H), 2.15–2.30 (m, 3H), 2.58 (d, 3H, J=4.5 Hz), 3.40–3.55 (m, 1H), 3.55–3.65 (m, 1H), 3.65–3.85 (m, 2H), 4.15–4.25 (m, 1H), 4.40–4.55 (m, 1H), 4.77 (d, 1H, 3.9 Hz), 5.14 (d, 1H, J=5.0 Hz), 7.69 (d, 1H, J=4.7 Hz), 7.85 (d, 1H, J=7.8 Hz), 8.02 (d, 1H, J=8.2 Hz), 12.00 (bs, 1H).

Example 21

Preparation of [N-(2-tetradecylhexadecanoyl)-O-(L-fucofuranosyl)-L-seryl]-L-glutamic acid [a mixture of α-anomer and β-anomer of the compound (Ib) wherein R$^1$ is 1-tetradecylpentadecyl group, R$^2$ is carboxyl group, and n is 1]:

To a solution of the compound obtained in Example 13 (0.05 g) in ethanol (25 ml) is added 20% Pd(OH)$_2$/C (0.05 g), and the mixture is stirred at 30° C. under hydrogen pressure (3–4 atms) for 15 hours. The catalyst is removed by filtration, and the filtrate is concentrated under reduced pressure. To the resulting residue are added water (2 ml) and dioxane (2 ml), and the mixture is lyophilized to give a mixture of α-anomer and β-anomer of [N-(2-tetradecylhexadecanoyl)-O-(L-fucofuranosyl)-L-seryl]-L-glutamic acid (22 mg, α-anomer: β-anomer=2:1) as a colorless powder.

$[α]_D$ –30° (c=0.1, MeOH); M.p. 57–65° C.; $^1$H-NMR (DMSO-d$_6$)δ: 0.75–0.90 (m), 1.01 (d, J=6.4 Hz), 1.08 (d, J=6.3 Hz), 1.10–1.60 (m), 1.70–1.85 (m), 1.85–2.05 (m), 2.15–2.40 (m), 3.40–3.60 (m), 3.65–3.80 (m), 4.20–4.30 (m), 4.50–4.60 (m), 4.71 (d, J=4.1 Hz), 7.85–8.05 (m).

Elementary Analysis for C$_{44}$H$_{82}$N$_2$O$_{11}$.3H$_2$O; Calculated: C, 60.80; H, 10.20; N, 3.22; Found: C, 60.81; H, 9.90; N, 3.05

Example 22

Preparation of [N-(2-tetradecylhexadecanoyl)-O-(L-fucofuranosyl)-L-seryl]-L-aspartic acid 1-methylamide [a mixture of α-anomer and β-anomer of the compound (Ib) wherein R$^1$ is 1-tetradecylpentadecyl group, R$^2$ is methylcarbamoyl group, and n is 0]:

To a solution of the compound obtained in Example 14 (0.09 g) in ethanol (30 ml) is added 20% Pd(OH)$_2$/C (0.08 g), and the mixture is stirred at 30° C. under hydrogen pressure (3–4 atms) for 14 hours. The catalyst is removed by filtration, and the filtrate is concentrated under reduced pressure. To the resulting residue are added water (1 ml) and dioxane (2 ml), and the mixture is lyophilized to give a mixture of α-anomer and β-anomer of [N-(2-tetradecylhexadecanoyl)-O-(L-fucofuranosyl)-L-seryl]-L-aspartic acid 1-methylamide (40 mg, α-anomer:β-anomer=2:1) as a colorless powder.

M.p. 75–78° C.; $^1$H-NMR (DMSO-d$_6$)δ: 0.83–0.87 (m), 1.03 (d, J=5.8 Hz), 1.09 (d, J=6.1 Hz), 1.10–1.55 (m), 2.10–2.30 (m), 2.57 (d, J=3.3 Hz), 2.60–2.75 (m), 3.15–3.25 (m), 3.40–3.60 (m), 3.60–3.80 (m), 3.90–4.05 (m), 4.40–4.55 (m), 4.60–4.75 (m), 7.50–7.65 (m), 7.95–8.05 (m).

Example 23

Preparation of 4-N-[N-(2-tetradecylhexadecanoyl)-O-(α-L-fucofuranosyl)-L-seryl]aminobutyric acid [α-anomer of the compound (Ib) wherein R$^1$ is 1-tetradecylpentadecyl group, R$^2$ is hydrogen atom, and n is 1]:

To a solution of the compound obtained in Example 15 (0.03 g) in ethanol (20 ml) is added 20% Pd(OH)$_2$/C (0.03 g), and the mixture is stirred at 30° C. under hydrogen pressure (3–4 atms) for 17 hours. The catalyst is removed by filtration, and the filtrate is concentrated under reduced pressure. To the resulting residue are added water (1 ml) and dioxane (1 ml), and the mixture is lyophilized to give 4-N-[N-(2-tetradecylhexadecanoyl)-O-(α-L-fucofuranosyl)-L-seryl]aminobutyric acid (15 mg) as a colorless powder.

$[α]_D$ –16° (c=0.1, MeOH); M.p. 61–67° C.; $^1$H-NMR (DMSO-d$_6$)δ: 0.83–0.87 (m, 6H), 1.01 (d, 3H, J=6.4 Hz), 1.10–1.50 (m, 52H), 1.55–1.70 (m, 2H), 2.19 (t, 2H, J=7.4 Hz), 3.00–3.15 (m, 2H), 3.25–3.35 (m, 1H), 3.40–3.50 (m, 3H), 3.60–3.80 (m, 2H), 3.80–3.90 (m, 1H), 4.40–4.5 (m, 1H), 4.68 (d, 1H, J=4.2 Hz), 7.78 (t, 1H, J=5.4 Hz), 7.90 (d, 1H, J=8.4 Hz).

Example 24

Preparation of 5-N-[N-(2-tetradecylhexadecanoyl)-O-(α-L-fucofuranosyl)-L-seryl]aminovaleric acid [α-anomer of the compound (Ib) wherein R$^1$ is 1-tetradecylpentadecyl group, R$^2$ is hydrogen atom, and n is 2]:

To a solution of the compound obtained in Example 16 (0.06 g) in ethanol (30 ml) is added 20% Pd(OH)$_2$/C (0.06 g), and the mixture is stirred at 30° C. under hydrogen pressure (3–4 atms) for 14 hours. The catalyst is removed by filtration, and the filtrate is concentrated under reduced pressure. To the resulting residue are added water (1 ml) and dioxane (1 ml), and the mixture is lyophilized to give 5-N-[N-(2-tetradecylhexadecanoyl)-O-(α-L-fucofuranosyl)-L-seryl]aminovaleric acid (41 mg) as a colorless powder.

$[α]_D$ –29° (c=0.1, MeOH); M.p. 111–116° C.; $^1$H-NMR (DMSO-d$_6$)δ: 0.83–0.87 (m, 6H), 1.01 (d, 3H, J=6.4 Hz), 1.10–1.55 (m, 52H), 2.19 (t, 2H, J=6.9 Hz), 3.00–3.10 (m, 2H), 3.25–3.35 (m, 1H), 3.35–3.50 (m, 3H), 3.65–3.75 (m, 2H), 3.80–3.85 (m, 1H), 4.30–4.50 (m, 2H), 4.68 (d, 1H, J=4.2 Hz), 7.71 (t, 1H, J=5.5 Hz), 7.90 (d, 1H, J=8.4 Hz).

Elementary Analysis for C$_{44}$H$_{82}$N$_2$O$_9$.1.5H$_2$O; Calculated: C, 65.07; H, 10.80; N, 3.45; Found: C, 65.02; H, 10.43; N, 3.38

Example 25

Preparation of [N-tert-butoxycarbonyl-O-(2,3,4-tri-O-benzyl-α-L-fucofuranosyl)-L-seryl]-D-glutamic acid 1-anilide 5-benzyl ester [α-anomer of the compound (II-3) wherein R$^4$ is phenylcarbamoyl group, and n is 1]:

To Molecular Sieves 4 Å (1.0 g) are added methylene chloride (10 ml), AgOTf (0.77 g) and SnCl$_2$ (0.57 g), and the mixture is cooled to –40~–50° C. under argon atmosphere. To the mixture is added TMU (0.87 g), and then further are added a solution of (2,3,4-tri-O-benzyl)-L-fucofuranosyl fluoride (0.98 g, the compound (VIII)) in methylene chloride (2 ml), and a solution of N-tert-butoxycarbonyl-L-seryl-D-glutamic acid 1-anilide 5-benzyl ester (0.75 g, the stereoisomer of Reference Example 9) in methylene chloride (5 ml), and the mixture is stirred at the same temperature for one hour. The mixture is stirred for 20 hours while it is gradually warmed to room temperature. The reaction mixture is filtered, and the filtrate is washed with a saturated aqueous sodium hydrogen carbonate solution, dried, and concentrated under reduced pressure. The resulting residue is purified by preparative thin layer chromatography (n-hexane:ethyl acetate=1:1), and crystallized from ether to give [N-tert-butoxycarbonyl-O-(2,3,4-tri-O-benzyl-α-L-fucofuranosyl)-L-seryl]-D-glutamic acid 1-anilide 5-benzyl ester (0.46 g) as colorless crystals.

M.p. 135–139° C.; $^1$H-NMR (DMSO-d$_6$)δ: 1.04 (d, 3H, J=6.2 Hz), 1.32 (s, 9H), 1.82–2.00 (m, 1H), 2.00–2.20 (m, 1H), 2.30–2.50 (m, 2H), 3.47–3.58 (m, 1H), 3.58–3.70 (m, 2H), 3.70–3.85 (m, 1H), 4.00 (d, 2H, J=4.6 Hz), 4.32–4.50 (m, 7H), 5.02 (s, 2H), 5.07 (s, 1H), 6.87 (d, 1H, J=6.9 Hz), 7.05 (t, 1H, J=7.3 Hz), 7.14–7.42 (m, 22H), 7.61 (d, 2H, J=7.8 Hz), 8.33 (d, 1H, J=7.5 Hz), 9.93 (s, 1H).

Example 26

Preparation of [N-(2-tetradecylhexadecanoyl)-O-( 2,3,4-tri-O-benzyl-α-L-fucofuranosyl)-L-seryl]-D-glutamic acid 1-anilide 5-benzyl ester [α-anomer of the compound (II-4) wherein R$^1$ is 1-tetradecylpentadecyl group, R$^4$ is phenylcarbamoyl group, and n is 1]:

The compound obtained in Example 25 (0.41 g) is dissolved in methylene chloride (8 ml), and thereto is added with stirring TFA (8 ml) under ice-cooling, and the mixture is stirred for two hours. The reaction mixture is concentrated, and thereto is added chloroform (50 ml). The mixture is washed with a saturated aqueous sodium hydrogen carbonate solution, dried, and concentrated under reduced pressure. The resulting de-protected syrup product is dissolved in DMF (40 ml), and thereto is added 2-tetradecylhexadecanoic acid (0.2 g), and further thereto are added with stirring WSC (0.13 g) and HOBt (0.1 g) under ice-cooling. The mixture is stirred for 22 hours while it is gradually warmed to room temperature. To the reaction solution is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give [N-(2-tetradecylhexadecanoyl)-O-(2,3,4-tri-O-benzyl-α-L-fucofuranosyl)-L-seryl]-D-glutamic acid 1-anilide 5-benzyl ester (0.28 g) as colorless crystals.

M.p. 131–135° C.; $^1$H-NMR (DMSO-d$_6$)δ: 0.75–0.95 (m, 6H), 0.94–1.60 (m, 55H), 1.78–1.96 (m, 1H), 2.00–2.50 (m, 4H), 3.49–3.71 (m, 3H), 3.72–3.88 (m, 1H), 3.94–4.08 (m, 2H), 4.44 (dd, 2H, J=4.1, 11.5 Hz), 4.52–4.70 (m, 5H), 5.00 (s, 1H), 5.04 (d, 1H, J=3.3 Hz), 7.03 (t, 1H, J=7.4 Hz), 7.15–7.41 (m, 22H), 7.69 (d, 2H, J=7.8 Hz), 8.15 (d, 1H, J=6.8 Hz), 8.47 (d, 1H, J=8.0 Hz), 9.80 (s, 1H).

Elementary Analysis for $C_{78}H_{111}N_3O_{10}$; Calculated: C, 74.90; H, 8.94; N, 3.36; Found: C, 74.67; H, 8.97; N, 3.21

Example 27

Preparation of [N-(2-tetradecylhexadecanoyl)-O-(α-L-fucofuranosyl)-L-seryl]-D-glutamic acid 1-anilide [α-anomer of the compound (Ib) wherein $R^1$ is 1-tetradecylpentadecyl group, $R^2$ is phenylcarbamoyl group, and n is 1]:

To a solution of the compound obtained in Example 26 (0.23 g) in ethanol (40 ml) is added 20% Pd(OH)$_2$/C (0.20 g), and the mixture is stirred at 30° C. under hydrogen pressure (3–4 atms) for 7 hours. The catalyst is removed by filtration, and the filtrate is concentrated under reduced pressure. To the resulting residue is added water (5 ml), and the mixture is crystallized to give [N-(2-tetradecylhexadecanoyl)-O-(α-L-fucofuranosyl)-L-seryl]-D-glutamic acid 1-anilide (127 mg).

M.p. 150–153° C.; $^1$H-NMR (DMSO-d$_6$)δ: 0.83–0.87 (m, 6H), 1.00 (d, 3H, J=6.3 Hz), 1.08–1.55 (m, 52H), 1.75–1.91 (m, 1H), 1.98–2.18 (m, 1H), 2.18–2.32 (m, 3H), 3.45–3.60 (m, 2H), 3.69–3.82 (m, 2H), 3.88 (dd, 1H, J=6.6, 10.0 Hz), 4.34–4.54 (m, 2H), 4.72 (d, 1H, J=3.7 Hz), 5.12 (s, 1H), 7.04 (t, 1H, J=7.4 Hz), 7.28 (t, 2H, J=7.6 Hz), 7.68 (d, 1H, J=8.6 Hz), 8.08–8.23 (m, 2H), 12.50 (bs, 1H).

Mass spectrum (m/e): 890 (M+H)$^+$

Example 28

Preparation of sodium salt of [N-(2-tetradecylhexadecanoyl)-O-(α-L-fucofuranosyl)-L-seryl]-D-glutamic acid 1-methylamide [α-anomer of the compound (Ib) wherein $R^1$ is 1-tetradecylpentadecyl group, $R^2$ is methylcarbamoyl group, and n is 1]:

The compound obtained in Example 18 (0.20 g) is dissolved in methanol (30 ml) and water (10 ml), and thereto is added 1N aqueous sodium hydroxide solution (0.12 ml), and the mixture is stirred for five minutes. The mixture is concentrated under reduced pressure to remove the methanol, and lyophilized to give [N-(2-tetradecylhexadecanoyl)-O-(α-L-fucofuranosyl)-L-seryl]-D-glutamic acid 1-methylamide sodium salt (141 mg) as a colorless solid.

M.p. 147–154° C. (decomposed); $^1$H-NMR (DMSO-d$_6$)δ: 0.83–0.87 (m, 6H), 1.01 (d, 3H, J=6.3 Hz), 1.10–1.55 (m, 52H), 1.60–2.05 (m, 4H), 2.10–2.32 (m, 1H), 2.55 (d, 3H, J=3.5 Hz), 3.20–3.35 (m, 2H), 3.40–3.65 (m, 3H), 3.66–3.76 (m, 1H), 3.77–3.86 (m, 1H), 3.86–4.04 (m, 2H), 4.35 (s, 1H), 4.66 (d, 1H, 4.2 Hz), 8.23 (d, 1H, J=7.4 Hz), 9.19 (d, 1H, J=5.8 Hz).

Example 29

Preparation of [N-(2-undecyltridecanoyl)-O-(2,3,4-tri-O-benzyl-(α-L-fucofuranosyl)-D-seryl]-L-glutamic acid 1-methylamide 5-benzyl ester [α-anomer of the compound (II-4) wherein $R^1$ is 1-undecyldodecyl group, $R^4$ is methylcarbamoyl group, and n is 1]:

The compound obtained in Example 3 (0.46 g) is dissolved in methylene chloride (5 ml), and thereto is added with stirring TFA (5 ml) under ice-cooling, and the mixture is stirred for 2.5 hours. The reaction mixture is concentrated, and thereto is added chloroform (100 ml). The mixture is washed with a saturated aqueous sodium carbonate solution, dried, and concentrated under reduced pressure. The resulting de-protected syrup product is dissolved in DMF (15 ml), and thereto is added 2-undecyltridecanoic acid (0.2 g), and further thereto are added with stirring WSC (0.16 g) and HOBt (0.12 g) under ice-cooling. The mixture is stirred for 19 hours while it is gradually warmed to room temperature. To the reaction solution is added ethyl acetate (120 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.38 g) as colorless crystals.

M.p. 117–119° C.; $^1$H-NMR (CDCl$_3$)δ: 0.8–0.95 (m, 6H), 1.1–1.45 (m, 42H), 1.75–2.1 (m, 2H), 2.1–2.3 (m, 1H), 2.3–2.6 (m, 2H), 2.64 (d, 3H, J=4.7 Hz), 3.5–3.7 (m, 2H), 3.81 (dd, 1H, J=5.2, 6.8 Hz), 3.95–4.2 (m, 3H), 4.3–4.7 (m, 8H), 4.94 (d, 1H, J=4.3 Hz), 5.04 (d, 1H, J=12 Hz), 5.1 (d, 1H, J=12 Hz), 6.35 (q, 1H, J=4.6 Hz), 6.82 (d, 1H, J=6.1 Hz), 6.97 (d, 1H, J=8.1 Hz), 7.15–7.4 (m, 20H).

Elementary Analysis for $C_{67}H_{97}N_3O_{10}$; Calculated: C, 72.80; H, 8.87; N, 3.80; Found: C, 72.76; H, 8.88; N, 3.80

Example 30

Preparation of [N-(2-dodecyltetradecanoyl)-O-( 2,3,4-tri-O-benzyl-(α-L-fucofuranosyl)-D-seryl]-L-glutamic acid 1-methylamide 5-benzyl ester [α-anomer of the compound (II-4) wherein $R^1$ is 1-dodecyltridecyl group, $R^4$ is methylcarbamoyl group, and n is 1]:

The compound obtained in Example 3 (0.55 g) is dissolved in chloroform (5 ml), and thereto is added with stirring TFA (5 ml) under ice-cooling, and the mixture is stirred for 3.5 hours. The reaction mixture is concentrated, and thereto is added chloroform (80 ml). The mixture is washed with a saturated aqueous sodium carbonate solution, dried, and concentrated under reduced pressure. The resulting de-protected syrup product is dissolved in DMF (28 ml), and thereto is added 2-dodecyltetradecanoic acid (0.28 g), and further thereto are added with stirring WSC (0.19 g) and HOBt (0.15 g) under ice-cooling. The mixture is stirred for 20 hours while it is gradually warmed to room temperature. To the reaction solution is added ethyl acetate (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.51 g) as colorless crystals.

M.p. 120–122° C.; $^1$H-NMR (CDCl$_3$)δ: 0.8–0.95 (m, 6H), 1.05–1.45 (m, 42H), 1.45–1.65 (m, 2H), 1.75–2.05 (m, 2H), 2.1–2.3 (m, 1H), 2.3–2.5 (m, 2H), 2.65 (d, 3H, J=4.8 Hz), 3.5–3.68 (m, 2H), 3.81 (dd, 1H, J=5.1, 6.8 Hz), 3.99 (dd, 1H, J=5.4, 10.5 Hz), 4.07 (dd, 1H, J=4.3, 7.4 Hz), 4.1–4.2 (m, 1H), 4.3–4.7 (m, 8H), 4.95 (d, 1H, J=4.3 Hz), 5.04 (d, 1H, J=12.4 Hz), 5.1 (d, 1H, J=12.3 Hz), 6.94 (d, 1H, J=7.8 Hz), 7.15–7.4 (m, 20H).

Elementary Analysis for $C_{61}H_{101}N_3O_{10}$; Calculated: C, 73.10; H, 9.01; N, 3.71; Found: C, 73.12; H, 9.10; N, 3.63

Example 31

Preparation of [N-(2-tridecylpentadecanoyl)-O-(2,3,4-tri-O-benzyl-α-L-fucofuranosyl)-D-seryl]-L-glutamic acid 1-methylamide 5-benzyl ester [α-anomer of the compound (II-4) wherein R$^1$ is 1-tridecyltetradecyl group, R$^4$ is methylcarbamoyl group, and n is 1]:

The compound obtained in Example 3 (0.6 g) is dissolved in chloroform (5 ml), and thereto is added with stirring TFA (5 ml) under ice-cooling, and the mixture is stirred for 2 hours. The reaction mixture is concentrated, and thereto is added chloroform (80 ml). The mixture is washed with a saturated aqueous sodium carbonate solution, dried, and concentrated under reduced pressure. The resulting de-protected syrup product is dissolved in DMF (40 ml), and thereto is added 2-tridecylpentadecanoic acid (0.33 g), and further thereto are added with stirring WSC (0.2 g) and HOBt (0.16 g) under ice-cooling. The mixture is stirred for 21 hours while it is gradually warmed to room temperature. To the reaction solution is added ethyl acetate (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=30:1) to give the title stereoisomer (0.32 g) as colorless crystals.

M.p. 110–116° C.; $^1$H-NMR (CDCl$_3$)δ: 0.8–0.95 (m, 6H), 1.05–1.65 (m, 51H), 1.75–2.1 (m, 2H), 2.1–2.3 (m, 1H), 2.3–2.6 (m, 2H), 2.65 (d, 3H, J=4.6 Hz), 3.5–3.7 (m, 2H), 3.75–3.85 (m, 1H), 3.9–4.2 (m, 1H), 4.3–4.75 (m, 7H), 4.95 (d, 1H, J=3.9 Hz), 5.0–5.15 (m, 2H), 6.32 (q, 1H, J=4.8 Hz), 6.73 (d, 1H, J=6.2 Hz), 6.95 (d, 1H, J=8.2 Hz), 7.15–7.4 (m, 20H).

Elementary Analysis for $C_{71}H_{105}N_3O_{10}$; Calculated: C, 73.40; H, 9.14; N, 3.62; Found: C, 73.39; H, 9.16; N, 3.50

Example 32

Preparation of [N-(2-undecyltridecanoyl)-O-(α-L-fucofuranosyl)-D-seryl]-L-glutamic acid 1-methylamide [α-anomer of the compound (Ib) wherein R$^1$ is 1-undecyldodecyl group, R$^2$ is methylcarbamoyl group, and n is 1]:

To a solution of the compound obtained in Example 29 (0.35 g) in ethanol (30 ml) is added 20% Pd(OH)$_2$/C (0.3 g), and the mixture is stirred at room temperature under hydrogen pressure (3–4 atms) for 6 hours. The catalyst is removed by filtration, and the filtrate is concentrated under reduced pressure. To the resulting residue is added ether:n-hexane (1:1), and the mixture is crystallized to give the title stereoisomer (0.22 g) as colorless crystals.

M.p. 141–145° C.; $^1$H-NMR (DMSO-d$_6$)δ: 0.75–0.95 (m, 6H), 1.03 (d, 3H, J=6.4 Hz), 1.1–1.55 (m, 40H), 1.55–1.8 (m, 1H), 1.8–2.05 (m, 1H), 2.08–2.35 (m, 3H), 2.57 (d, 3H, J=4.5 Hz), 3.42–3.6 (m, 1H), 3.62 (dd, 1H, J=5.3, 10.6 Hz), 3.7–3.9 (m, 3H), 4.1–4.3 (m, 1H), 4.3–4.45 (m, 1H), 4.5–4.8 (m, 2H), 5.17 (s, 1H), 7.77 (d, 1H, J=4.7 Hz), 7.89 (d, 1H, J=7.7 Hz), 8.13 (d, 1H, J=7.1 Hz), 12.05 (bs, 1H).

Elementary Analysis for $C_{39}H_{73}N_3O_{10}.1H_2O$; Calculated: C, 61.47; H, 9.92; N, 5.51; Found: C, 61.71; H, 9.82; N, 5.45

Mass spectrum: 744 (M+H)$^+$

Example 33

Preparation of [N-(2-dodecyltetradecanoyl)-O-(α-L-fucofuranosyl)-D-seryl]-L-glutamic acid 1-methylamide [α-anomer of the compound (Ib) wherein R$^1$ is 1-dodecyltridecyl group, R$^2$ is methylcarbamoyl group, and n is 1]:

To a solution of the compound obtained in Example 30 (0.35 g) in ethanol (30 ml) is added 20% Pd(OH)$_2$/C (0.3 g), and the mixture is stirred at 30° C. under hydrogen pressure (3–4 atms) for 4 hours. The catalyst is removed by filtration, and the filtrate is concentrated under reduced pressure. The precipitated crystals are collected by filtration to give the title stereoisomer (0.19 g) as colorless crystals.

M.p. 138–145° C.; $^1$H-NMR (DMSO-d$_6$)δ: 0.75–0.9 (m, 6H), 1.03 (d, 3H, J=6.4 Hz), 1.1–1.55 (m, 40H), 1.55–1.8 (m, 1H), 1.85–2.1 (m, 1H), 2.1–2.35 (m, 3H), 2.57 (d, 3H, J=4.5 Hz), 3.45–3.6 (m, 1H), 3.6–3.7 (m, 1H), 3.7–3.85 (m, 3H), 4.1–4.28 (m, 1H), 4.3–4.42 (m, 1H), 4.42–4.5 (m, 1H), 4.55–4.7 (m, 1H), 4.7–4.8 (m, 1H), 5.05–5.2 (m, 1H), 7.76 (q, 1H, J=4.8 Hz), 7.84 (d, 1H, J=8.2 Hz), 8.08 (d, 1H, J=7.3 Hz).

Elementary Analysis for $C_{41}H_{77}N_3O_{10}.0.5H_2O$; Calculated: C, 63.05; H, 10.07; N, 5.38; Found: C, 62.93; H, 9.85; N, 5.44

Mass spectrum: 772 (M+H)$^+$

Example 34

Preparation of [N-(2-tridecylpentadecanoyl)-O-(α-L-fucofuranosyl)-D-seryl]-L-glutamic acid 1-methylamide [α-anomer of the compound (Ib) wherein R$^1$ is 1-tridecyltetradecyl group, R$^2$ is methylcarbamoyl group, and n is 1]:

To a solution of the compound obtained in Example 31 (0.28 g) in ethanol (30 ml) is added 20% Pd(OH)$_2$/C (0.23 g), and the mixture is stirred at 30° C. under hydrogen pressure (3–4 atms) for 5 hours. The catalyst is removed by filtration, and the filtrate is concentrated under reduced pressure. The resulting residue is crystallized from ether to give the title stereoisomer (0.16 g) as colorless crystals.

M.p. 146–149° C.; $^1$H-NMR (DMSO-d$_6$)δ: 0.75–0.95 (m, 6H), 1.03 (d, 3H, J=6.3 Hz), 1.1–1.55 (m, 48H), 1.55–1.8 (m, 1H), 1.85–2.07 (m, 1H), 2.1–2.35 (m, 3H), 2.57 (d, 3H, J=4.5 Hz), 3.45–3.6 (m, 1H), 3.6–3.7 (m, 1H), 3.7–3.85 (m, 3H), 4.1–4.28 (m, 1H), 4.3–4.45 (m, 1H), 7.76 (q, 1H, J=4.6 Hz), 7.84 (d, 1H, J=8.3 Hz), 8.08 (d, 1H, J=7.0 Hz).

Elementary Analysis for $C_{43}H_{81}N_3O_{10}.0.5H_2O$; Calculated: C, 63.83; H10.21; N, 5.19; Found: C, 63.70; H, 10.10; N, 5.00

Mass spectrum: 800 (M+H)$^+$

Example 35

Preparation of [N-(2-pentadecylheptadecanoyl)-O-( 2,3, 4-tri-O-benzyl-α-L-fucofuranosyl)-D-seryl]-L-glutamic acid 1-methylamide 5-benzyl ester [α-anomer of the compound (II-4) wherein R$^1$ is 1-pentadecylhexadecyl group, R$^4$ is methylcarbamoyl group, and n is 1]:

The compound obtained in Example 3 (0.5 g) is dissolved in chloroform (5 ml), and thereto is added with stirring TFA (5 ml) under ice-cooling, and the mixture is stirred for 3 hours. The reaction mixture is concentrated, and thereto is added ethyl acetate (100 ml). The mixture is washed with a saturated aqueous sodium carbonate solution, dried, and concentrated under reduced pressure. The resulting de-protected syrup product is dissolved in DMF (30 ml), and thereto is added 2-pentadecylheptadecanoic acid (0.28 g), and the mixture is dissolved with heating. The mixture is cooled to room temperature, and further thereto are added with stirring WSC (146 mg) and HOBt (116 mg) under ice-cooling. The mixture is stirred for 4 hours at 50° C., and then stirred at room temperature overnight. To the reaction solution is added ethyl acetate (200 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.42 g) as colorless crystals.

M.p. 117–119° C.; $^1$H-NMR (CDCl$_3$)δ: 0.75–0.95 (m, 6H), 1.05–1.65 (m, 59H), 1.75–2.1 (m, 2H), 2.1–2.3 (m, 1H), 2.3–2.55 (m, 2H), 2.65 (d, 3H, J=4.75 Hz), 3.5–3.7 (m, 2H), 3.81 (dd, 1H, J=5.2, 6.7 Hz), 3.9–4.2 (m, 4H), 4.25–4.75 (m, 7H), 4.96 (d, 1H, J=4.3 Hz), 5.05 (d, 1H, J=12.5 Hz), 5.1 (d, 1H, J=12.4 Hz), 6.28 (q, 1H, J=4.5 Hz), 6.66 (d, 1H, J=6.2 Hz), 6.93 (d, 1H, J=8.0 Hz), 7.15–7.4 (m, 20H).

Example 36

Preparation of [N-(2-pentadecylheptadecanoyl)-O-(α-L-fucofuranosyl)-D-seryl]-L-glutamic acid 1-methylamide [α-anomer of the compound (Ib) wherein R$^1$ is 1-pentadecylhexadecyl group, R$^2$ is methylcarbamoyl group, and n is 1]:

To a solution of the compound obtained in Example 35 (0.68 g) in ethanol (150 ml) is added 20% Pd(OH)$_2$/C (0.6 g), and the mixture is stirred at room temperature under hydrogen pressure (3–4 atms) for 6.5 hours. The catalyst is removed by filtration, and the filtrate is concentrated under reduced pressure. The precipitated solid is collected from water by filtration to give the title stereoisomer (0.39 g) as colorless crystals.

M.p. 141–144° C.; $^1$H-NMR (DMSO-d$_6$)δ: 0.75–0.95 (m, 6H), 1.04 (d, 3H, J=6.4 Hz), 1.1–1.55 (m, 56H), 1.6–1.8 (m, 1H), 1.85–2.05 (m, 1H), 2.1–2.35 (m, 3H), 2.58 (d, 3H, J=4.5 Hz), 3.45–3.6 (m, 1H), 3.6–3.85 (m, 4H), 4.1–4.28 (m, 1H), 4.3–4.45 (m, 2H), 4.56 (bs, 1H), 4.7–4.8 (m, 1H), 5.06 (bs, 1H), 7.72 (q, 1H, J=4.8 Hz), 7.79 (d, 1H, J=8.4 Hz), 8.02 (d, 1H, J=6.9 Hz), 12.0 (bs, 1H).

Mass spectrum: 878 (M+Na)$^+$

Example 37

Preparation of [N-tert-butoxycarbonyl-O-(2,3,4-tri-O-benzyl-α-L-fucopyranosyl)-L-seryl]-L-glutamic acid 1-methylamide 5-benzyl ester [α-anomer of the compound (II-1) wherein R$^4$ is methylcarbamoyl group, and n is 1]:

To Molecular Sieves 4 Å (1.0 g) are added AgOTf (1.2 g), SnCl$_2$ (0.9 g) and chloroform (20 ml), and the mixture is stirred at room temperature for 6 hours under nitrogen atmosphere. The mixture is cooled to −40~−50° C., and thereto is added TMU (1.4 ml), and further thereto are added a solution of (2,3,4-tri-O-benzyl)-L-fucopyranosyl fluoride (1.5 g, the compound (VI)) in chloroform (2 ml), and a solution of N-tert-butoxycarbonyl-L-seryl-L-glutamic acid 1-methylamide 5-benzyl ester (1.0 g, the stereoisomer of Reference Example 1) in chloroform (6 ml), and the mixture is stirred at the same temperature for one hour. The mixture is stirred for 17 hours while it is gradually warmed to room temperature. The reaction mixture is filtered, and the filtrate is concentrated. The resulting residue is purified by silica gel medium-pressure liquid chromatography (n-hexane:ethyl acetate=1:2→2:1) to give the title stereoisomer (0.66 g) as colorless crystals.

[α]$_D$–53° (c=0.17, CHCl$_3$); M.p. 141–142° C.; $^1$H-NMR (CDCl$_3$)δ: 1.09 (d, 3H, J=6.5 Hz), 1.45 (s, 9H), 1.65–1.9 (m, 1H), 2.05–2.55 (m, 3H), 2.74 (d, 3H, J=4.8 Hz), 3.4–3.5 (m, 1H), 3.63 (d, 1H, J=1.6 Hz), 3.75–3.9 (m, 2H), 4.02 (dd, 1H, J=3.6, 10.1 Hz), 4.12–4.28 (m, 2H), 4.35–4.5 (m, 1H), 4.5–4.95 (m, 7H), 5.06 (s, 2H), 6.04 (bs, 1H), 6.33 (bs, 1H), 7.05 (d, 1H, J=8.3 Hz), 7.2–7.4 (m, 20H).

Elementary Analysis for C$_{48}$H$_{59}$N$_3$O$_{11}$·0.5H$_2$O; Calculated: C, 66.80; H, 7.01; N, 4.87; Found: C, 66.99; H, 6.71; N, 4.80

Example 38

Preparation of [N-tert-butoxycarbonyl-O-(2,3,4-tri-O-benzyl-α-L-fucopyranosyl)-L-seryl]-D-glutamic acid 1-methylamide 5-benzyl ester [α-anomer of the compound (II-1) wherein R$^4$ is methylcarbamoyl group, and n is 1]:

To Molecular Sieves 4 Å (1.0 g) are added AgOTf (0.94 g), SnCl$_2$ (0.69 g) and chloroform (10 ml), and the mixture is stirred at room temperature for 5 hours under nitrogen atmosphere. The mixture is cooled to −40~−50° C., and thereto is added TMU (1.06 g), and further thereto are added a solution of (2,3,4-tri-O-benzyl)-L-fucopyranosyl fluoride (1.2 g, the compound (VI)) in chloroform (1 ml), and a solution of N-tert-butoxycarbonyl-L-seryl-D-glutamic acid 1-methylamide 5-benzyl ester (0.8 g, the stereoisomer of Reference Example 2) in chloroform (3 ml), and the mixture is stirred at the same temperature for one hour. The mixture is stirred for 14 hours while it is gradually warmed to room temperature. The reaction mixture is filtered, and the filtrate is concentrated. The resulting residue is purified by silica gel medium-pressure liquid chromatography (n-hexane:ethyl acetate=1:1→1:2) to give the title stereoisomer (1.03 g) as a syrup.

[α]$_D$–43° (c=0.1, CHCl$_3$); $^1$H-NMR (CDCl$_3$)δ: 1.11 (d, 3H, J=6 Hz), 1.45 (s, 9H), 1.8–2.0 (m, 1H), 2.0–2.25 (m, 1H), 2.3–2.6 (m, 2H), 2.71 (d, 3H, J=5 Hz), 3.47 (dd, 1H, J=5, 10 Hz), 3.65 (d, 1H, J=2 Hz), 3.81 (q, 1H, J=7 Hz), 3.92 (dd, 1H, J=3, 10 Hz), 4.03 (dd, 1H, J=4, 10 Hz), 7.0–7.4 (m, 20H).

Example 39

Preparation of [N-tert-butoxycarbonyl-O-(2,3,4-tri-O-benzyl-α-L-fucopyranosyl)-D-seryl]-L-glutamic acid 1-methylamide 5-benzyl ester [α-anomer of the compound (II-1) wherein R$^4$ is methylcarbamoyl group, and n is 1]:

To Molecular Sieves 4 Å (0.5 g) are added AgOTf (0.59 g), SnCl$_2$ (0.43 g) and chloroform (10 ml), and the mixture is stirred at room temperature for 5 hours under nitrogen atmosphere. The mixture is cooled to -40~-50° C., and thereto is added TMU (0.66 g), and further thereto are added a solution of (2,3,4-tri-O-benzyl)-L-fucopyranosyl fluoride (0.75 g, the compound (VI)) in chloroform (1 ml), and a solution of N-tert-butoxycarbonyl-D-seryl-L-glutamic acid 1-methylamide 5-benzyl ester (0.5 g, the stereoisomer of Reference Example 3) in chloroform (3 ml), and the mixture is stirred at the same temperature for one hour. The mixture is stirred for 17 hours while it is gradually warmed to room temperature. The reaction mixture is filtered, and the filtrate is concentrated. The resulting residue is purified by preparative thin layer chromatography (cyclohexane:ethyl acetate 1:1) to give the title stereoisomer (0.38 g) as colorless crystals.

$[\alpha]_D$-59° (c=0.1, CHCl$_3$); M.p. 77–81° C.; $^1$H-NMR (CDCl$_3$)δ: 1.13 (d, 3H, J=6.5 Hz), 1.43 (s, 9H), 1.7–2.1 (m, 1H), 2.1–2.3 (m, 1H), 2.3–2.6 (m, 2H), 2.67 (d, 3H, J=4.8 Hz), 3.5–3.7 (m, 2H), 3.8–4.0 (m, 3H), 4.0–4.25 (m, 2H), 4.25–4.45 (m, 1H), 4.5–5.0 (m, 7H), 5.0–5.2 (m, 2H), 5.5 (bs, 1H), 6.07 (bs, 1H), 7.1–7.45 (m, 20H).

Elementary Analysis for $C_{48}H_{59}N_3O_{11}$; Calculated: C, 67.51; H, 6.96; N, 4.92; Found: C, 67.56; H, 6.94; N, 4.52

Example 40

Preparation of [N-tert-butoxycarbonyl-O-(2,3,4-tri-O-benzyl-α-L-fucopyranosyl)-D-seryl]-D-glutamic acid 1-methylamide 5-benzyl ester [α-anomer of the compound (II-1) wherein $R^4$ is methylcarbamoyl group, and n is 1]:

To Molecular Sieves 4 Å (1.3 g) are added AgOTf (0.93 g), SnCl$_2$ (0.69 g) and chloroform (8 ml), and the mixture is stirred at room temperature for 4 hours under nitrogen atmosphere. The mixture is cooled to -40~-50° C., and thereto is added TMU (0.66 g), and further thereto are added a solution of (2,3,4-tri-O-benzyl)-L-fucopyranosyl fluoride (0.95 g, the compound (VI)) in chloroform (1 ml), and a solution of N-tert-butoxycarbonyl-D-seryl-D-glutamic acid 1-methylamide 5-benzyl ester (0.77 g, the stereoisomer of Reference Example 4) in chloroform (3 ml), and the mixture is stirred at the same temperature for one hour. The mixture is stirred for 20 hours while it is gradually warmed to room temperature. The reaction mixture is filtered, and the filtrate is concentrated. The resulting residue is purified twice by preparative thin layer chromatography (cyclohexane:ethyl acetate=1:2, and 1:1) to give the title stereoisomer (0.33 g) as colorless crystals.

M.p. 109–116° C.; $^1$H-NMR (CDCl$_3$)δ: 1.13 (d, 3H, J=6.5 Hz), 1.44 (s, 9H), 1.6–1.75 (m, 1H), 2.0–2.15 (m, 1H), 2.15–2.4 (m, 2H), 2.71 (d, 3H, J=4.8 Hz), 3.55–3.7 (m, 2H), 3.75–4.0 (m, 3H), 4.07 (dd, 1H, J=3.7, 10.2 Hz), 4.1–4.25 (m, 1H), 4.25–4.4 (m, 1H), 4.6–5.0 (m, 7H), 5.07 (s, 2H), 5.52 (bs, 1H), 6.4 (bs, 1H), 7.1–7.5 (m, 20H).

Example 41

Preparation of [N-(2-tetradecylhexadecanoyl)-O-(2,3,4-tri-O-benzyl-α-L-fucopyranosyl)-L-seryl]-L-glutamic acid 1-methylamide 5-benzyl ester [α-anomer of the compound (II-2) wherein $R^1$ is 1-tetradecylpentadecyl group, $R^4$ is methylcarbamoyl group, and n is 1]:

The compound obtained in Example 37 (0.6 g) is dissolved in chloroform (6 ml), and thereto is added with stirring TFA (6 ml) under ice-cooling, and the mixture is stirred at room temperature for one hour. The reaction mixture is concentrated, and thereto is added ethyl acetate (40 ml). The mixture is washed with a saturated aqueous sodium hydrogen carbonate solution, dried, and concentrated under reduced pressure. The resulting de-protected syrup product is dissolved in DMF (27 ml), and thereto is added 2-tetradecylhexadecanoic acid (0.32 g), and the mixture is dissolved with heating. The mixture is cooled to room temperature, and further thereto are added with stirring WSC (0.18 mg) and HOBt (0.14 mg). The mixture is stirred at room temperature for 17 hours. To the reaction solution is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH= 25:1) to give the title stereoisomer (0.6 g) as colorless crystals.

$[\alpha]_D$-44° (c=0.24, CHCl$_3$); M.p. 133–135° C.; $^1$H-NMR (CDCl$_3$)δ: 0.8–0.95 (m, 6H), 1.13 (d, 3H, J=6.5 Hz), 1.1–1.6 (m, 52H), 1.7–2.0 (m, 2H), 2.0–2.25 (m, 1H), 2.25–2.55 (m, 2H), 2.71 (d, 3H, J=4.8 Hz), 3.37 (dd, 1H, J=5.9, 9.4 Hz), 3.67 (d, 1H, J=1.7 Hz), 3.85–3.95 (m, 2H), 4.06 (dd, 1H, J=3.6, 10.1 Hz), 4.21 (dd, 1H, J=2.8, 9.5 Hz), 4.3–4.45 (m, 1H), 4.5–4.6 (m, 1H), 4.55–4.95 (m, 7H), 5.06 (s, 2H), 6.2–6.3 (m, 1H), 6.82 (d, 1H, J=6.7 Hz), 7.06 (d, 1H, J=8 Hz), 7.15–7.4 (m, 20H).

Elementary Analysis for $C_{73}H_{109}N_3O_{10}$; Calculated: C, 73.76; H, 9.24; N, 3.54; Found: C, 73.61; H, 9.07; N,3.43

Example 42

Preparation of [N-(2-tetradecylhexadecanoyl)-O-(2,3,4-tri-O-benzyl-α-L-fucopyranosyl)-L-seryl]-D-glutamic acid 1-methylamide 5-benzyl ester [α-anomer of the compound (II-2) wherein $R^1$ is 1-tetradecylpentadecyl group, $R^4$ is methylcarbamoyl group, and n is 1]:

The compound obtained in Example 38 (0.52 g) is dissolved in chloroform (4 ml), and thereto is added with stirring a mixture of TFA (2 ml) and chloroform (4 ml) under ice-cooling, and the mixture is stirred at room temperature for two hours. The reaction mixture is concentrated, and thereto is added ethyl acetate (20 ml). The mixture is washed with a saturated aqueous sodium carbonate solution and a saturated aqueous sodium chloride solution, dried, and concentrated under reduced pressure. The resulting de-protected syrup product is dissolved in DMF (10 ml), and thereto is added 2-tetradecylhexadecanoic acid (0.33 g), and the mixture is dissolved with heating. The mixture is cooled to room temperature, and further thereto are added with stirring WSC (128 mg) and HOBt (102 mg). The mixture is stirred at room temperature for 19 hours. To the reaction solution is added chloroform (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH= 25:1) to give the title stereoisomer (330 mg) as colorless crystals.

$[\alpha]_D$-29° (c=0.1, CHCl$_3$); M.p. 119–120° C.; $^1$H-NMR (CDCl$_3$)δ: 0.75–0.95 (m, 6H), 1.1–1.7 (m, 52H), 1.13 (d, 3H, J=6 Hz), 1.75–2.0 (m, 2H), 2.0–2.2 (m, 1H), 2.25–2.6 (m, 2H), 2.73 (d, 3H), J=5 Hz), 3.37 (dd, 1H, J=5, 9 Hz), 3.67 (s, 1H), 3.85 (q, 1H, J=6 Hz), 3.97 (dd, 1H, J=2, 10 Hz), 4.06 (dd, 1H, J=3, 10 Hz), 7.0–7.4 (m, 20H).

Example 43

Preparation of [N-(2-tetradecylhexadecanoyl)-O-(2,3,4-tri-O-benzyl-α-L-fucopyranosyl)-D-seryl]-L-glutamic acid 1-methylamide 5-benzyl ester [α-anomer of the compound (II-2) wherein $R^1$ is 1-tetradecylpentadecyl group, $R^4$ is methylcarbamoyl group, and n is 1]:

The compound obtained in Example 39 (0.31 g) is dissolved in chloroform (7 ml), and thereto is added with stirring TFA (7 ml) under ice-cooling, and the mixture is stirred at room temperature for one hour. The reaction mixture is concentrated, and thereto is added ethyl acetate (20 ml). The mixture is washed with a saturated aqueous sodium carbonate solution, dried, and concentrated under reduced pressure. The resulting syrup product is dissolved in DMF (30 ml), and thereto is added 2-tetradecylhexadecanoic acid (0.17 g), and the mixture is dissolved with heating. The mixture is cooled to room temperature, and further thereto are added with stirring WSC (90 mg) and HOBt (72 mg). The mixture is stirred at room temperature for 14 hours. To the reaction solution is added ethyl acetate (100 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=25:1) to give the title stereoisomer (115 mg) as colorless crystals.

$[\alpha]_D$–44° (c=0.1, CHCl$_3$); M.p. 118–120° C.; $^1$H-NMR (CDCl$_3$)δ: 0.8–0.95 (m, 6H), 1.12 (d, 3H, J=6.5 Hz), 1.15–1.7 (m, 52H), 1.75–1.92 (m, 1H), 1.92–2.1 (m, 1H), 2.1–2.3 (m, 1H), 2.3–2.6 (m, 2H), 2.66 (d, 3H, J=4.8 Hz), 3.45–3.65 (m, 2H), 3.78–3.95 (m, 3H), 4.08 (dd, 1H, J=4.2, 10.2 Hz), 4.15–4.25 (m, 2H), 4.6–5.0 (m, 7H), 5.05 (d, 1H, J=11.9 Hz), 5.1 (d, 1H, J=12.3 Hz), 6.0–6.1 (m, 1H), 6.47 (d, 1H, J=6.7 Hz), 7.15–7.4 (m, 20H).

Elementary Analysis for $C_{73}H_{109}N_3O_{10}$; Calculated: C, 73.76; H, 9.24; N, 3.54; Found: C, 73.48; H, 9.13; N, 3.47

Example 44

Preparation of [N-(2-tetradecylhexadecanoyl)-O-(2,3,4-tri-O-benzyl-α-L-fucopyranosyl)-D-seryl]-D-glutamic acid 1-methylamide 5-benzyl ester [α-anomer of the compound (II-2) wherein $R^1$ is 1-tetradecylpentadecyl group, $R^4$ is methylcarbamoyl group, and n is 1]:

The compound obtained in Example 40 (0.42 g) is dissolved in chloroform (9 ml), and thereto is added with stirring TFA (9 ml) under ice-cooling, and the mixture is stirred for three hours under ice-cooling. The reaction mixture is concentrated, and thereto is added ethyl acetate (40 ml). The mixture is washed with a saturated aqueous sodium carbonate solution, dried, and concentrated under reduced pressure. The resulting residue is purified by preparative thin layer chromatography (chloroform:methanol=10:1) to give the de-protected syrup product. The resulting syrup thus obtained is dissolved in DMF (10 ml), and thereto is added 2-tetradecylhexadecanoic acid (0.18 g), and the mixture is dissolved with heating. To the mixture are added WSC (80 mg) and HOBt (70 mg). The mixture is stirred at 50° C. for 5 minutes, and stirred at room temperature for 14 hours. To the reaction solution is added ethyl acetate (50 ml), and the mixture is washed successively with 0.1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=30:1) to give the title stereoisomer (318 mg) as colorless crystals.

$[\alpha]_D$–19° (c=0.1, CHCl$_3$); M.p. 130–132° C.; $^1$H-NMR (CDCl$_3$)δ: 0.8–0.95 (m, 6H), 1.13 (d, 3H, J=6.5 Hz), 1.1–1.7 (m, 53H), 1.9–2.4 (m, 4H), 2.69 (d, 3H, J=4.8 Hz), 3.56 (dd, 1H, J=9.1, 10.8 Hz), 3.69 (d, 1H, J=1.8 Hz), 3.75–4.0 (m, 3H), 4.1 (dd, 1H, J=3.5, 6.5 Hz), 4.2–4.35 (m, 1H) 4.45–4.55 (m, 1H), 4.63 (d, 1H, J=11.6 Hz), 4.68–4.9 (m, 4H), 4.95 (d, 1H, J=11.6 Hz), 5.03 (d, 1H, J=3.7 Hz), 5.07 (s, 2H), 6.34 (q, 1H, J=4.8 Hz), 6.43 (d, 1H, J=6.1 Hz), 7.1–7.5 (m, 20H).

Elementary Analysis for $C_{73}H_{109}N_3O_{10}$; Calculated: C, 73.76; H, 9.24; N, 3.54; Found: C, 73.51; H, 9.15; N, 3.47

Example 45

Preparation of [N-(2-tetradecylhexadecanoyl)-O-(α-L-fucopyranosyl)-L-seryl]-L-glutamic acid 1-methylamide [α-anomer of the compound (Ia) wherein $R^1$ is 1-tetradecylpentadecyl group, $R^2$ is methylcarbamoyl group, and n is 1]:

To a solution of the compound obtained in Example 41 (100 mg) in ethanol (50 ml) is added 20% Pd(OH)$_2$/C (100 mg), and the mixture is stirred at room temperature under hydrogen pressure (3–4 atms) for 15 hours. The catalyst is removed by filtration, and the filtrate is concentrated under reduced pressure. To the resulting residue is added water (5 ml), and the precipitated solid is collected by filtration to give the title stereoisomer (51 mg) as a colorless powder.

$[\alpha]_D$–45° (c=0.08, MeOH); M.p. 171–173° C.; $^1$H-NMR (DMSO-d$_6$)δ: 0.75–0.95 (m, 6H), 1.06 (d, 3H, J=6.5 Hz), 1.1–1.6 (m, 52H), 1.6–2.0 (m, 2H), 2.1–2.3 (m, 3H), 2.58 (d, 3H, J=4.5 Hz), 3.4–3.6 (m, 3H), 3.74 (q, 1H, J=6.9 Hz), 3.86 (dd, 1H, J=5.7, 9.3 Hz), 4.15–4.4 (m, 3H), 4.45–4.6 (m, 2H), 7.63 (d, 1H, J=8.2 Hz), 7.82 (q, 1H, J=4.4 Hz), 8.09 (d, 1H, J=8.7 Hz).

Example 46

Preparation of [N-(2-tetradecylhexadecanoyl)-O-(α-L-fucopyranosyl)-L-seryl]-D-glutamic acid 1-methylamide [α-anomer of the compound (Ia) wherein $R^1$ is 1-tetradecylpentadecyl group, $R^2$ is methylcarbamoyl group, and n is 1]:

To a solution of the compound obtained in Example 42 (30 mg) in 98% aqueous 1,4-dioxane solution (10 ml) is added 20% Pd(OH)$_2$/C (30 mg), and the mixture is stirred at room temperature under hydrogen pressure (3–4 atms) for 4 hours. The catalyst is removed by filtration, and the filtrate is concentrated under reduced pressure. The resulting residue is dissolved in methanol (2 ml), and further thereto is added water (2 ml). The precipitated solid is collected by filtration to give the title stereoisomer (17 mg) as a colorless powder.

$[\alpha]_D$–40° (c=0.1, MeOH); M.p. 183–187° C.; $^1$H-NMR (DMSO-d$_6$)δ: 0.75–0.95 (m, 6H), 1.05 (d, 3H, J=6.5 Hz), 1.1–1.55 (m, 52H), 1.55–1.75 (m, 1H), 1.75–2.0 (m, 1H), 2.05–2.3 (m, 3H), 2.57 (d, 3H, J=4.5 Hz), 3.3–3.55 (m, 4H), 3.67 (q, 1H, J=6.8 Hz), 3.85 (dd, 1H, J=4.3, 9.2 Hz), 4.1–4.35 (m, 3H), 4.45–4.55 (m, 2H), 7.68 (d, 1H, 8 Hz), 7.86 (q, 1H, J=4.5 Hz), 8.13 (d, 1H, J=7.9 Hz), 11.9 ((bs, 1H).

Elementary Analysis for $C_{45}H_{85}N_3O_{10}$. 1H$_2$O; Calculated: C, 63.87; H, 10.36; N, 4.97; Found: C, 63.65; H, 10.25; N, 4.77

Example 47

Preparation of [N-(2-tetradecylhexadecanoyl)-O-(α-L-fucopyranosyl)-D-seryl]-L-glutamic acid 1-methylamide [α-anomer of the compound (Ia) wherein $R^1$ is 1-tetradecylpentadecyl group, $R^2$ is methylcarbamoyl group, and n is 1]:

To a solution of the compound obtained in Example 43 (80 mg) in ethanol (50 ml) is added 20% Pd(OH)$_2$/C (80 mg), and the mixture is stirred at room temperature under hydrogen pressure (3–4 atms) for 4 hours. The catalyst is removed by filtration, and the filtrate is concentrated under reduced pressure. Water (5 ml) is added to the resulting residue, and the precipitated solid is collected by filtration to give the title stereoisomer (46 mg) as a colorless powder.

[α]$_D$-62° (c=0.1, MeOH); M.p. 179–183° C.; $^1$H-NMR (DMSO-d$_6$)δ: 0.75–0.9 (m, 6H), 1.06 (d, 3H, J=6.4 Hz), 1.1–1.55 (m, 52H), 1.6–1.8 (m, 1H), 1.8–2.1 (m, 1H), 3.1–3.3 (m, 3H), 2.58 (d, 3H, J=4.5 Hz), 3.4–3.6 (m, 3H), 3.6–3.85 (m, 2H), 4.1–4.3 (m, 1H), 4.34 (d, 1H, J=4.5 Hz), 4.4–4.55 (m, 1H), 7.45 (d, 1H, 4.4 Hz), 7.97 (d, 1H, J=7.0 Hz), 8.05 (d, 1H, J=8.0 Hz).

Elementary Analysis for C$_{45}$H$_{85}$N$_3$O$_{10}$; Calculated: C, 65.26; H, 10.34; N, 5.07; Found: C, 64.87; H, 10.27; N, 4.80

Example 48

Preparation of [N-(2-tetradecylhexadecanoyl)-O-(α-L-fucopyranosyl)-D-seryl]-D-glutamic acid 1-methylamide [α-anomer of the compound (Ia) wherein R$^1$ is 1-tetradecylpentadecyl group, R$^2$ is methylcarbamoyl group, and n is 1]:

To a solution of the compound obtained in Example 44 (300 mg) in 98% aqueous 1,4-dioxane solution (100 ml) is added 20% Pd(OH)$_2$/C (300 mg), and the mixture is stirred at room temperature under hydrogen pressure (3–4 atms) for 4 hours. The catalyst is removed by filtration, and the filtrate is concentrated under reduced pressure. The resulting residue is dissolved in methanol (12 ml), and further thereto is added water (12 ml). The precipitated solid is collected by filtration to give the title stereoisomer (202 mg) as a colorless powder.

[α]$_D$-32° (c=0.1, MeOH); M.p. 155–157° C.;

1H-NMR (DMSO-d$_6$)δ: 0.75–0.9 (m, 6H), 1.05 (d, 3H, J=6.5 Hz), 1.1–1.55 (m, 52H), 1.6–2.05 (m, 2H), 2.1–2.3 (m, 3H), 2.57 (d, 3H, J=4.5 Hz), 3.55–3.8 (m, 2H), 4.1–4.25 (m, 1H), 4.4–4.6 (m, 1H), 4.6–4.7 (m, 1H), 7.66 (q, 1H, J=4.4 Hz), 7.83 (d, 1H, J=8.4 Hz), 7.92 (d, 1H, J=8.3 Hz).

Elementary Analysis for C$_{45}$H$_{85}$N$_3$O$_{10}$·1.5H$_2$O; Calculated: C, 63.20; H, 10.37; N, 4.91; Found: C, 63.39; H, 10.35; N, 4.71

Example 49

Preparation of [O-(2,3,4-tri-O-acetyl-β-L-fucopyranosyl)-L-seryl]-L-glutamic acid 1-methylamide 5-benzyl ester [stereoisomer of the compound (III-1) wherein R$^4$ is methylcarbamoyl group, and n is 1]:

To Molecular Sieves 4 Å (1.0 g) are added methylene chloride (8 ml), AgOTf (1.17 g) and SnCl$_2$ (0.87 g), and the mixture is stirred at room temperature for 0.5 hour under argon atmosphere. The mixture is cooled to −20° C., and thereto are added a solution of (2,3,4-tri-O-acetyl)-L-fucopyranosyl fluoride (1.0 g, the compound (VII)) in methylene chloride (3 ml), and a solution of N-tert-butoxycarbonyl-L-seryl-L-glutamic acid 1-methylamide 5-benzyl ester (1.0 g, the stereoisomer of Reference Example 1) in methylene chloride (5 ml), and the mixture is stirred for 12 hours while it is gradually warmed to room temperature. The insoluble materials are removed by filtration, and the filtrate is concentrated under reduced pressure. The resulting residue is purified by preparative thin layer chromatography (chloroform:MeOH=9:1) to give the title stereoisomer (1.0 g) as a syrup, which is used in the subsequent reaction without further purification.

Example 50

Preparation of [O-(2,3,4-tri-O-acetyl-β-L-fucopyranosyl)-L-seryl]-D-glutamic acid 1-methylamide 5-benzyl ester [stereoisomer of the compound (III-1) wherein R$^4$ is methylcarbamoyl group, and n is 1]:

To Molecular Sieves 4 Å (1.0 g) are added methylene chloride (8 ml), AgOTf (1.17 g) and SnCl$_2$ (0.87 g), and the mixture is stirred at room temperature for 0.5 hour under argon atmosphere. The mixture is cooled to −20° C., and thereto are added a solution of (2,3,4-tri-O-acetyl)-L-fucopyranosyl fluoride (1.0 g, the compound (VII)) in methylene chloride (3 ml), and a solution of N-tert-butoxycarbonyl-L-seryl-D-glutamic acid 1-methylamide 5-benzyl ester (1.0 g, the stereoisomer of Reference Example 2) in methylene chloride (5 ml), and the mixture is stirred for 19.5 hours while it is gradually warmed to room temperature. The insoluble materials are removed by filtration, and the filtrate is concentrated under reduced pressure. The resulting residue is purified by preparative thin layer chromatography (chloroform:MeOH=9:1) to give the title stereoisomer (0.91 g) as a syrup.

$^1$H-NMR (CDCl$_3$)δ: 1.20 (d, 3H, J=6.3 Hz), 1.98 (s, 3H), 2.03 (s, 3H), 2.08 (t, 1H, J=2.7 Hz), 2.16 (s, 3H), 2.15–2.35 (m, 1H), 2.38–2.57 (m, 2H), 2.79 (d, 3H, J=4.7 Hz), 3.56 (t, 1H, J=5.1 Hz), 3.72–3.95 (m, 2H), 3.99 (dd, 1H, J=3.8, 9.4 Hz), 4.44 (d, 1H, J=7.6 Hz), 4.39–4.52 (m, 1H), 5.00 (dd, 1H, J=3.3, 10.5 Hz), 5.04–5.18 (m, 3H), 5.23 (d, 1H, J=3.3 Hz), 6.67 (d, 1H, J=4.5 Hz), 7.28–7.40 (m, 5H), 8.00 (d, 1H, J=8.6 Hz).

Example 51

Preparation of [O-(2,3,4-tri-O-acetyl-β-L-fucopyranosyl)-D-seryl]-L-glutamic acid 1-methylamide 5-benzyl ester [stereoisomer of the compound (III-1) wherein R$^4$ is methylcarbamoyl group, and n is 1]:

To Molecular Sieves 4 Å (1.0 g) are added methylene chloride (10 ml), AgOTf (1.41 g) and SnCl$_2$ (1.04 g), and the mixture is stirred at room temperature for 0.5 hour under argon atmosphere. The mixture is cooled to −20° C., and thereto are added a solution of (2,3,4-tri-O-acetyl)-L-fucopyranosyl fluoride (1.2 g, the compound (VII)) in methylene chloride (3 ml), and a solution of N-tert-butoxycarbonyl-D-seryl-L-glutamic acid 1-methylamide 5-benzyl ester (1.2 g, the stereoisomer of Reference Example 3) in methylene chloride (5 ml), and the mixture is stirred for 21 hours while it is gradually warmed to room temperature. The insoluble materials are removed by filtration, and the filtrate is concentrated under reduced pressure. The resulting residue is purified by preparative thin layer chromatography (chloroform:MeOH=9:1) to give the title stereoisomer (1.24 g) as a syrup.

$^1$H-NMR (CDCl$_3$)δ: 1.20 (d, 3H, J=6.4 Hz), 1.99 (s, 3H), 2.07 (s, 3H), 2.13 (s, 3H), 2.15–2.40 (m, 3H), 2.40–2.60 (m, 2H), 2.80 (d, 3H, J=4.7 Hz), 3.49–3.62 (m, 1H), 3.70 (dd, 1H, J=3.8, 13.6 Hz), 3.76–3.88 (m, 1H), 4.02–4.16 (m, 1H), 4.95–5.20 (m, 3H), 5.23 (d, 1H, J=2.6 Hz), 6.78 (d, 1H, J=4.7 Hz), 7.35 (s, 5H), 7.87 (d, 1H, J=8.2 Hz).

Example 52

Preparation of [O-(2,3,4-tri-O-acetyl-β-L-fucopyranosyl)-D-seryl]-D-glutamic acid 1-methylamide 5-benzyl ester [stereoisomer of the compound (III-1) wherein R$^4$ is methylcarbamoyl group, and n is 1]:

To Molecular Sieves 4 Å (1.0 g) are added methylene chloride (8 ml), AgOTf (1.17 g) and SnCl$_2$ (0.87 g), and the mixture is stirred at room temperature for 0.5 hour under argon atmosphere. The mixture is cooled to −20° C., and thereto are added a solution of (2,3,4-tri-O-acetyl)-L-fucopyranosyl fluoride (1.0 g, the compound (VII)) in methylene chloride (3 ml), and a solution of N-tert-butoxycarbonyl-D-seryl-D-glutamic acid 1-methylamide 5-benzyl ester (1.0 g, the stereoisomer of Reference Example 4) in methylene chloride (5 ml), and the mixture is stirred for 16 hours while it is gradually warmed to room temperature. The insoluble materials are removed by filtration, and the filtrate is concentrated under reduced pressure. The resulting residue is purified by preparative thin layer chromatography (chloroform:MeOH=9:1) to give the title stereoisomer (0.95 g) as a syrup.

$^1$H-NMR (CDCl$_3$)δ: 1.18 (d, 3H, J=6.4 Hz), 1.99 (s, 3H), 2.05 (s, 3H), 2.12 (s, 3H), 2.35–2.55 (m, 2H), 2.76 (d, 3H, J=4.6 Hz), 3.50–3.66 (m, 1H), 3.74–3.96 (m, 3H), 4.37–4.55 (m, 1H), 4.51 (d, 1H, J=7.6 Hz), 5.02 (dd, 1H, 3.4, 10.4 Hz), 5.10 (s, 2H), 5.21 (d, 1H, J=3.2 Hz), 7.08 (q, 1H, J=4.8 Hz), 7.25–7.38 (m, 5H), 7.93 (d, 1H, J=8.4 Hz).

Example 53

Preparation of [N-(2-tetradecylhexadecanoyl)-O-(2,3,4-tri-O-acetyl-β-L-fucopyranosyl)-L-seryl]-L-glutamic acid 1-methylamide 5-benzyl ester [stereoisomer of the compound (III-2) wherein R$^1$ is 1-tetradecylpentadecyl group, R$^4$ is methylcarbamoyl group, and n is 1]:

The compound obtained in Example 49 (1.0 g) and 2-tetradecylhexadecanoic acid (0.74 g) are dissolved in DMF (5 ml) with heating, and the mixture is cooled to room temperature. To the mixture are added WSC (0.47 g) and HOBt (0.25 g), and the mixture is stirred at room temperature for 12 hours. To the reaction solution is added chloroform (50 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=15:1) to give the title stereoisomer (0.57 g) as colorless crystals.

$^1$H-NMR (CDCl$_3$)δ: 0.85–0.90 (m, 6H), 1.19–1.30 (m, 55H), 1.38–1.57 (m, 2H), 1.70 (s, 2H), 1.99 (s, 3H), 2.08 (s, 3H), 2.11 (s, 3H), 2.51–2.59 (m, 2H), 2.84 (d, 3H, J=4.7 Hz), 3.78–3.85 (m, 2H), 3.94 (dd, 1H, J=4.6, 9.0 Hz), 4.41–4.54 (m, 2H), 4.47 (d, 1H, J=7.2 Hz), 4.96–5.10 (m, 2H), 5.12 (S, 2H), 5.24–5.29 (m, 1H), 6.50 (d, 1H, J=6.3 Hz), 6.72 (d, 1H, J=4.7 Hz), 6.94 (d, 1H, J=8.3 Hz), 7.34 (s, 5H).

Example 54

Preparation of [N-(2-tetradecylhexadecanoyl)-O-(2,3,4-tri-O-acetyl-β-L-fucopyranosyl)-L-seryl]-D-glutamic acid 1-methylamide 5-benzyl ester [stereoisomer of the compound (III-2) wherein R$^1$ is 1-tetradecylpentadecyl group, R$^4$ is methylcarbamoyl group, and n is 1]:

The compound obtained in Example 50 (0.91 g) and 2-tetradecylhexadecanoic acid (0.74 g) are dissolved in DMF (50 ml) with heating, and the mixture is cooled to room temperature. To the mixture are added WSC (0.43 g) and HOBt (0.34 g), and the mixture is stirred at room temperature for 18 hours. To the reaction solution is added ethyl acetate (150 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (0.96 g) as a syrup.

$^1$H-NMR (CDCl$_3$)δ: 0.80–1.00 (m, 6H), 1.19 (d, 3H, J=6.4 Hz), 1.20–1.38 (m, 52H), 1.38–1.66 (m, 2H), 1.70 (s, 2H), 1.98 (s, 3H), 2.07 (s, 3H), 2.13 (s, 3H), 2.17–2.40 (m, 2H), 2.79 (d, 3H, J=4.7 Hz), 3.74–3.92 (m, 2H), 3.99 (dd, 1H, J=4.4, 9.4 Hz), 4.37–4.56 (m, 2H), 4.49 (d, 1H, J=7.3 Hz), 4.95–5.20 (m, 4H), 5.20–5.30 (m, 1H), 6.44 (d, 1H, J=5.6 Hz), 6.96 (d, 1H, J=7.9 Hz), 7.35 (s, 5H).

Example 55

Preparation of [N-(2-tetradecylhexadecanoyl)-O-(2,3,4-tri-O-acetyl-β-L-fucopyranosyl)-D-seryl]-L-glutamic acid 1-methylamide 5-benzyl ester [stereoisomer of the compound (III-2) wherein R$^1$ is 1-tetradecylpentadecyl group, R$^4$ is methylcarbamoyl group, and n is 1]:

The compound obtained in Example 51 (1.20 g) and 2-tetradecylhexadecanoic acid (0.89 g) are dissolved in DMF (50 ml) with heating, and the mixture is cooled to room temperature. To the mixture are added WSC (0.57 g) and HOBt (0.45 g), and the mixture is stirred at room temperature for 16.5 hours. To the reaction solution is added ethyl acetate (120 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give the title stereoisomer (1.20 g) as a syrup.

$^1$H-NMR (CDCl$_3$)δ: 0.80–0.95 (m, 6H), 0.96–1.68 (m, 60H), 1.99 (s, 3H), 2.04 (s, 3H), 2.10 (s, 3H), 2.40–2.64 (m, 2H), 2.75 (d, 3H, J=4.7 Hz), 3.78 (dd, 1H, 3.3, 11.0 Hz), 3.83–4.05 (m, 2H), 4.40–4.67 (m, 2H), 4.59 (d, 1H, J=7.7 Hz), 5.02 (dd, 1H, J=3.3, 10.4 Hz), 5.06–5.20 (m, 3H), 5.25 (d, 1H, J=3.2 Hz), 6.62 (d, 1H, J=8.2 Hz), 6.70 (d, 1H, J=4.8 Hz), 7.20–7.42 (m, 5H).

Example 56

Preparation of [N-(2-tetradecylhexadecanoyl)-O-(2,3,4-tri-O-acetyl-β-L-fucopyranosyl)-D-seryl]-D-glutamic acid 1-methylamide 5-benzyl ester [stereoisomer of the compound (III-2) wherein R$^1$ is 1-tetradecylpentadecyl group, R$^4$ is methylcarbamoyl group, and n is 1]:

The compound obtained in Example 52 (0.94 g) and 2-tetradecylhexadecanoic acid (0.77 g) are dissolved in DMF (50 ml) with heating, and the mixture is cooled to room temperature. To the mixture are added WSC (0.44 g) and HOBt (0.35 g), and the mixture is stirred at room temperature for 20 hours. To the reaction solution is added ethyl acetate (150 ml), and the mixture is washed successively with 1N hydrochloric acid, a saturated aqueous sodium hydrogen carbonate solution, and a saturated aqueous sodium chloride solution, dried, and concentrated under reduced pressure. The precipitated solid is collected by filtration from n-hexane:ether (3:1) to give the title stereoisomer (0.83 g) as colorless crystals.

M.p. 103–105° C.; $^1$H-NMR (CDCl$_3$)δ: 0.80–0.95 (m, 6H), 1.05–1.75 (m, 60H), 1.99 (s, 3H), 2.05 (s, 3H), 2.11 (s, 3H), 2.20–2.42 (m, 1H), 2.43–2.63 (m, 2H), 2.74–2.80 (m, 1H), 2.84 (d, 3H, 4.7 Hz), 3.79 (dd, 1H, J=8.5, 11.2 Hz), 3.86–3.97 (m, 1H), 3.98–4.08 (m, 1H), 4.37–4.52 (m, 1H), 4.50–4.73 (m, 1H), 4.63 (d, 1H, J=7.7 Hz), 4.99 (dd, 1H J=3.2, 10.4 Hz), 5.04–5.07 (m, 3H), 5.25 (d, 1H, J=2.7 Hz), 6.46 (d, 1H, J=5.9 Hz), 6.65 (d, 1H, J=4.8 Hz), 7.27–7.42 (m, 5H).

Example 57

Preparation of [N-(2-tetradecylhexadecanoyl)-O-(β-L-fucopyranosyl)-L-seryl]-L-glutamic acid 1-methylamide

[stereoisomer of the compound (Ia(β)) wherein $R^1$ is 1-tetradecylpentadecyl group, $R^2$ is methylcarbamoyl group, and n is 1]:

To a solution of the compound obtained in Example 53 (0.3 g) in methanol (40 ml) is added Pd/C (0.1 g), and the mixture is stirred at room temperature under hydrogen atmosphere for one hour. The catalyst is removed by filtration, and the filtrate is concentrated under reduced pressure. The resulting residue is dissolved in methanol (30 ml), and further thereto is added a 28% NaOMe/methanol (1.5 ml). The mixture is stirred at room temperature for 0.5 hour, and thereto is added Dowex 50W-X8 (4.0 g). The mixture is stirred for three minutes, and the insoluble materials are removed by filtration. The filtrate is concentrated under reduced pressure, and the precipitated solid is collected by filtration from water to give the title stereoisomer (145 mg) as a colorless powder.

$[\alpha]_D$ $-9°$ (c=0.1, MeOH); M.p. gradually melted at around 160° C.; $^1$H-NMR (DMSO-$d_6$)δ: 0.82–0.87 (m, 6H), 1.13 (d, 3H, J=6.4 Hz), 1.18–1.41 (m, 52H), 1.65–1.73 (m, 1H), 1.83–1.93 (m, 1H), 2.12–2.19 (m, 3H), 2.53 (d, 3H, J=4.5 Hz), 3.34–3.58 (m, 3H), 3.68–3.75 (m, 1H), 4.06–4.15 (m, 2H), 4.38–4.48 (m, 2H), 4.70 (s, 1H), 7.54 (d, 1H, J=4.7 Hz), 7.87–7.95 (m, 2H), 12.01 (bs, 1H).

Mass spectrum (m/e): 828 (M+H)$^+$ Elementary Analysis for $C_{45}H_{85}N_3O_{10} \cdot 2H_2O$; Calculated: C, 62.54; H, 10.38; N, 4.86; Found: C, 62.82; H, 10.01; N, 4.65

Example 58

Preparation of [N-(2-tetradecylhexadecanoyl)-O-(β-L-O-fucopyranosyl)-L-seryl]-D-glutamic acid 1-methylamide [stereoisomer of the compound [Ia(β)] wherein $R^1$ is 1-tetradecylpentadecyl group, $R^2$ is methylcarbamoyl group, and n is 1]:

To a solution of the compound obtained in Example 54 (0.4 g) in ethanol (30 ml) is added Pd/C (0.1 g), and the mixture is stirred at room temperature for two hours under hydrogen atmosphere. The catalyst is removed by filtration, and the filtrate is concentrated under reduced pressure. The resulting residue is dissolved in methanol (30 ml), and thereto is added 28% NaOMe/methanol solution (0.15 g), and the mixture is stirred at room temperature for 0.5 hour. To the mixture is added Dowex 50W-X8 (10 g), and the mixture is stirred for 3 minutes. The insoluble materials are removed by filtration, and the filtrate is concentrated under reduced pressure. The precipitated solid is collected from water by filtration to give the title stereoisomer (0.3 g) as a colorless powder.

$[\alpha]_D$ $+5°$ (c=0.1, MeOH); M.p. 198–199° C.; $^1$H-NMR (DMSO-$d_6$)δ: 0.70–0.93 (m, 6H), 0.95–1.55 (m, 55H), 1.55–1.80 (m, 1H), 1.80–2.04 (m, 2H), 2.06–2.30 (m, 4H), 2.57 (d, 3H, J=4.3 Hz), 3.40–3.68 (m, 2H), 3.70–3.89 (m, 1H), 4.00–4.24 (m, 2H), 4.13 (d, 1H, J=6.9 Hz), 4.23–4.47 (m, 2H), 4.68 (s, 1H), 7.77 (d, 1H, J=4.6 Hz), 7.99 (d, 1H, J=6.7 Hz), 8.02 (d, 1H, J=8.0 Hz), 12.10 (s, 1H).

Mass spectrum (m/e): 828 (M+H)$^+$ Elementary Analysis for $C_{45}H_{85}N_3O_{10} \cdot 1.5H_2O$; Calculated: C, 63.20; H, 10.37; N, 4.91; Found: C, 63.25; H, 10.10; N, 4.69

Example 59

Preparation of [N-(2-tetradecylhexadecanoyl)-O-(β-L-fucopyranosyl)-D-seryl]-L-glutamic acid 1-methylamide [stereoisomer of the compound [(Ia(α)] wherein $R^1$ is 1-tetradecylpentadecyl group, $R^2$ is methylcarbamoyl group, and n is 1]:

To a solution of the compound obtained in Example 55 (0.25 g) in ethanol (30 ml) is added Pd/C (50 mg), and the mixture is stirred at room temperature under hydrogen atmosphere for two hours. The catalyst is removed by filtration, and the filtrate is concentrated under reduced pressure. The resulting residue is dissolved in methanol (20 ml), and thereto is added 28% NaOMe/methanol solution (74 mg), and the mixture is stirred at room temperature for 0.5 hour. To the mixture is added Dowex 50W-X8 (10 g), and the mixture is stirred for 3 minutes. Chloroform (10 ml) is added to the mixture, and the insoluble materials are removed by filtration, and the filtrate is concentrated under reduced pressure. The precipitated solid is collected from water by filtration to give the title stereoisomer (0.13 g) as a colorless powder.

$[\alpha]_D$ $-4°$ (c=0.1, MeOH); M.p. gradually melted ar around 163° C.; $^1$H-NMR (DMSO-$d_6$)δ: 0.80–0.90 (m, 6H), 1.14 (d, 3H, J=6.4 Hz), 0.95–1.55 (m, 52H), 1.60–1.80 (m, 1H), 1.80–2.08 (m, 1H), 2.16–2.36 (m, 3H), 2.58 (d, 3H, J=4.3 Hz), 3.42–3.60 (m, 3H), 3.82–4.00 (m, 1H), 4.08 (d, 1H, J=6.8Hz), 4.10–4.28 (m, 1H), 4.27–4.50 (m, 2H), 4.69 (s, 1H), 4.83 (s, 1H), 7.80 (d, 1H, J=4.6 Hz), 7.89 (d, 1H, J=8.0 Hz), 8.00 (d, 1H, J=7.3 Hz), 12.00 (s, 1H).

Mass spectrum (m/e): 828 (M+H)$^+$ Elementary Analysis for $C_{45}H_{85}N_3O_{10} \cdot 1.5H_2O$; Calculated: C, 63.20; H, 10.37; N, 4.91; Found: C, 63.45; H, 10.13; N, 4.59

Example 60

Preparation of [N-(2-tetradecylhexadecanoyl)-O-(β-L-fucopyranosyl)-D-seryl]-D-glutamic acid 1-methylamide [stereoisomer of the compound [(Ia(β)] wherein $R^1$ is 1-tetradecylpentadecyl group, $R^2$ is methylcarbamoyl group, and n is 1]:

To a solution of the compound obtained in Example 56 (0.3 g) in ethanol (30 ml) is added Pd/C (50 mg), and the mixture is stirred at room temperature for 1.5 hour under hydrogen atmosphere. The catalyst is removed by filtration, and the filtrate is concentrated under reduced pressure. The resulting residue is dissolved in methanol (20 ml), and thereto is added 28% NaOMe/methanol solution (0.11 g), and the mixture is stirred at room temperature for 0.5 hour. To the mixture is added Dowex 50W-X8 (10 g), and the mixture is stirred for 3 minutes. The insoluble materials are removed by filtration, and the filtrate is concentrated under reduced pressure. The precipitated solid is collected from water by filtration to give the title stereoisomer (0.16 g) as a colorless powder.

$[\alpha]_D$ $+6°$ (c=0.1, MeOH); M.p. gradually melted ar around 147° C.; $^1$H-NMR (DMSO-$d_6$)δ: 0.80–0.90 (m, 6H), 0.95–1.60 (m, 55H), 1.60–1.82 (m, 1H), 1.82–2.07 (m, 1H), 2.08–2.36 (m, 3H), 2.59 (d, 3H, J=4.5 Hz), 3.46–3.85 (m, 3H), 3.94 (dd, 1H, J=4.6, 9.8 Hz), 4.07 (d, 1H, J=7.3 Hz), 4.12–4.30 (m, 1H), 4.30–4.66 (m, 2H), 4.67–4.80 (m, 1H), 7.56 (d, 1H, J=4.7 Hz), 7.92 (d, 1H, J=7.4 Hz), 7.98 (d, 1H, J=8.2 Hz), 12.10 (s, 1H).

Mass spectrum (m/e): 828 (M+H)$^+$ Elementary Analysis for $C_{45}H_{85}N_3O_{10} \cdot 1.5H_2O$; Calculated: C, 63.20; H, 10.37; N, 4.91; Found: C, 63.49; H, 10.00; N, 4.67

Example 61

Preparation of [N-(t-butoxycarbonyl)-S-(2,3,4-tri-O-acetyl-α-L-fucopyranosyl)-L-cysteinyl]-L-glutamic acid 1-methylamide 5-benzyl ester [stereoisomer of the compound (IV-1) wherein $R^4$ is methylcarbamoyl group, and n is 1]:

(1) [N-(t-butoxycarbonyl)-S-(2,3,4-tri-O-acetyl-α-L-fucopyranosyl)-L-cysteine [stereoisomer of the compound (X1)]:

2,3,4-Tri-O-acetyl-1-thio-α-L-fucopyranose [0.49 g, the compound (IX)] is dissolved in DMF (2 ml), and thereto is added with stirring 60% sodium hydride (64 mg) under ice-cooling. Three minutes thereafter, [N-(t-butoxycarbonyl)-L-serine β-lactone [0.2 g, stereoisomer of the compound (X)] is added to the mixture. The mixture is stirred for 5 minutes, and stirred at room temperature for one hour. The reaction mixture is made weak-acidic with diluted hydrochloric acid, and the mixture is extracted with ethyl acetate. The organic layer is washed with water and a saturated aqueous sodium chloride solution, dried, and concentrated under reduced pressure. The resulting residue is purified by silica gel medium-pressure liquid chromatography (chloroform: methanol=20:1) to give [N-(t-butoxycarbonyl)-S-(2,3,4-tri-O-acetyl-α-L-fucopyranosyl)]-L-cysteine (0.18 g) as a yellow solid.

$^1$H-NMR (DMSO-d$_6$)δ: 1.07 (d, 3H, J=6 Hz), 1.38 (s, 9H), 1.95 (s, 3H), 2.01 (s, 3H), 2.14 (s, 3H), 2.72 (dd, 1H, J=9, 13 Hz), 2.92 (dd, 1H, J=5, 13 Hz), 3.96 (b, 1H), 4.3–4.5 (m, 1H), 5.05–5.2 (m, 3H), 5.60 (d, 1H, J=5 Hz).

(2) [N-(t-butoxycarbonyl)-S-(2,3,4-tri-O-acetyl-α-L-fucopyranosyl)-L-cysteinyl]-L-glutamic acid 1-methylamide 5-benzyl ester:

N-[(t-Butoxycarbonyl)-L-glutamic acid 1-methylamide 5-benzyl ester [0.55 g, S-isomer of the compound (XV) wherein R$^3$ is methyl group, and n is 1] is dissolved in methylene chloride (8 ml), and thereto is added TFA (4 ml). The mixture is stirred at room temperature for one hour, and the reaction mixture is concentrated to give the de-protected product [0.81 g, stereoisomer of the compound (XIIa) wherein R$^3$ is methyl group, and n is 1] in the form of TFA salt. The TFA salt of the de-protected product thus obtained is dissolved in DMF (3 ml), and to the mixture are added with stirring diisopropylethylamine (0.97 ml), HOBt (0.31 g), a solution of the compound obtained in the above (1) (0.77 g) in DMF (6 ml), and WSC (0.39 g) under ice-cooling, and the mixture is stirred at room temperature for 18.5 hours. The reaction mixture is poured to ice-water (100 ml), and the mixture is extracted three times with ethyl acetate, and the extract is washed with water, dried, and concentrated under reduced pressure. The resulting residue is purified by silica gel medium-pressure liquid chromatography (chloroform:MeOH=100:0→300:1) to give [N-(t-butoxycarbonyl)-S-(2,3,4-tri-O-acetyl-α-L-fucopyranosyl)-L-cysteinyl]-L-glutamic acid 1-methylamide 5-benzyl ester (0.88 g) as a syrup.

$^1$H-NMR (CDCl$_3$)δ: 1.19 (d, 3H, J=6.5 Hz), 1.45 (s, 9H), 1.99 (s, 3H), 2.06 (s, 3H), 2.16 (s, 3H), 2.35–2.68 (m, 2H), 2.75 (dd, 1H, J=7.9, 13.8 Hz), 2.79 (d, 3H, J=4.8 Hz), 3.06 (dd, 1H, J=5.1, 13.7 Hz), 4.1–4.27 (m, 1H), 4.3–4.5 (m, 2H), 5.13 (s, 2H), 5.1–5.32 (m, 3H), 5.66 (d, 1H, J=5.5 Hz), 6.5 (bs, 1H), 7.17 (d, 1H, J=7.9 Hz), 7.3–7.45 (m, 5H).

Example 62

Preparation of [N-(t-butoxycarbonyl)-S-(2,3,4-tri-O-acetyl-α-L-fucopyranosyl)-L-cysteinyl]-D-glutamic acid 1-methylamide 5-benzyl ester [stereoisomer of the compound (IV-1) wherein R$^4$ is methylcarbamoyl group, and n is 1]:

[N-(t-Butoxycarbonyl)-D-glutamic acid 1-methylamide 5-benzyl ester [1.2 g, R-isomer of the compound (XV) wherein R$^3$ is methyl group, and n is 1] is dissolved in methylene chloride (18 ml), and thereto is added TFA (9 ml). The mixture is stirred at room temperature for one hour, and the reaction mixture is concentrated to give the de-protected product [1.95 g, R-isomer of the compound (XIIa) wherein R$^3$ is methyl group, and n is 1] in the form of TFA salt. The TFA salt of the de-protected product thus obtained is dissolved in DMF (7 ml), and thereto are added with stirring diisopropylethylamine (2.5 ml), HOBt (0.68 g), the compound (1.7 g) obtained in Example 61 (1) and WSC (0.85 g) under ice-cooling. The mixture is stirred at room temperature for 20.5 hours, and the reaction mixture is poured into ice-water (170 ml). The mixture is extracted three times with ethyl acetate, and the extract is washed with water, dried, and concentrated under reduced pressure. The resulting residue is purified by silica gel medium-pressured liquid chromatography (chloroform: MeOH = 100:0→500:1→300:1→200:1) to give [N-(t-butoxycarbonyl)-S-(2,3,4-tri-O-acetyl-α-L-fucopyranosyl)-L-cysteinyl]-D-glutamic acid 1-methylamide 5-benzyl ester (1.52 g) as a syrup.

$^1$H-NMR (CDCl$_3$)δ: 1.16 (d, 3H, J=6.4 Hz), 1.44 (s, 9H), 1.99 (s, 3H), 2.06 (s, 3H), 2.16 (s, 3H), 2.35–2.6 (m, 2H), 2.76 (d, 3H, J=4.7 Hz), 2.75–2.9 (m, 1H), 3.02 (dd, 1H, J=5.1, 13.8 Hz), 4.1–4.2 (m, 1H), 4.3–4.55 (m, 2H), 5.12 (s, 2H), 5.15–5.3 (m, 3H), 5.46 (d, 1H, J=6.0 Hz), 5.67 (d, 1H, J=5.5 Hz), 6.88 (bs, 1H), 7.3–7.4 (m, 5H).

Example 63

Preparation of [N-(t-butoxycarbonyl)-S-(2,3,4-tri-O-acetyl-α-L-fucopyranosyl)-D-cysteinyl]-L-glutamic acid 1-methylamide 5-benzyl ester [stereoisomer of the compound (IV-1) wherein R$^4$ is methylcarbamoyl group, and n is 1]:

(1) [N-(t-butoxycarbonyl)-S-(2,3,4-tri-O-acetyl-α-L-fucopyranosyl)-D-cysteine [stereoisomer of the compound (X1)]:

N-(t-Butoxycarbonyl)-D-serine β-lactone [1.50 g, stereoisomer of the compound (X)] and 2,3,4-tri-O-acetyl-1-thio-α-L-fucopyranose [2.45 g, the compound (IX)] are dissolved in DMF (15 ml). To the mixture is added with stirring 60% sodium hydride (0.32 g) under ice cooling, and the mixture is stirred for 40 minutes, and further stirred at room temperature for 30 minutes. To the reaction mixture is added ice-water (50 ml), and the pH value of the mixture is adjusted to pH 3 with aqueous potassium hydrogen sulfate solution. The reaction solution is extracted with ethyl acetate, and the organic layer is washed with water and a saturated aqueous sodium chloride solution, dried, and concentrated under reduced pressure. The resulting residue is purified by silica gel medium-pressure liquid chromatography (chloroform:ethanol=10:1) to give [N-(t-butoxycarbonyl)-S-(2,3,4-tri-O-acetyl-α-L-fucopyranosyl)-D-cysteine (2.0 g).

$^1$H-NMR (CDCl$_3$)δ: 1.22 (d, 3H, J=7 Hz), 1.46 (s, 9H), 2.00 (s, 3H), 2.09 (s, 3H), 2.18 (s, 3H), 2.99 (dd, 1H, J=4, 15 Hz), 3.24 (dd, 1H, J=5, 14 Hz), 4.4–4.55 (m, 1H), 4.55–4.75 (m, 1H), 5.10–5.35 (m, 3H), 5.71 (d, 1H, J=5 Hz), 5.75 (d, 1H, J=8 Hz)

(2) [N-(t-butoxycarbonyl)-S-(2,3,4-tri-O-acetyl-α-L-fucopyranosyl)-D-cysteinyl]-L-glutamic acid 1-methylamide 5-benzyl ester:

N-(t-Butoxycarbonyl)-L-glutamic acid 1-methylamide 5-benzyl ester [0.71 g, S-isomer of the compound (XV) wherein R$^3$ is methyl group, and n is 1] is dissolved in methylene chloride (7 ml), and further thereto is added with stirring TFA (2 ml) under ice-cooling. The mixture is stirred at room temperature for one hour, and concentrated under reduced pressure to give TFA salt of the de-protected product [S-isomer of the compound (XIIa) wherein R$^3$ is methyl group, and n is 1] as a syrup. The compound obtained in the above (1) (1.0 g) and TEA (0.23 g) are dissolved in THF (7 ml), and thereto is added with stirring ethyl chlorocarbonate (0.24 g) under ice cooling. The mixture is stirred for 5 minutes, and thereto is added a solution of TFA salt of the de-protected product obtained in the above and TEA (0.62 g) in THF (3 ml). The mixture is stirred for 15 minutes under ice-cooling, and stirred at room temperature for 12 hours. The mixture is concentrated under reduced pressure, and the resulting residue is purified by silica gel medium-pressure liquid chromatography (chloroform: MeOH=20:1) to give [N-(t-butoxycarbonyl)-S-(2,3,4-tri-O-acetyl-(α-L-fucopyranosyl)-D-cysteinyl]-L-glutamic acid 1-methylamide 5-benzyl ester (1.08 g) as a syrup.

$^1$H-NMR (CDCl$_3$)δ: 1.21 (d, 3H, J=6.4 Hz), 1.46 (s, 9H), 1.99 (s, 3H), 2.06 (s, 3H), 2.17 (s, 3H), 2.3–2.7 (m, 2H), 2.7–2.9 (m, 4H), 3.1–3.3 (m, 1H), 4.2–4.6 (m, 3H), 5.05–5.35 (m, 5H), 5.56 (d, 1H, J=6.6 Hz), 5.67 (d, 1H, J=5.6 Hz), 6.49 (bs, 1H), 7.15 (d, 1H, J=7.9 Hz), 7.3–7.5 (m, 5H).

Example 64

Preparation of [N-(t-butoxycarbonyl)-S-(2,3,4-tri-O-acetyl-α-L-fucopyranosyl)-D-cysteinyl]-D-glutamic acid 1-methylamide 5-benzyl ester [stereoisomer of the compound (IV-1) wherein R$^4$ is methylcarbamoyl group, and n is 1]:

[N-(t-Butoxycarbonyl)-D-glutamic acid 1-methylamide 5-benzyl ester [0.36 g, R-isomer of the compound (XV) wherein R$^3$ is methyl group, and n is 1] is dissolved in methylene chloride (5 ml), and thereto is added with stirring TFA (5 ml) under ice-cooling. The mixture is stirred for three hours, and concentrated. To the mixture is added chloroform (50 ml), and the mixture is washed with a saturated aqueous sodium carbonate solution, dried, and concentrated under reduced pressure to give the de-protected product [R-isomer of the compound (XIIa) wherein R$^3$ is methyl group, and n is 1] as a syrup. In DMF (20 ml) are dissolved the resulting syrup of the de-protected product and the compound obtained in Example 63 (1) (0.5 g), and WSC (0.29 g) and HOBt (0.23 g) are added with stirring to the mixture under ice cooling. The mixture is stirred at room temperature for 20 hours, and to the reaction mixture is added ethyl acetate (100 ml). The extract is washed with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (ethyl acetate:n-hexane=1:1) to give [N-(t-butoxycarbonyl)-S-(2,3,4-tri-O-acetyl-α-L-fucopyranosyl)-D-cysteinyl]-D-glutamic acid 1-methylamide 5-benzyl ester (0.46 g) as a syrup.

$^1$H-NMR (CDCl$_3$)δ: 1.18 (d, 3H, J=6.5 Hz), 1.47 (s, 9H), 1.98 (s, 3H), 2.05 (s, 3H), 2.16 (s, 3H), 2.35–2.6 (m, 2H), 2.77 (d, 3H, J=4.7 Hz), 3.0–3.2 (m, 1H), 4.2–4.6 (m, 3H), 5.11 (s, 2H), 5.05–5.35 (m, 3H), 5.66 (d, 1H, J=5.5 Hz), 5.8 (d, 1H, J=7.1 Hz), 6.96 (q, 1H, J=4.7 Hz), 7.2–7.4 (m, 5H), 7.52 (d, 1H, J=7.8 Hz).

Example 65

Preparation of [N-(2-tetradecylhexadecanoyl)-S-(2,3,4-tri-O-acetyl-α-L-fucopyranosyl)-L-cysteinyl]-L-glutamic acid 1-methylamide 5-benzyl ester [stereoisomer of the compound (IV-2) wherein R$^1$ is 2-tetradecylpentadecyl group, R$^4$ is methylcarbamoyl group, and n is 1]:

The compound obtained in Example 61 (0.88 g) is dissolved in methylene chloride (18 ml), and thereto is added TFA (9 ml). The mixture is stirred at room temperature for one hour, concentrated, and thereto is added chloroform (50 ml). The mixture is washed with chilled 5% aqueous sodium hydrogen carbonate solution, dried, and concentrated under reduced pressure. The syrup of the de-protected product thus obtained, 2-tetradecylhexadecanoic acid (0.55 g), HOBt (0.24 g) are dissolved in DMF (63 ml), and thereto is added with stirring WSC (0.3 g) under ice-cooling. The mixture is stirred at room temperature for 16 hours, and the reaction mixture is poured into ice-water (630 ml). The mixture is extracted three times with ethyl acetate, and the extract is washed with 5% aqueous sodium hydrogen carbonate solution, dried, and concentrated under reduced pressure. The resulting residue is purified by silica gel medium-pressure liquid chromatography (chloroform:MeOH= 100:0→300:1) to give [N-(2-tetradecylhexadecanoyl)-S-(2, 3,4-tri-O-acetyl-α-L-fucopyranosyl)-L-cysteinyl]-L-glutamic acid 1-methylamide 5-benzyl ester (0.8 g) as a syrup.

$^1$H-NMR (CDCl$_3$)δ: 0.8–0.95 (m, 6H), 1.17 (d, 3H, J=6.5 Hz), 1.2–1.55 (m, 52H), 1.99 (s, 3H), 2.04 (s, 3H), 2.15 (s, 3H), 2.3–2.65 (m, 2H), 2.79 (d, 3H, J=4.8 Hz), 2.84 (dd, 1H, J=6.2, 13.7 Hz), 3.0 (dd, 1H, J=5.7, 13.8 Hz), 4.3–4.45 (m, 2H), 4.5–4.66 (m, 1H), 5.13 (s, 2H), 5.13–5.3 (m, 3H), 5.75 (d, 1H, J=4.8 Hz), 6.2 (d, 1H, J=7.0 Hz), 6.44 (q, 1H, J=4.8 Hz), 7.19 (d, 1H, J=7.5 Hz), 7.25–7.4 (m, 5H).

Example 66

Preparation of [N-(2-tetradecylhexadecanoyl)-S-(2,3,4-tri-O-acetyl-α-L-fucopyranosyl)-L-cysteinyl]-D-glutamic acid 1-methylamide 5-benzyl ester [stereoisomer of the compound (IV-2) wherein R$^1$ is 2-tetradecylpentadecyl group, R$^4$ is methylcarbamoyl group, and n is 1]:

The compound obtained in Example 62 (0.2 g) is dissolved in methylene chloride solution (4 ml), and thereto is added TFA (2 ml). The mixture is stirred at room temperature for two hours, concentrated, and thereto is added chloroform (50 ml). The mixture is washed with a 5% aqueous sodium hydrogen carbonate solution, dried, and concentrated under reduced pressure. The syrup of the de-protected product thus obtained, 2-tetradecylhexadecanoic acid (0.13 g) and HOBt (55 mg) are dissolved in DMF (12.5 ml), and thereto is added with stirring WSC (69 mg) under ice-cooling. The mixture is stirred at room temperature for 15.5 hours, and poured into ice-water (120 ml). The mixture is extracted three times with ethyl acetate, washed with a 5% aqueous sodium hydrogen carbonate solution, dried, and concentrated under reduced pressure. The resulting residue is purified by silica gel medium-pressure liquid chromatography (chloroform:MeOH=100:0→500:1) to give [N-(2-tetradecylhexadecanoyl)-S-(2,3,4-tri-O-acetyl-α-L-fucopyranosyl)-L-cysteinyl]-D-glutamic acid 1-methylamide 5-benzyl ester (0.15 g) as a syrup.

$^1$H-NMR (CDCl$_3$)δ: 0.8–0.95 (m, 6H), 1.15 (d, 3H, J=6.5 Hz), 1.1–1.7 (m, 52H), 1.99 (s 3H), 2.05 (s, 3H), 2.15 (s, 3H), 2.35–2.65 (m, 2H), 2.76 (d, 3H, J=4.7 Hz), 2.85–3.0 (m, 2H), 4.3–4.55 (m, 3H), 5.13 (s, 2H), 5.15–5.3 (m, 3H), 5.74 (d, 1H, J=4.9 Hz), 6.35 (bs, 1H), 6.74 (bs, 1H).

Example 67

Preparation of [N-(2-tetradecylhexadecanoyl)-S-(2,3,4-tri-O-acetyl-α-L-fucopyranosyl)-D-cysteinyl]-L-glutamic acid 1-methylamide 5-benzyl ester [stereoisomer of the compound (IV-2) wherein R$^1$ is 2-tetradecylpentadecyl group, R$^4$ is methylcarbamoyl group, and n is 1]:

The compound obtained in Example 63 (0.5 g) is dissolved in methylene chloride solution (5 ml), and thereto is added with stirring TFA (2.5 ml) under ice-cooling, and the mixture is stirred for one hour. The reaction mixture is concentrated, and thereto is added chloroform (50 ml). The mixture is washed with a saturated aqueous sodium hydrogen carbonate solution, dried, and concentrated under reduced pressure. The resulting syrup of the de-protected product is dissolved in DMF (30 ml), and thereto are added 2-tetradecylhexadecanoic acid (0.3 g) and HOBt (0.1 g). To the mixture is added with stirring WSC (0.16 g) under ice-cooling, and the mixture is stirred at room temperature for 15 hours. To the reaction mixture is added ethyl acetate (100 ml), and the mixture is washed with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give [N-(2-tetradecylhexadecanoyl)-S-(2,3,4-tri-O-acetyl-α-L-fucopyranosyl)-D-cysteinyl]-L-glutamic acid 1-methylamide 5-benzyl ester (0.23 g) as a syrup.

$^1$H-NMR (CDCl$_3$)δ: 0.8–0.95 (m, 6H), 1.19 (d, 3H, J=6.5 Hz), 1.1–1.7 (m, 57H), 1.98 (s, 3H), 2.05 (s, 3H), 2.15 (s, 3H), 1.9–2.3 (m, 1H), 2.3–2.7 (m, 2H), 2.76 (d, 3H, J=4.8 Hz), 2.84 (dd, 1H, J=5.4, 14.3 Hz), 3.1 (dd, 1H, J=6.2, 14.1 Hz), 4.3–4.5 (m, 2H), 4.5–4.7 (m, 1H), 5.0–5.3 (m, 5H), 5.68 (d, 1H, J=5.5 Hz), 6.6–6.8 (m, 2H), 7.2–7.5 (m, 6H).

Example 68

Preparation of [N-(2-tetradecylhexadecanoyl)-S-(2,3,4-tri-O-acetyl-α-L-fucopyranosyl)-D-cysteinyl]-D-glutamic acid 1-methylamide 5-benzyl ester [stereoisomer of the compound (IV-2) wherein R$^1$ is 2-tetradecylpentadecyl group, R$^4$ is methylcarbamoyl group, and n is 1]:

The compound obtained in Example 64 (0.46 g) is dissolved in methylene chloride solution (5 ml), and thereto is added with stirring TFA (5 ml) under ice-cooling, and the mixture is stirred for three hours. The reaction mixture is concentrated, and thereto is added chloroform (80 ml). The mixture is washed with a saturated aqueous sodium carbonate solution, dried, and concentrated under reduced pressure. The resulting syrup of the de-protected product is dissolved in DMF (50 ml), and thereto is added 2-tetradecylhexadecanoic acid (0.29 g), and dissolved with heating. The mixture is cooled to room temperature, and thereto are added WSC (0.18 g) and HOBt (0.15 g). The mixture is stirred at room temperature for 22 hours. To the reaction mixture is added ethyl acetate (120 ml), and the mixture is washed with 1N hydrochloric acid, a saturated aqueous sodium hydrogen carbonate solution, a saturated aqueous sodium chloride solution, dried, and concentrated under reduced pressure. The resulting residue is purified by preparative thin layer chromatography (chloroform:MeOH= 20:1) to give [N-(2-tetradecylhexadecanoyl)-S-(2,3,4-tri-O-acetyl-α-L-fucopyranosyl)-D-cysteinyl]-D-glutamic acid 1-methylamide 5-benzyl ester (0.21 g) as a syrup.

$^1$H-NMR (CDCl$_3$)δ: 0.8–0.95 (m, 6H), 1.18 (d, 3H, J=6.5 Hz), 1.0–1.9 (m, 52H), 1.98 (s, 3H), 2.06 (s, 3H), 2.16 (s, 3H), 2.35–2.66 (m, 2H), 2.8 (d, 3H, J=4.8 Hz), 2.87 (dd, 1H, J=5.6, 14.1 Hz), 3.01 (dd, 1H, J=5.7, 14.0 Hz), 4.33–4.5 (m, 2H), 4.59–4.7 (m, 1H), 5.08–5.35 (m, 6H), 5.67 (d, 1H, J=5.5 Hz), 6.42 (d, 1H, J=7.3 Hz), 6.46 (d, 1H, J=4.9 Hz), 7.14 (d, 1H, J=7.5 Hz), 7.28–7.45 (m, 5H).

Example 69

Preparation of [N-(2-tetradecylhexadecanoyl)-S-(α-L-fucopyranosyl)-L-cysteinyl]-L-glutamic acid 1-methylamide [stereoisomer of the compound [Ic((α)] wherein R$^1$ is 2-tetradecylpentadecyl group, R$^2$ is methylcarbamoyl group, and n is 1]:

(1) [N-(2-tetradecylhexadecanoyl)-S-(2,3,4-tri-O-acetyl-α-L-fucopyranosyl)-L-cysteinyl]-L-glutamic acid 1-methylamide:

To a suspension of the compound obtained in Example 65 (0.8 g) in methanol (300 ml) is added 10% palladium carbon (0.6 g), and the mixture is stirred at room temperature under hydrogen pressure (4–5 atms) for 6 hours. The catalyst is removed by filtration, and the filtrate is concentrated under reduced pressure to give [N-(2-tetradecylhexadecanoyl)-S-(2,3,4-tri-O-acetyl-α-L-fucopyranosyl)-L-cysteinyl]-L-glutamic acid 1-methylamide (0.6 g).

(2) [N-(2-tetradecylhexadecanoyl)-S-(α-L-fucopyranosyl)-L-cysteinyl]-L-glutamic acid 1-methylamide:

The compound obtained in the above (1) (0.28 g) is dissolved in methanol (45 ml), and thereto is added 28% NaOMe/methanol solution (0.12 ml), and the mixture is stirred at room temperature for 1.5 hour. To the reaction mixture is added Dowex 50W-X8 (5.0 g), and the mixture is stirred at room temperature for 10 minutes. The insoluble materials are removed by filtration, and washed with a mixture of chloroform-methanol. The filtrate and the washings are combined, and concentrated under reduced pressure, and the precipitated solid is collected by filtration, and washed with methanol to give [N-(2-tetradecylhexadecanoyl)-S-(α-L-fucopyranosyl)-L-cysteinyl]-L-glutamic acid 1-methylamide (0.12 g) as a colorless powder.

M.p. 186–188° C.; $^1$H-NMR (DMSO-d$_6$)δ: 0.75–0.9 (m, 6H), 1.11 (d, 3H, J=6.4 Hz), 1.1–1.55 (m, 52H), 1.6–1.8 (m, 1H), 1.8–2.0 (m, 1H), 2.1–2.25 (m, 3H), 2.58 (d, 3H, J=4.4 Hz), 3.35–3.45 (m, 1H), 3.45–3.5 (m, 1H), 3.84 (dd, 1H, J=5.4, 9.8 Hz), 3.95–4.1 (m, 1H), 4.1–4.25 (m, 1H), 4.3–4.45 (m, 1H), 5.21 (d, 1H, J=5.4 Hz), 7.75 (q, 1H, J=4.7 Hz), 7.88 (d, 1H, J=7.9 Hz), 8.14 (d, 1H, J=7.9 Hz), 12.05 (bs, 1H).

Mass spectrum (m/e): 844 (M+H)$^+$

Example 70

Preparation of [N-(2-tetradecylhexadecanoyl)-S-(α-L-fucopyranosyl)-L-cysteinyl]-D-glutamic acid 1-methylamide [stereoisomer of the compound [Ic(α)] wherein R$^1$ is 2-tetradecylpentadecyl group, R$^2$ is methylcarbamoyl group, and n is 1]:

(1) [N-(2-tetradecylhexadecanoyl)-S-(2,3,4-tri-O-acetyl-α-L-fucopyranosyl)-L-cysteinyl]-D-glutamic acid 1-methylamide:

To a suspension of the compound obtained in Example 66 (0.24 g) in methanol (100 ml) is added 10% palladium carbon (0.2 g), and the mixture is stirred at room temperature under hydrogen pressure (4–5 atms) for 6 hours. The catalyst is removed by filtration, and the filtrate is concentrated under reduced pressure to give [N-(2-tetradecylhexadecanoyl)-S-(2,3,4-tri-O-acetyl-α-L-fucopyranosyl)-L-cysteinyl]-D-glutamic acid 1-methylamide (129 mg).

(2) [N-(2-tetradecylhexadecanoyl)-S-(α-L-fucopyranosyl)-L-cysteinyl]-D-glutamic acid 1-methylamide:

The compound obtained in the above (1) (127 mg) is dissolved in methanol (20 ml), and thereto is added 28% NaOMe/methanol solution (53 μl), and the mixture is stirred at room temperature for 80 minutes. To the mixture is added Dowex 50W-X8 (5.0 g), and the mixture is stirred at room temperature for 10 minutes, and thereto is added methanol. The insoluble materials are removed by filtration, and the filtrate is concentrated under reduced pressure. The resulting residue is purified by preparative thin layer chromatography (chloroform:methanol=5:1), and to the resulting solid is added a mixture of chloroformmethanol (4:1). The mixture is filtered. The filtrate is concentrated under reduced pressure to give [N-(2-tetradecylhexadecanoyl)-S-(α-L-fucopyranosyl)-L-cysteinyl]-D-glutamic acid 1-methylamide (0.12 g) as a colorless powder.

M.p. 195–199° C. (decomposed); $^1$H-NMR (DMSO-d$_6$)δ: 0.75–0.95 (m, 6H), 1.11 (d, 3H, J=6.4 Hz), 1.0–1.6 (m, 52H), 1.6–1.8 (m, 1H), 1.85–2.05 (m, 1H), 2.1–2.3 (m, 3H), 2.56 (d, 3H, J=4.5 Hz), 2.7–2.85 (m, 1H), 3.85 (dd, 1H, J=5.3, 9.8 Hz), 3.9–4.1 (m, 1H), 4.1–4.22 (m, 1H), 4.25–4.4 (m, 1H), 4.47 (d, 1H, J=4.5 Hz), 5.21 (d, 1H, J=5.4 Hz), 7.76 (q, 1H, J=4.7 Hz), 8.22 (d, 1H, J=7.3 Hz).

Mass spectrum (m/e): 844 (M+H)$^+$

Example 71

Preparation of [N-(2-tetradecylhexadecanoyl)-S-(α-L-fucopyranosyl)-D-cysteinyl]-L-glutamic acid 1-methylamide [stereoisomer of the compound [Ic(α)] wherein R$^1$ is 2-tetradecylpentadecyl group, R$^2$ is methylcarbamoyl group, and n is 1]:

To a suspension of the compound obtained in Example 67 (0.2 g) in methanol (50 ml) is added 10% palladium carbon (0.2 g), and the mixture is stirred under hydrogen pressure (5 atms) at room temperature overnight. The catalyst is removed by filtration, and the filtrate is concentrated under reduced pressure. The resulting residue is dissolved in methanol (10 ml), and thereto is added 28% NaOMe/methanol solution (50 mg). The mixture is stirred at room temperature for 35 minutes. To the mixture is added Dowex 50W-X8 (5.0 g), and the mixture is stirred at room temperature for 5 minutes. To the mixture is added chloroform-methanol (5:1, 5 ml), and the insoluble materials are removed by filtration, and the filtrate is concentrated under reduced pressure to give [N-(2-tetradecylhexadecanoyl)-S-(α-L-fucopyranosyl)-D-cysteinyl]-L-glutamic acid 1-methylamide (0.1 g) as a colorless powder.

M.p. 182–192° C.; $^1$H-NMR (DMSO-d$_6$)δ: 0.65–0.95 (m, 6H), 1.09 (d, 3H, J=6.4 Hz), 1.0–1.58 (m, 52H), 1.6–1.82 (m, 1H), 1.85–2.05 (m, 1H), 2.05–2.32 (m, 3H), 2.57 (d, 3H, J=4.3 Hz), 2.62–2.82 (m, 2H), 3.87 (dd, 1H, J=5.6, 9.7 Hz), 3.9–4.05 (m, 1H), 4.1–4.26 (m, 1H), 4.3–4.55 (m, 1H), 5.36 (d, 1H, J=5.3 Hz), 7.61 (d, 1H, J=4.6 Hz), 7.98 (d, 1H, J=7.9 Hz), 8.12 (d, 1H, J=7.7 Hz), 12.1 (bs, 1H).

Mass spectrum: 844 (M+H)$^+$

Example 72

Preparation of [N-(2-tetradecylhexadecanoyl)-S-(α-L-fucopyranosyl)-D-cysteinyl]-D-glutamic acid 1-methylamide [stereoisomer of the compound [Ic(α)] wherein R$^1$ is 2-tetradecylpentadecyl group, R$^2$ is methylcarbamoyl group, and n is 1]:

To a suspension of the compound obtained in Example 68 (0.18 g) in methanol (30 ml) is added active carbon (1.0 g). The mixture is stirred at room temperature for 15 minutes, and the insoluble materials are removed by filtration. To the resulting methanol solution is added 10% palladium carbon (0.14 g), and the mixture is stirred at room temperature under hydrogen pressure (3–4 atms) for 4 hours. The catalyst is removed by filtration, and the filtrate is concentrated under reduced pressure. The resulting residue is dissolved to methanol (30 ml), and thereto is added 28% NaOMe/methanol solution (66 mg), and the mixture is stirred at room temperature for 0.5 hour. To the mixture is added Dowex 50W-X8 (5.0 g), and the mixture is stirred at room temperature for 3 minutes. The insoluble materials are removed by filtration, and the filtrate is concentrated under reduced pressure. The precipitated solid is collected by filtration from water to give [N-(2-tetradecylhexadecanoyl)-S-(α-L-fucopyranosyl)-D-cysteinyl]-D-glutamic acid 1-methylamide (15 mg) as a colorless powder.

M.p. gradually melted at 155° C.; $^1$H-NMR (DMSO-d$_6$)δ: 0.65–0.95 (m, 6H), 1.09 (d, 3H, J=6.4 Hz), 1.0–1.58 (m, 52H), 1.6–1.82 (m, 1H), 1.85–2.05 (m, 1H), 2.05–2.32 (m, 3H), 2.57 (d, 3H, J=4.3 Hz), 2.62–2.82 (m, 2H), 3.87 (dd, 1H, J=5.6, 9.7 Hz), 3.95–4.1 (m, 1H), 4.1–4.26 (m, 1H), 4.3–4.55 (m, 1H), 5.36 (d, 1H, J=5.3 Hz), 7.61 (d, 1H, J=4.6 Hz), 7.98 (d, 1H, J=7.9 Hz), 8.12 (d, 1H, J=7.7 Hz), 12.1 (bs, 1H).

Mass spectrum: 844 (M+H)$^+$

Example 73

Preparation of [O-(2,3,4-tri-O-acetyl-β-L-fucopyranosyl)-L-cysteinyl]-D-glutamic acid 1-methylamide 5-benzyl ester [stereoisomer of the compound (III-3) wherein R$^4$ is methylcarbamoyl group, and n is 1]:

To Molecular Sieves 4 Å (1.0 g) are added methylene chloride (8 ml), AgOTf (1.1 g) and SnCl$_2$ (0.8 g), and the mixture is stirred at room temperature under argon atmosphere for 0.5 hour, and cooled to −20° C. To the mixture are added a solution of (2,3,4-tri-O-acetyl)-L-fucopyranosyl fluoride [1.4 g, the compound (VII)] in methylene chloride (3 ml), and a solution of [N-tert-butoxycarbonyl-L-cysteinyl-D-glutamic acid 1-methylamide 5-benzyl ester [1.0 g, the compound obtained in Reference Example 11] in methylene chloride (5 ml). The mixture is stirred for 18 hours while it is gradually warmed to room temperature. The insoluble materials are removed by filtration, and the filtrate is concentrated under reduced pressure. The resulting residue is purified by preparative thin layer chromatography (chloroform:MeOH=9:1) to give [O-(2,3,4-tri-O-acetyl-β-L-fucopyranosyl)-L-cysteinyl]-D-glutamic acid 1-methylamide 5-benzyl ester (0.9 g) as a syrup.

$^1$H-NMR (CDCl$_3$)δ: 1.2 (d, 3H, J=6.9 Hz), 1.98 (s, 3H), 2.06 (s, 3H), 2.18 (s, 3H), 2.3–2.6 (m, 4H), 2.77 (d, 3H, J=4.7 Hz), 2.98 (dd, 1H, J=4.8, 14.0 Hz), 3.08 (dd, 1H, J=7.1, 14.0 Hz), 3.59 (dd, 1H, 4.8, 6.9 Hz), 3.77–3.9 (m, 1H), 4.35–4.55 (m, 1H), 4.51 (d, 1H, J=9.7 Hz), 5.04 (dd, 1H, J=3.4, 10.0 Hz), 5.08 (d, 1H, J=12.4 Hz), 5.13 (d, 1H, J=12.4 Hz), 5.17 (t, 1H, J=9.9 Hz), 5.26 (dd, 1H, J=0.5, 3.1 Hz), 7.07 (q, 1H, J=4.4 Hz), 7.25–7.4 (m, 5H), 7.99 (d, 1H, J=8.4 Hz).

Example 74

Preparation of [N-(2-tetradecylhexadecanoyl)-S-(2,3,4-tri-O-acetyl-β-L-fucopyranosyl)-L-cysteinyl]-D-glutamic acid 1-methylamide 5-benzyl ester [stereoisomer of the compound (III-4) wherein R$^1$ is 2-tetradecylpentadecyl group, R$^4$ is methylcarbamoyl group, and n is 1]:

The compound of the Example 73 (0.9 g) and 2-tetradecylhexadecanoic acid (0.7 g) are dissolved in DMF (50 ml) with heating, and the mixture is cooled to room temperature. To the mixture is added WSC (0.4 g) and HOBt (0.3 g), and the mixture is stirred for 21 hours. To the reaction mixture is added ethyl acetate (120 ml), and the mixture is washed successively with 1N hydrochloric acid, a saturated aqueous sodium hydrogen carbonate solution, and a saturated aqueous sodium chloride solution, dried, and concentrated under reduced pressure. The resulting residue is purified by preparative thin layer chromatography (chloroform:MeOH=20:1) to give [N-(2-tetradecylhexadecanoyl)-S-(2,3,4-tri-O-acetyl-β-L-fucopyranosyl)-L-cysteinyl]-D-glutamic acid 1-methylamide 5-benzyl ester (0.9 g) as colorless crystals.

M.p. 104–105° C.; $^1$H-NMR (CDCl$_3$)δ: 0.8–0.95 (m, 6H), 1.05–1.35 (m, 55H), 1.36–1.5 (m, 1H), 1.5–1.65 (m, 1H), 2.0 (s, 3H), 2.07 (s, 3H), 2.19 (s, 3H), 2.45–2.6 (m, 2H), 2.67 (dd, 1H, J=7.6, 14.3 Hz), 2.76 (d, 3H, J=4.7 Hz), 3.34 (dd, 1H, J=7.0, 14.4 Hz), 3.75–3.88 (m, 1H), 4.32–4.5 (m, 1H), 4.42 (d, 1H, J=9.9 Hz), 5.03 (dd, 1H, 3.2, 10.0 Hz), 5.09 (d, 1H, J=12.3 Hz), 5.16 (d, 1H, J=12.2 Hz), 5.27 (d, 1H, J=3.1 Hz), 5.35 (t, 1H, J=9.9 Hz), 6.48 (d, 1H, J=5.9 Hz), 6.7 (q, 1H, J=4.8 Hz), 7.09 (d, 1H, J=8.1 Hz, 7.3–7.45 (m, 5H).

Elementary Analysis for $C_{58}H_{97}N_3O_{12}S$: Calculated: C, 65.59; H, 9.22; N, 3.96; Found: C, 65.41; H, 9.17; N, 3.65

Example 75

Preparation of [N-(2-tetradecylhexadecanoyl)-S-(β-L-fucopyranosyl)-L-cysteinyl]-D-glutamic acid 1-methylamide [stereoisomer of the compound [Ic(β)] wherein $R^1$ is 2-tetradecylpentadecyl group, $R^2$ is methylcarbamoyl group, and n is 1]:

To a solution of the compound obtained in Example 74 (0.4 g) in methanol (30 ml) is added 10% palladium carbon (0.35 g), and the mixture is stirred under hydrogen pressure (3–4 atms) at room temperature for 5 hours. The catalyst is removed by filtration, and the filtrate is concentrated under reduced pressure. The resulting residue is dissolved in methanol (30 ml), and thereto is added 28% NaOMe/methanol solution (0.15 g), and the mixture is stirred at room temperature for 0.5 hour. To the mixture is added Dowex 50W-X8 (5.0 g), and the mixture is stirred at room temperature for 3 minutes. The insoluble materials are removed by filtration, and the filtrate is concentrated under reduced pressure. The precipitated solid is collected by filtration from ether to give [N-(2-tetradecylhexadecanoyl)-S-(β-L-fucopyranosyl)-L-cysteinyl]-D-glutamic acid 1-methylamide (0.2 g) as a colorless powder.

M.p. 169–172° C.; $^1$H-NMR (DMSO-d$_6$)δ: 0.7–0.95 (m, 6H), 1.12 (d, 3H, J=6.4 Hz), 0.95–1.55 (m, 52H), 1.56–1.8 (m, 1H), 1.85–2.08 (m, 1H), 2.1–2.35 (m, 3H), 2.56 (d, 3H, J=4.3 Hz), 2.81 (d, 2H, J=7.3 Hz), 3.0–3.6 (m, 4H), 4.05–4.23 (m, 1H), 4.46 (d, 1H, J=8.6 Hz), 4.25–4.4 (m, 1H), 7.81 (q, 1H, J=4.7 Hz), 8.11 (d, 1H, J=8.3 Hz), 8.15 (d, 1H, J=6.6 Hz), 12.5 (bs, 1H).

Mass spectrum: 844 (M+H)$^+$ Elementary Analysis for $C_{45}H_{85}N_3O_9S\cdot0.5H_2O$: Calculated: C, 63.35; H, 10.16; N, 4.92; Found: C, 63.47; H, 10.01; N, 4.71

Example 76

Preparation of L-arginine salt of [N-(2-tetradecylhexadecanoyl)-O-(α-L-fucofuranosyl)-D-seryl]-L-glutamic acid 1-methylamide [α-anomer of the compound (Ib) wherein $R^1$ is 1-tetradecylpentadecyl group, $R^2$ is methylcarbamoyl group, and n is 1]:

The compound obtained in Example 19 (50 mg) is suspended to ion-exchange water (50 ml), and the mixture is subjected to ultrasonic treatment. To the mixture is added L-arginine (10.5 mg). The mixture is dissolved with heating, and lyophilized to give L-arginine salt of the title compound (56 mg) as a colorless powder.

M.p. 175° C. (decomposed); $^1$H-NMR (DMSO-d$_6$)δ: 0.75–0.95 (m, 6H), 1.08 (d, 3H, J=6.5 Hz), 1.1–1.5 (m, 54H), 1.5–2.2 (m, 9H), 2.55 (d, 3H, J=4.2 Hz), 3.6–3.8 (m, 5H), 3.9–4.05 (m, 1H), 4.1–4.2 (m, 1H), 4.2–4.4 (m, 1H), 4.69 (d, 1H, J=4.2 Hz), 7.47 (d, 1H, J=3.9 Hz), 8.51 (d, 1H, J=7.3 Hz), 8.85 (bs, 1H).

Example 77

Preparation of arginine salt of [N-(2-tetradecylhexadecanoyl)-O-(α-L-fucopyranosyl)-D-seryl]-L-glutamic acid 1-methylamide [α-anomer of the compound (Ia) wherein $R^1$ is 1-tetradecylpentadecyl group, $R^2$ is methylcarbamoyl group, and n is 1]:

The compound obtained in Example 47 (41.7 mg) is suspended in ion exchange water (10 ml), and the mixture is subjected to ultrasonic treatment. To the mixture is added L-arginine (8.8 mg), and further thereto is added ion exchange water (10 ml). The mixture is heated, and lyophilized to give L-arginine salt (46 mg) of the titled compound as a colorless powder.

M.p. 187° C. (decomposed); $^1$H-NMR (DMSO-d$_6$)δ: 0.75–0.95 (m, 6H), 1.04 (d, 3H, J=6.5 Hz), 1.1–1.5 (m, 54H), 1.5–1.7 (m, 4H), 1.7–1.9 (m, 2H), 2.0–2.15 (m, 2H), 2.15–2.3 (m, 1H), 2.54 (d, 3H, J=4.4 Hz), 3.55–3.8 (m, 4H), 4.0–4.1 (m, 1H), 4.3–4.45 (m, 1H), 4.63 (d, 1H, J=3.0 Hz), 7.69 (q, 1H, J=4.1 Hz), 7.91 (d, 1H, 5.9 Hz), 8.8–8.95 (m, 1H)

Example 78

Preparation of tablets:

Distilled water (150 parts by weight) is added to the compound obtained in Example 19 (100 parts by weight), lactose (30 parts by weight), crystalline cellulose (20 parts by weight), hydroxypropylmethylcellulose (5 parts by weight), and carboxymethylcellulose (20 parts by weight), and the mixture is duly kneaded, and crushed and dried. To the resulting dried mass is added magnesium stearate (5 parts of weight), and the mixture is mixed to give granules. The granules are subjected to compressed tableting to give tablets (diameter; 8 mm, 180 mg/tablet) containing 100 mg of the compound of Example 19 per each.

Example 79

Preparation of injection:

The compound obtained in Example 19 (0.5 part by weight) and sorbitol (5 parts by weight) are dissolved in distilled water for injection (100 parts by weight). The aqueous solution thus obtained is filtered through a membrane filter. The filtrate (each 5 g per ampule) is put into ampules which are previously purged with nitrogen gas. The ampules are sterilized at 120° C. for 15 minutes to give the injection preparing containing 25 mg of the compound of Example 19 per ample.

We claim:

1. A compound of the formula (I):

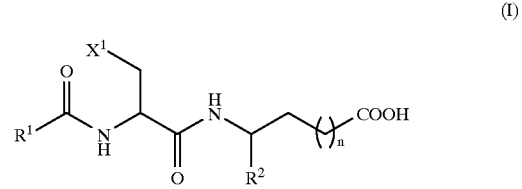

wherein $X^1$ is a group of one of the following formulae (1), (2) and (3):

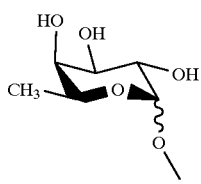

(1)

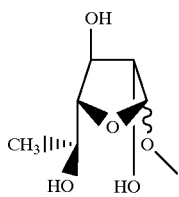

(2)

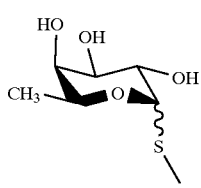

(3)

$R^1$ is a branched long chain alkyl group, $R^2$ is —CONHR$^3$, a carboxyl group or a hydrogen atom, n is an integer of 0, 1 or 2, and $R^3$ is a lower alkyl group or a phenyl group, or a pharmaceutically acceptable salt thereof.

2. A compound of the formula (II):

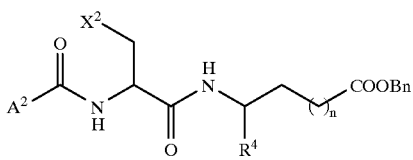

(II)

wherein $X^2$ is a group of one of the following formulae (4) and (5):

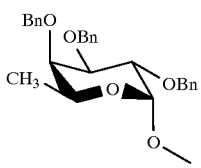

(4)

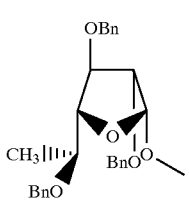

(5)

$A^1$ is a tert-butoxy group or a branched long chain alkyl group, Bn is a benzyl group, $R^4$ is —CONHR$^3$, a benzyloxycarbonyl group, or a hydrogen atom, n is an integer of 0, 1 or 2, and $R^3$ is a lower alkyl group or a phenyl group.

3. A compound of the formula (III):

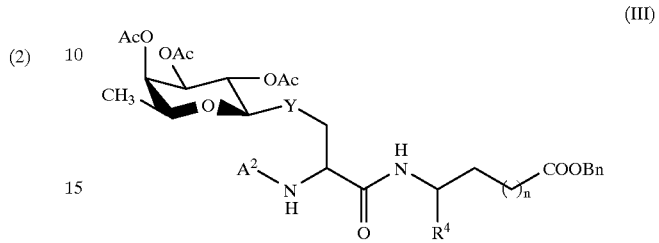

(III)

wherein Y is an oxygen atom or a sulfur atom, $A^2$ is a hydrogen atom or a branched long chain alkylcarbonyl group, $R^4$ is —CONHR$^3$, a benzyloxycarbonyl group, or a hydrogen atom, Ac is an acetyl group, n is an integer of 0, 1 or 2, and $R^3$ is a lower alkyl group or a phenyl group.

4. A compound of the formula (IV):

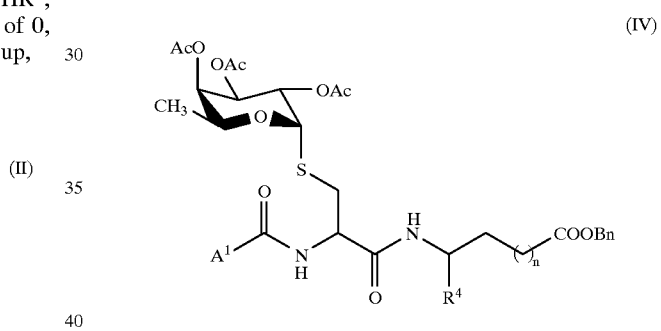

(IV)

wherein $A^1$ is a tert-butoxy group or a branched long chain alkyl group, $R^4$ is —CONHR$^3$, a benzyloxycarbonyl group, or a hydrogen atom, Ac is an acetyl group, n is an integer of 0, 1 or 2, and $R^3$ is a lower alkyl group or a phenyl group.

5. A drug which contains as an active ingredient the fucose derivative (I) as set forth in claim 1, or a pharmaceutically acceptable salt thereof.

6. A selectin inhibitor which contains as an active ingredient the fucose derivative (I) as set forth in claim 1, or a pharmaceutically acceptable salt thereof.

7. A drug for prophylaxis or treatment of inflammatory diseases or ischemic-reperfusion injury, which contains as an active ingredient the fucose derivative (I) as set forth in claim 1, or a pharmaceutically acceptable salt thereof.

* * * * *

UNITED STATES PATENT AND TRADEMARK OFFICE
CERTIFICATE OF CORRECTION

PATENT NO. : 5,919,769

DATED : JULY 6, 1999

INVENTOR(S) : TSUKIDA ET AL.

It is certified that error appears in the above-identified patent and that said Letters Patent is hereby corrected as shown below:

Col. 17, line 51, Scheme 4, formula (Va): "BnO" should read —HO—

Col. 73, line 38, claim 2, formula (II): "$A^2$" should read —$A^1$—

Col. 73, line 54, claim 2, formula (5): "(2)" should read —(5)—

Signed and Sealed this

Twenty-fifth Day of April, 2000

Q. TODD DICKINSON

*Attest:*

*Attesting Officer*     *Director of Patents and Trademarks*